US008148089B2

(12) United States Patent
Anderson et al.

(10) Patent No.: US 8,148,089 B2
(45) Date of Patent: Apr. 3, 2012

(54) ALPHA-SYNUCLEIN KINASE

(75) Inventors: John P. Anderson, San Francisco, CA (US); Kelly Banducci, Pleasanton, CA (US); Guriqbal S. Basi, Palo Alto, CA (US); David Chereau, San Mateo, CA (US); Tamie J. Chilcote, San Francisco, CA (US); Normand L. Frigon, Jr., Millbrae, CA (US); Jason Goldstein, Burlingame, CA (US); Irene Griswold, San Francisco, CA (US)

(73) Assignee: Elan Pharma International Limited, Dublin (IE)

( * ) Notice: Subject to any disclaimer, the term of this patent is extended or adjusted under 35 U.S.C. 154(b) by 167 days.

(21) Appl. No.: 12/702,201

(22) Filed: Feb. 8, 2010

(65) Prior Publication Data
US 2010/0143946 A1    Jun. 10, 2010

Related U.S. Application Data

(60) Division of application No. 12/030,849, filed on Feb. 13, 2008, which is a continuation-in-part of application No. 11/669,093, filed on Jan. 30, 2007, now Pat. No. 7,553,639.

(60) Provisional application No. 60/764,000, filed on Jan. 31, 2006.

(51) Int. Cl.
*G01N 33/53* (2006.01)
(52) U.S. Cl. ........................................ 435/7.1
(58) Field of Classification Search .................. 435/7.1
See application file for complete search history.

(56) References Cited

U.S. PATENT DOCUMENTS

| | | | |
|---|---|---|---|
| 6,861,422 | B2 | 3/2005 | Hoffmann et al. |
| 7,553,639 | B2 | 6/2009 | Chilcote et al. |
| 2002/0151464 | A1 | 10/2002 | Wolozin et al. |
| 2004/0176380 | A1 | 9/2004 | Hoffmann et al. |
| 2005/0014761 | A1 | 1/2005 | Hoffmann et al. |
| 2006/0025411 | A1 | 2/2006 | Hoffmann et al. |
| 2006/0057652 | A1 | 3/2006 | Green et al. |
| 2006/0074088 | A1 | 4/2006 | Munzert et al. |
| 2006/0079503 | A1 | 4/2006 | Schwede et al. |
| 2006/0223833 | A1 | 10/2006 | Schulze et al. |
| 2007/0010565 | A1 | 1/2007 | Prien et al. |
| 2007/0010566 | A1 | 1/2007 | Prien et al. |
| 2007/0015759 | A1 | 1/2007 | Schulze et al. |
| 2007/0037862 | A1 | 2/2007 | Siemeister et al. |
| 2007/0135387 | A1 | 6/2007 | Michaelides et al. |
| 2007/0179177 | A1 | 8/2007 | Brenchley et al. |
| 2007/0203143 | A1 | 8/2007 | Sheppard et al. |
| 2008/0300206 | A1 | 12/2008 | Anderson et al. |
| 2009/0304664 | A1* | 12/2009 | Lindquist et al. ............ 424/94.5 |
| 2011/0207796 | A1 | 8/2011 | Anderson et al. |

FOREIGN PATENT DOCUMENTS

| | | |
|---|---|---|
| WO | WO 01/60794 A2 | 8/2001 |
| WO | WO 2006/073734 A2 | 7/2006 |
| WO | WO 2006/124892 A2 | 11/2006 |
| WO | WO 2004/069175 A2 | 8/2007 |
| WO | WO 2007/089862 A2 | 8/2007 |
| WO | WO 2009/103010 A2 | 8/2009 |

OTHER PUBLICATIONS

U.S. Appl. No. 61/053,632, filed May 15, 2008, Anderson et al.
Anderson et al., "Phosphorylation of Ser-129 is the Dominant Pathological Modification of Alpha-Synclein in Familial and Sporadic Lewy Body Disease," *Journal of Biological Chemistry*, 281(40):29739-29752 (2006).
Chen et al., "Alpha-Synuclein Phosphorylation Controls Neurotoxicity and Inclusion Formation in a Drosophila Model of Parkinson Disease," *Nature Neuroscience*, 8(5):657-663 (2005).
Ellis et al., "Alpha-Synuclein is Phosphorylated by Members of the SCR Family of Protein-Tyrosine Kinases," *Journal of Biological Chemistry*, 276 (6):3879-3884 (2001).
Inglis et al., "Polo-like kinase 2 (PLK2) phosphorylates alpha-synuclein at serine 129 in the central nervous system," *J.Biol. Chem. Papers in Press*, pp. 1-11 (2008).
Harris, "Neuronal polo-like kinase in Alzheimer Disease indicates cell cycle changes," *Neurobiology of Aging*, 21:837-841 (2000).
Johnson et al., "Pharmacological and Functional Comparison of the Polo-like Kinase Family: Insight into Inhibitor and Substrate Specificity," *Biochemistry*, 46:9551-9563 (2007).
Naoto et al., "Serine 129 phosohorylation of alpha-synuclein induces unfolded protein response-mediated cell death," *Journal of Biological Chemistry*, 283(34):23179-23188 (2008) Biosis Preview, Abstract only.
Okochi et al., "Constitutive Physophorylation of The Parkinson's Disease Associated Alpha-Synuclein," *Journal of Biological Chemistry*, 275(1):390-397 (2000).
PCT Written Opinion of Oct. 28, 2008 for application PCT/US2007/002685.
PCT Search Report of Sep. 26, 2008 for application PCT/US2007/002685.
PCT Search Report of Sep. 16, 2009 for application PCT/US2009/034135.
PCT Written Opinion of Sep. 16, 2009 for application PCT/US2009/034135.
Pronin et al., "Syncleins Are a Novel Class of Substrates for G Protein-Coupled Receptor Kinases" *Journal of Biological Chemistry*, 275(34):26515-26522 (2000).
Steegmaier et al., "BI 2536, a Potent and Selective Inhibitor of Polo-like Kinase 1, Inhibits Tumor Growth in Vivo," *Current Biology*, 17:316-322 (2007).
Supplemental European Search Report of Sep. 1, 2009 for European Application 07762749.5.

(Continued)

*Primary Examiner* — Karen Carlson
(74) *Attorney, Agent, or Firm* — Alston & Bird LLP

(57) ABSTRACT

The invention provides agents and methods for treatment of diseases associated with Lewy body diseases (LBDs) in the brain of a patient. Preferred agents include inhibitors of PLK2 kinase.

12 Claims, 13 Drawing Sheets

OTHER PUBLICATIONS

Takahashi et al., "Phosphorylation of Alpha-Synuclein Characteristic of Synucleinopathy Lesions is Recapitulated in Alpha-Synuclein Transgenic Drosphila," *Neuroscience Letters*, 336:155-158 (2003).

Winkles et al., "Differential regulation of polo-like kinase 1, 2, 3, and 4 gene expression in mammalian cells and tissues," *Oncogene*, 24;260-266 (2005).

Zhou et al., "A Human Single-Chain Fv Intrabody Blocks Aberrant Cellular Effects of Overexpressed Alpha-Synuclein," *Molecular Therapy*, 10(6):1023-1031 (2004).

U.S. Appl. No. 11/669,093, Office Action mailed Sep. 25, 2008.

U.S. Appl. No. 11/669,093, Notice of Allowance mailed Mar. 10, 2009.

U.S. Appl. No. 11/669,093, Notice of Allowance mailed Dec. 16, 2009.

U.S. Appl. No. 12/030,849, Restriction Requirement mailed May 8, 2009.

U.S. Appl. No. 12/030,849, Non-final Office Action mailed Mar. 5, 2010.

U.S. Appl. No. 12/030,849, Final Rejection mailed Apr. 13, 2011.

U.S. Appl. No. 12/030,849, Advisory Action mailed Aug. 1, 2011.

U.S. Appl. No. 12/865,857, Restriction Requirement mailed Nov. 23, 2011.

\* cited by examiner total AS pSer 129 AS.

GRK Analysis Normalized to Molar Ratio (1:200 kinase: AS)

total AS

GRK Analysis Normalized to Molar Ratio (1:200 kinase: AS)

Phospho S129 AS

Normalized to Activity Units (nmol phosphate into µM synthetic peptide)

total AS

Normalized to Activity Units (nmol phosphate into µM synthetic peptide)

pSer129 AS total AS pSer129 AS pSer87 AS

GRK Analysis Normalized to Molar Ratio (1:200 kinase: AS)

total AS

GRK Analysis Normalized to Molar Ratio (1:200 kinase: AS)

Phospho S129 AS

Total AS    A

Phospho S129 AS    B

Total AS    A

Phospho S87 AS    B

ALPHA-SYNUCLEIN KINASE

RELATED APPLICATIONS

This application claims priority as a divisional of U.S. patent application Ser. No. 12/030,849, filed Feb. 13, 2008, which is a continuation-in-part of U.S. patent application Ser. No. 11/669,093, filed Jan. 30, 2007, which claims benefit of U.S. provisional application No. 60/764,000, filed Jan. 31, 2006, each of which is herein incorporated by reference in its entirety for all purposes.

REFERENCE TO A "SEQUENCE LISTING," A TABLE, OR A COMPUTER PROGRAM LISTING SUBMITTED IN COMPUTER READABLE FORMAT

The Sequence Listing written in file 0-17521US_SEQL-ST.txt is 15,436 bytes, and was created on Feb. 8, 2010, for the application filed herewith, John P. Anderson, et al. "Alpha-Synuclein Kinase." The information contained in this file is hereby incorporated by reference.

BACKGROUND OF THE INVENTION

Lewy body diseases (LBDs) are characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). LBDs include Parkinson's disease, Diffuse Lewy body disease (DLBD), Lewy body variant of Alzheimer's disease (LBV), combined Parkinson's disease (PD) and Alzheimer's disease (AD), and the syndromes identified as multiple system atrophy (MSA). Dementia with Lewy bodies (DLB) is a term coined to reconcile differences in the terminology of LBDs. Disorders with LBs continue to be a common cause for movement disorders and cognitive deterioration in the aging population (Galasko et al., *Clinical-neuropathological correlations in Alzheimer's disease and related dementias. Arch. Neurol.* (1994) 51:888-95). Although their incidence continues to increase, creating a serious public health problem, to date these disorders lack approved treatments (Tanner et al., *Epidemiology of Parkinson's disease and akinetic syndromes, Curr. Opin. Neurol.* (2000) 13:427-30). The cause for LBDs is controversial and multiple factors have been proposed to play a role, including various neurotoxins and genetic susceptibility factors.

In recent years, new hope for understanding the pathogenesis of LBDs has emerged. Specifically, several studies have shown that the synaptic protein alpha-synuclein plays a central role in PD pathogenesis because: (1) this protein accumulates in LBs (Spillantini et al., *Nature* (1997) 388:839-40; Takeda et al., *J. Pathol.* (1998) 152:367-72; Wakabayashi et al., *Neurosci. Lett.* (1997) 239:45-8), (2) mutations in the alpha-synuclein gene co-segregate with rare familial forms of parkinsonism (Kruger et al., *Nature Gen.* (1998) 18:106-8; Polymeropoulos, et al., *Science* (1997) 276:2045-7) and, (3) overexpression of alpha-synuclein in transgenic mice (Masliah et al., *Science* (2000) 287:1265-9) and *Drosophila* (Feany et al., *Nature* (2000) 404:394-8) mimics several pathological aspects of PD.

Many scientists believe that PD is a relatively late development in a systemic synucleinopathy and that "parkinsonism is just the tip of the iceberg" (Langston, *Annals of Neurology* (2006) 59:591-596). For example, Lewy bodies have been described in sympathetic ganglia and in the myenteric plexus of the gut (Herzog E., *Dtch Z Nervenheilk* (1928) 107: 75-80; Kupsky et al., *Neurology* (1987) 37:1253-1255). Various disorders have been associated with the presence of Lewy bodies. For example, Lewy bodies have been found in the brain stem of a patient with rapid eye movement sleep behavioral disorder (Uchiyama et al., *Neurology* (1995) 45:709-712). Olfactory dysfunction has been reported in many PD patients long before the development of parkinsonism. Examination of cardiac tissue from patients with incidental Lewy body disease and typical PD revealed synuclein-positive neuritis in the myocardium (Iwanaga et al., *Neurology* (1999) 52:1269-1271). There is also evidence that esophageal, lower bowel and bladder dysfunction are early manifestations of PD-related pathology in the peripheral autonomic system (Qualman et al., *Gastroenterology* (1984) 87:848-856; Castell et al., *Neurogasdtroenterol Motil* (2001) 13:361-364; Hague et al., *Acta Neuropathol (Berl)* (1997) 94:192-196). Thus, the fact that accumulation of alpha-synuclein in the brain and other tissues is associated with similar morphological and neurological alterations in species as diverse as humans, mice, and flies suggests that this molecule contributes to the development of PD.

BRIEF SUMMARY OF THE INVENTION

In one aspect, the invention provides methods of screening an agent for activity for treating a Lewy Body disease (LBD). Such diseases include Parkinson's disease (PD), Diffuse Lewy body disease (DLBD), Lewy body variant of Alzheimer's disease (LBV), combined PD and Alzheimer's disease (AD), and the syndromes identified as multiple system atrophy (MSA). Some methods entail identifying an agent that modulates the activity or expression of a kinase shown in Table 1A, B; C, Table 2, Table 11 or Table 12, and determining whether the agent shows activity useful in treating LBD in an animal model of the disease. In some methods the modulation is inhibition. In some methods, step (a) involves identifying whether the agent inhibits the kinase. In some methods, step (a) is performed in a cell transformed with a nucleic acid expressing the kinase and/or alpha-synuclein. In some methods, step (a) is performed in vitro. In some methods, step (b) is performed in a transgenic animal model of LBD disease, and the transgenic animal may have a transgene expressing human alpha-synuclein. Preferably, the kinase is at least one of: APEG1, PLK2, CDC7L1, PRKG1, MAPK13, GAK, RHOK, ADRBK1, ADRBK2, GRK2L, GRK5, GRK6, GRK7, IKBKB, CKII and MET and the modulation is inhibition. More preferably, the kinase is PLK2 or GRK6 and the modulation is inhibition. More preferably, the kinase is PLK2. Preferably in some methods, the kinase is PRKG1, MAPK13, or GAK and the modulation is activation. In some aspects, step (b) involves contacting the transgenic animal with the agent and determining whether the agent inhibits formation of deposits of alpha-synuclein relative to a control transgenic animal not treated with the agent.

In another aspect, the invention provides methods of effecting treatment or prophylaxis of a LBD. Some examples of the method involve administering to a patient suffering from or at risk of the disease, an effective regime of an agent effective to modulate activity or expression of a kinase. The kinase can be one of those shown in Table 1A, B or C, Table 2, Table 11 or Table 12. Preferably, the agent is an antibody to the kinase, a zinc finger protein that modulates expression of the kinase, or an antisense RNA, siRNA, ribozyme or RNA having a sequence complementary to a nucleic acid sequence of the kinase. In some methods, the modulation is inhibition, and preferably, the kinase is at least one of the following: APEG1, PLK2, CDC7L1, RHOK, ADRBK1, ADRBK2, GRK2L, GRK5, GRK6, GRK7, IKBKB, CKII and MET. More preferably, the kinase is PLK2 or GRK6. More preferably, the kinase is PLK2. In some of the methods, the kinase is at least one of PRKG1, MAPK13, and GAK, and the modulation is activation.

In one aspect the invention provides method of treating a patient diagnosed with Parkinson's Disease by administering a therapeutically effective amount of an agent that inhibits PLK2 activity. In an embodiment the agent preferentially inhibits PLK2 activity relative to inhibition of PLK1 activity and/or PLK3 activity and/or PLK4 activity. The agent may be, for example, an siRNA. In one embodiment the patient is not diagnosed or under treatment for cancer and/or is not diagnosed or under treatment for Alzheimer's disease.

In related aspects, the invention provides a method for inhibiting phosphorylation of alpha-synuclein in a mammalian cell by reducing polo-like kinase 2 (PLK2) activity in the cell such that phosphorylation of synuclein is reduced. In a related aspect, the invention provides a method for inhibiting phosphorylation of alpha-synuclein in a mammalian cell (e.g., a neuronal cell) by contacting the cell with a compound that reduces PLK2 activity in the cell such that phosphorylation of alpha-synuclein is reduced. For example, the agent may reduce expression of a PLK2 gene product.

In certain embodiments the agent preferentially reduces PLK2 activity relative to reduction of PLK1 activity, PLK2 activity, or PLK3 activity. In certain embodiments the agent has a molecular weight less than 4000. In one embodiment the agent is a synthetic compound. In some embodiments the agent is a polynucleotide that inhibits expression or translation of a PLK2 RNA transcript, such as an siRNA. In an embodiment, one strand of the double stranded region of the siRNA is perfectly complementary to a PLK2 transcript but not to a PLK1 transcript or a PLK3 transcript.

In another aspect, the invention provides methods of identifying a kinase that phosphorylates alpha-synuclein by transfecting a cell expressing alpha-synuclein with a nucleic acid having a sequence complementary to a gene encoding a kinase or zinc finger protein that specifically binds to the gene. The transfected nucleic acid or zinc finger protein inhibits expression of the kinase; and an amount of phosphorylated alpha-synuclein the cell can then be measured relative to a control cell not transfected with the siRNA or nucleic acid encoding the same. In this case, a reduction in phosphorylated alpha-synuclein will provide an indication that the kinase phosphorylates alpha-synuclein. Some methods also include measuring an amount of alpha-synuclein produced by the cell relative to a control cell not transfected with the nucleic acid. In some methods, the nucleic acid is an siRNA or a DNA molecule encoding the same.

The invention provides a method of identifying an agent reduces alpha-synuclein phosphorylation in a mammalian cell expressing alpha-synuclein. The method includes selecting an agent that a) reduces activity of PLK2 in a cell expressing PLK2 (and optionally expressing synuclein), and b) does not reduce activity of PLK1 in a cell expressing PLK1, or reduces activity of PLK1 at a higher $EC_{50}$ than for PLK2; and/or c) does not reduce activity of PLK3 in a cell expressing PLK3, or reduces activity of PLK3 at a higher $EC_{50}$ than for PLK2; and/or d) does not reduce activity of PLK4 in a cell expressing PLK4, or reduces activity of PLK4 at a higher $EC_{50}$ than for PLK2. The cell can be a mammalian cell over-expressing alpha-synuclein. In one embodiment the agent a) reduces activity of PLK2 in a cell expressing PLK2; b) does not reduce activity of PLK1 in a cell expressing PLK1, or reduces activity of PLK1 at a higher $EC_{50}$ than for PLK2; c) does not reduce activity of PLK3 in a cell expressing PLK3, or reduces activity of PLK3 at a higher $EC_{50}$ than for PLK2; and d) does not reduce activity of PLK4 in a cell expressing PLK4, or reduces activity of PLK4 at a higher $EC_{50}$ than for PLK2. In a further step, the method involves determining whether the selected agent shows activity useful in treating Lewy Body Disease in an animal model of the disease or a cellular model of the disease. Animal models include transgenic animals. Cellular models include neuronally-derived cell cultures and mammalian cells over-expressing alpha-synuclein. Activities that can be assayed include reduction of the proportion of total alpha-synuclein that is phosphorylated at serine-129 or a reduction in aggregation of alpha-synuclein in the cell.

In other aspects, the invention provides methods of method of screening an agent for activity for treating a Lewy Body disease (LBD), by identifying an agent that modulates the activity or expression of synphilin, and determining whether the agent shows activity useful in treating LBD in an animal model of the disease.

In other aspects, the invention provides methods for producing Ser-129 phosphorylated-alpha synuclein, by providing a plasmid encoding alpha-synuclein and a plasmid encoding PLK2 in a bacterial cell, culturing the cell so that the plasmids are co-expressing to produce alpha synuclein and PLK2 so that the PLK2 phosphorylates the alpha-synuclein in a bacterial cell, and isolating phosphorylated alpha-synuclein from the cell.

BRIEF DESCRIPTION OF THE DRAWINGS

FIG. 1A shows total alpha-synuclein, FIG. 1B shows phosphorylation of the pser-129 (phospho-serine-129) of alpha-synuclein and FIG. 1C shows phosphorylation of the pser-87 (phospho-serine-87) of alpha-synuclein.

FIG. 1D shows total alpha-synuclein, FIG. 1E shows phosphorylation of the pser-129 of alpha-synuclein and FIG. 1F shows phosphorylation of the pser-87 of alpha-synuclein.

FIG. 2A shows the total (AS).

FIG. 2A shows the total AS. FIG. 3B shows Serine 129. FIG. 3C shows phospho-serine 87.

FIG. 4A shows the total AS.

DETAILED DESCRIPTION OF THE INVENTION

I. Definitions

Figure 1A:
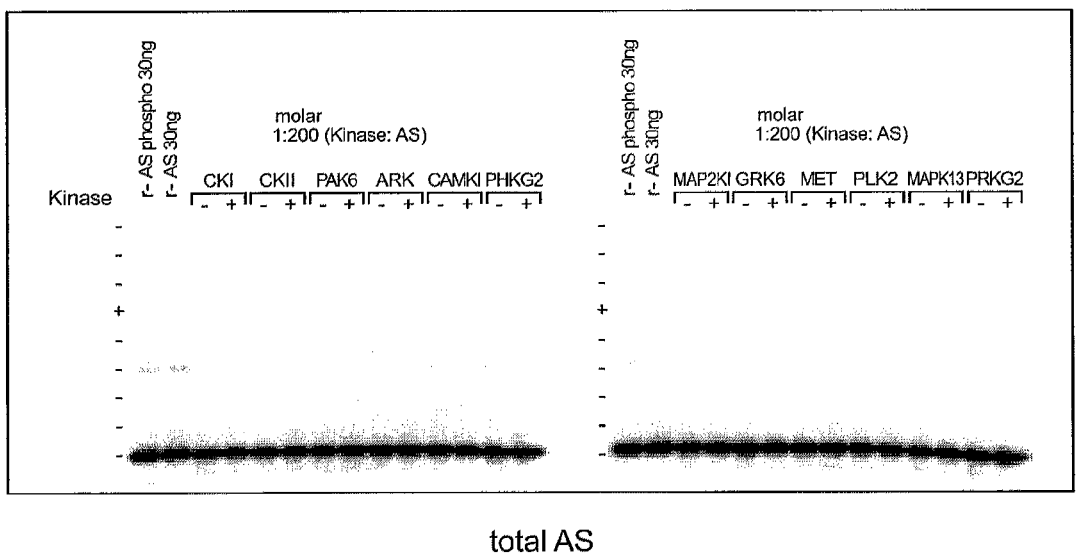
FIGS. 1A-C show the results of the in vitro phosphorylation assay for alpha-synuclein phosphorylation by a variety of recombinant kinases.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A Lewy-like body is a deposit of alpha-synuclein found in a transgenic animal that resembles some or all of the characteristics of a Lewy body found in human patients. The preferred characteristics are a compact alpha-synuclein positive inclusion. These inclusions preferably form in an age-dependent manner. The formation of alpha-synuclein positive inclusions preferably results in observable cellular pathology, leading to loss of functionality of affected neurons. Loss of function of affected neurons can be determined through behavioral tests, neuropharmacological response evaluation and electrophysiology.

The phrase "specifically binds" refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule such as an antibody that specifically binds to a protein often has an association constant of at least $10^6 M^{-1}$ or $10^7 M^{-1}$, preferably $10^8 M^{-1}$ to $10^9 M^{-1}$, and more preferably, about $10^{10} M^{-1}$ to $10^{11} M^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for examples of immunoassay formats and conditions that can be used to determine specific immunoreactivity.

For sequence comparison, typically one sequence acts as a reference sequence, to which test sequences are compared. When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, $M=5$, $N=-4$, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For purposes of classifying amino acids substitutions as conservative or non-conservative, amino acids are grouped as follows: Group I (hydrophobic side chains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least about 90%, at least about 95%, or at least about 99% w/w purity. However, using conventional protein purification techniques, homogeneous peptides of at least 99% w/w can be obtained.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A symptom of a disorder means a phenomenon experienced by an individual having the disorder indicating a departure from normal function, sensation or appearance.

A sign of a disorder is any bodily manifestation that serves to indicate presence or risk of a disorder.

The term "patient" includes human and other mammalian subjects that receive either prophylactic or therapeutic treatment.

As used herein, "treating" a condition (e.g., Parkinson's Disease) or patient refers to taking steps to obtain beneficial or desired result. For purposes of this invention, beneficial or desired results include, but are not limited to, alleviation or amelioration of one or more symptoms of Parkinson's Disease, diminishment of extent of disease, delay or slowing of disease progression, amelioration, palliation or stabilization of the disease state.

As used herein, a "therapeutically effective amount" of a drug is an amount of a drug that, when administered to a subject diagnosed with Parkinson's disease, or diagnosed as being at high risk for developing Parkinson's disease will have the intended therapeutic effect, e.g., alleviation, amelioration, palliation or elimination of one or more manifestations of the disease in the subject. The full therapeutic effect does not necessarily occur by administration of one dose, and may occur only after administration of a series of doses. Thus, a therapeutically effective amount may be administered in one or more administrations.

Compositions or methods "comprising" one or more recited elements may include other elements not specifically recited. For example, a composition that comprises alpha-synuclein peptide encompasses both an isolated alpha-synuclein peptide and alpha-synuclein peptide as a component of a larger polypeptide sequence.

Unless otherwise apparent from the context, each embodiment, element, step or feature of the invention can be used in combination with any other.

II. General

The invention is premised in part on the insight that Lewy Body diseases (LBDs) can be inhibited by inhibiting one or more kinases that phosphorylate alpha-synuclein and/or inhibit its production. Although practice of the invention is not dependent on an understanding of mechanism, it is believed that phosphorylation of alpha-synuclein at serine-129 is one of a series of molecular events leading to formation of intracellular deposits of alpha-synuclein. Alpha-synuclein phosphorylated at ser-129 is highly enriched in Lewy bodies (LBs) in Diffuse Lewy body disease (DLBD), multiple system atrophy (MSA) and familial forms of Parkinson's Disease (PD). The abnormal accumulation of phospho-alpha-synuclein in LBs indicates that phospho-synuclein may be a pathogenic species that drives LB formation, and that the kinase(s) responsible for its phosphorylation or which regulates production of alpha-synuclein itself are therapeutic target(s) for treatment of multiple synucleinopathies. Other events in this series likely include proteolytic cleavages following phosphorylation (see WO 2005/013889, filed May 19, 2004).

Identification of the kinase(s) primarily responsible for phosphorylation of alpha-synuclein allows compounds that reduce activity of the relevant kinase(s) to be identified. For convenience, reference herein to "phosphorylation of alpha-synuclein" refers to phosphorylation at Serine-129 (but does not exclude additional phosphorylation elsewhere, e.g., Serine-87).

The present application reports identification of several kinases where reduction in kinase activity is accompanied by a reduction of phosphorylation of alpha-synuclein and/or a reduction in total alpha-synuclein level. In particular, the kinase PLK2 can be inhibited to reduce phosphorylation of alpha-synuclein. The invention provides methods of (i) identifying modulators of the activity and expression of these kinases, (ii) methods of treating Lewy body diseases using kinase inhibitors, and (iii) exemplary kinase inhibitors for use in treating Lewy body diseases.

As discussed in the Examples, infra, we have carried out a variety of experiments to identify kinases important in phosphorylation of alpha-synuclein. Section III outlines a strategy for identifying alpha-synuclein kinases. Section IV summarizes results of screening assays used to identify likely alpha-synuclein kinases. Section V describes agents that reduce synuclein kinase activity or expression and may be used therapeutically. Section VI describes methods for treating Parkinson's Disease and other Lewy Body Diseases. Section VII describes Lewy Body Diseases. Section VIII describes transgenic animal and cellular models of Lewy Body Disease. Section IX describes method for identification of modulators of PLK2 and other kinases. Section X describes methods for alpha-synuclein isolation. Section XI provides experimental results including the aforementioned screening assays.

III. Identification of Target Kinases

Kinases that directly or indirectly modulate phosphorylation of alpha-synuclein can be identified as shown in the Examples. In general, a library of potential inhibitors is designed based on the known sequences of a collection of kinase genes. The members of the library can be any of the types of molecule described above. Members of the library are then introduced into cells expressing alpha-synuclein. Preferably both the cells and the alpha-synuclein are human. Usually, such cells are transfected with both DNA encoding human alpha-synuclein and DNA encoding the library member to be tested. Library members can be screened individually or en masse. After introduction of a library member, and culturing for a period sufficient for the library member to be expressed and effect repression of its kinase, the levels of total alpha-synuclein and phosphorylated alpha-synuclein are measured and compared with corresponding levels in an otherwise similar control cell not treated with a library member to suppress expression of a kinase. Measurements can be made by immunoassay using an antibody specific for alpha-synuclein (preferably human alpha-synuclein) to measure total levels of alpha-synuclein, and an antibody specific for phosphorylated alpha-synuclein to measure the level of phosphorylated alpha-synuclein. Exemplary antibodies are described in WO05047860, incorporated herein by reference. A reduction in level of phosphorylated alpha-synuclein between the treated and control cell that is significant in the sense of being outside the typical margin of error for measurements, indicates that the inhibitor introduced into the cell inhibited a kinase, which directly or indirectly affected phosphorylation of alpha-synuclein. The identity of the kinase can be determined from the identity of inhibitor, either by screening inhibitors individually, or if inhibitors are screened en masse, by sequencing the nucleic acid encoding the inhibitor. Likewise a reduction in the total level of alpha-synuclein between treated and control cells that is outside the margin of typical experimental error in measuring such levels provides an indication that the inhibitor inhibits a kinase that indirectly affects the expression level of alpha-synuclein.

Kinases identified by the initial screen, particularly, kinases known to be serine kinases, can then be tested for their capacity to phosphorylate alpha-synuclein in vitro, in cells or in transgenic animal models. An in vitro assay is an indication of whether a kinase directly phosphorylates alpha-synuclein and is therefore only useful for the kinases identified in the initial screen which are thought to be capable of directly phosphorylating alpha-synuclein. Cellular and transgenic assays can be used to screen kinases that affect phosphorylation either directly or indirectly. In vitro assays may be performed by contacting alpha-synuclein with the kinase under test and ATP in a suitable buffer. Preferably, the ATP is γ-32P ATP, in which case phosphorylated alpha-synuclein is radiolabeled and can be detected on a gel. Phosphorylation can also be measured using an antibody specific to phosphorylated alpha-synuclein as described before. Alternatively, phosphorylation can be measured indirectly by measuring ATP consumption using a coupled assay, in which ADP is detected as described for example by *Nature* 78, 632 (1956); *Mol. Pharmacol.* 6, 31-40 (1970). The extent of phosphorylation can be compared with a control in which the kinase or ATP or both is/are omitted. An increase in phosphorylation is an indication that the kinase directly phosphorylates alpha-synuclein. Cellular assays are performed on cells expressing alpha-synuclein, preferably human alpha-synuclein transfected into the cells. A nucleic acid capable of expressing the kinase is also transfected into the cells. The level of phosphorylated alpha-synuclein in the cells is measured relative to that in similar control cells lacking the transfected kinase. An increase in phosphorylation is an indication that the kinase directly or indirectly phosphorylates alpha-synuclein. Transgenic assays can be performed by comparing a transgenic animal expressing human alpha-synuclein disposed to develop Lewy body-like deposits with a similar animal also expressing a kinase transgene. A reduction in phosphorylated alpha-synuclein and/or in Lewy body-like deposits in the transgenic animal with the additional kinase transgene relative to the transgenic animal with just the alpha-synuclein transgene is an indication that the kinase is directly or indirectly involved in phosphorylating alpha-synuclein.

IV. Target Kinases

Tables 1A, 1B and 1C show proteins whose inhibition modulates the phosphorylation at position ser-129. Table 1A shows kinases that can phosphorylate serine and/or threonine residues and sometimes tyrosine. Table 1B shows tyrosine kinases that cannot (so far as is known) modify serine residues. Table 1C shows kinases that phosphorylate non-protein targets but are not known to phosphorylate proteins. Kinases from the upper portion of Table 1A are candidates for direct phosphorylation of ser-129 of alpha-synuclein. Kinases from the upper part of Table 1B are also useful therapeutic targets via roles indirectly phosphorylating alpha-synuclein. Proteins in the upper part of Table 1C are also useful therapeutic targets for the same reason. Cols. 1, 2 and 3 of each table indicate the gene name, kinase name and Genbank accession number of kinases. The next column indicates whether treatment of cells with siRNA to that kinase decreased ("down") or increased ("up") phosphorylation of ser-129. The next three columns indicate the number of standard deviations the measured level of phosphorylation departs from the mean in three independent experiments. The final two columns indicate the kinase family (i.e., amino acid specificity) and group.

Table 2 shows kinases whose inhibition modulates the overall levels of human alpha-synuclein without changing the percentage of phosphorylation. Table 2 shows all of the kinases with the strongest reduction in levels of human alpha-synuclein. The columns are labeled similarly to Tables 1A, 1B and 1C.

Tables 3 and 4 show kinases from Tables 1 and 2 that were confirmed in the Examples to modulate overall levels of human alpha-synuclein. The kinases that were verified include PLK2, APEG1, CDC7L1, MET, GRK1, 2, 6, and 7 as kinases that phosphorylate alpha-synuclein directly or indirectly. The kinases that were found to increase alpha-synuclein phosphorylation when inhibited, PRKG1, MAPK13, and GAK, are likely to function as negative regulators of alpha-synuclein phosphorylation. Further data from phosphorylation studies in vitro identified PKL2, GRK2, 5, 6, and 7 as capable of phosphorylating alpha-synuclein in vitro and also identified CKII and IKBKB. Further studies in cell culture showed that PLK2 and GPRK6 could directly phosphorylate alpha-synuclein in cell culture. These data were substantiated with immunohistochemistry. In summary, PLK2 and, to a lesser extent, GRK6 are particularly preferred targets for therapeutic intervention in Lewy body diseases because they can directly phosphorylate alpha-synuclein. Agents that inhibit PLK2 and GRK6 also inhibit phosphorylation of alpha-synuclein and thus can be used in treatment or prophylaxis of Lewy body disease.

In the Examples, below, transfection of cells with siRNA and knockdown of specific kinase targets was employed to identify kinases that modulated alpha-synuclein phosphorylation directly or indirectly. Subsequent experiments in vitro and in cell culture showed that two of these kinases, PLK2 directly and specifically phosphorylated the serine 129 of alpha-synuclein. Further experiments showed that PLK2 phosphorylated the serine 129 of alpha-synuclein to a much greater extent than GRK6 and other kinases described herein under the experimental conditions used. Thus, PLK2 is very likely a synuclein kinase. Additional evidence that PLK2 is a synuclein kinase is provided in Examples 11-16. Synuclein phosphorylation is reduced in cells treated with siRNA directed to PLK2, inhibitors of PLK2 activity reduce synuclein phosphorylation in a variety of cell types including primary neuronal cultures and cells over expressing PLK2, inhibitors affect endogenous kinase in with an $EC_{50}$ consistent with the $EC_{50}$ observed for their effect on PLK2.

PLK2 is a Polo like kinase that is a G1 cell cycle protein, has a rapid turnover in cells, and is expressed in brain where it is involved in synaptic plasticity. The PLK family members are serine/threonine kinases, and contains four members that have an N-terminal kinase domain and a C-terminal regulatory domain consisting of two (PLKs 1-3) or one (PLK4) polo-box domains. The polo-box domain serves to bind to scaffolding proteins that then target the PLKs to specific sub-cellular locations and to phosphorylate their target proteins (Seeburg, D. P. et al, Oncogene, 2005). The polo-box also serves to negatively regulate the kinase domain by adopting a conformation that prevents kinase activity. Upon binding of the polo-box to a scaffolding protein, the polo-box is removed from the kinase domain, whereupon the kinase becomes active and is able to phosphorylate its substrate/s. Polo-like kinases are described in Seeburg et al., 2005, "Polo-like kinases in the nervous system" Oncogene 24:292-8; Lowery et al., 2005, "Structure and function of Polo-like kinases" Oncogene 24:248-59; and Winkles et al., 2005, "Differential regulation of polo-like kinase 1, 2, 3, and 4 gene expression in mammalian cells and tissues" Oncogene 24:260-6. DNA and protein sequences can be found at the accession numbers below:

| Kinase | GenBank Accession number | Entrez Gene ID | UniProt ID |
|---|---|---|---|
| PLK1 | NM_005030 | 5347 | P53350 |
| PLK2 | NM_006622 | 10769 | Q9NYY3 |
| PLK3 | AJ293866, NM_004073 | 1263 | Q9H4B4 |
| PLK4 | Y13115, NM_014264 | 10733 | O00444 |

When PLK2 is activated, it is targeted to dendrites of activated neurons, where it is believed to phosphorylate proteins in the synaptic terminals. An exemplary accession number for PLK2 is provided Table 1A. The sequence for PLK2 can also be found in any one of Ma, et al. *Mol. Cell. Biol.* 23 (19), 6936-6943 (2003), Burns, et al. *Mol. Cell. Biol.* 23 (16), 5556-5571 (2003), Matsuda, et al. *Oncogene* 22 (21), 3307-3318 (2003), Shimizu-Yoshida et al. *Biochem. Biophys. Res. Commun.* 289 (2), 491-498 (2001), Liby, et al. *DNA seq.* 11 (6), 527-533 (2001), Holtrich, et al. *Oncogene* 19 (42), 4832-4839, Ouyang, et al. *Oncogene* 18 (44), 6029-6036 (1999), and Kauselmann, et al. *EMBO J.* 18 (20), 5528-5539; reference to an amino acid or nucleic acid sequence of PLK2 includes the sequences of any of these references or allelic variants thereof. PLK2 is also called SNK; for consistency, the name PLK2 is used throughout the present patent application.

APEG1, CDC7L1, MET, IKBKB, CKII, GRK1, GRK2, GRK6 and GRK7 are also targets for therapeutic intervention in Lewy body diseases because they are likely to be indirect activators of the direct kinase(s). Thus, agents that inhibit APEG1, CDC7L1, MET, IKBKB, CKII, GRK1, GRK2, GRK6 and GRK7 also inhibit phosphorylation of alpha-synuclein and can be used for treatment or prophylaxis of Lewy body disease. PRKG1, MAPK13, and GAK are negative regulators of the phosphorylation of alpha-synuclein. Thus, agents that activate these kinases decrease phosphorylation of alpha-synuclein and can be used in treatment or prophylaxis of Lewy body disease.

GRK6, also called GPRK6, is a G protein-coupled receptor kinase and is involved in signal transduction. G protein-coupled receptor kinases phosphorylate and desensitize ligand-activated G protein-coupled receptors. GRK6 expression has previously been shown to be significantly elevated in the MPTP-lesioned group in most brain regions. For the purposes of consistency, the name GRK6 will be used throughout the present patent application. An exemplary accession number is provided in Table 1A. The sequence for GRK6 can be found in any one of Teli, et al., *Anesthesiology* 98 (2), 343-348 (2003); Miyagawa, et al., *Biophys. Res. Commun.* 300 (3), 669-673 (2003); Gaudreau, et al., *J. Biol. Chem.* 277 (35), 31567-31576 (2002); Grange-Midroit, et al., *Brain Res. Mol. Brain Res.* 101 (1-2), 39-51 (2002); Willets, et al., *J. Biol. Chem.* 277 (18), 15523-15529 (2002); Blaukat, et al., *J. Biol. Chem.* 276 (44), 40431-40440 (2001); Zhou, et al., *J. Pharmacol. Exp. Ther.* 298 (3), 1243-1251 (2001); Pronin, et al., *J. Biol. Chem.* 275 (34), 26515-26522 (2000); Tiruppathi, *Proc. Natl. Acad. Sci. U.S.A.*, 97 (13), 7440-7445 (2000); Premont, et al. *J. Biol. Chem.*, 274 (41), 29381-29389 (1999); Brenninkmeijer, et al., *J. Endocrinol.* 162 (3), 401-408 (1999); Hall, et al., *J. Biol. Chem.* 274 (34), 24328-24334 (1999); Lazari, et al., *Mol. Endocrinol.* 13 (6), 866-878 (1999); Milcent, et al., *Biochem. Biophys. Res. Commun.* 259 (1), 224-229 (1999); Premont, *Proc. Natl. Acad. Sci. U.S.A.* 95 (24), 14082-14087 (1998); Stoffel, et al., *Biochemistry* 37 (46), 16053-16059 (1998); Loudon, et al., *J. Biol. Chem.* 272 (43), 27422-27427 (1997); Freedman, et al., *J. Biol. Chem.* 272 (28), 17734-17743 (1997); Bullrich, et al., *Cytogenet. Cell Genet.* 70 (3-4), 250-254 (1995); Stoffel, et al.; *J. Biol. Chem.* 269 (45), 27791-27794 (1994); Loudon, et al., *J. Biol. Chem.* 269 (36), 22691-22697 (1994); Haribabu and Snyderman, *Proc. Natl. Acad. Sci. U.S.A.* 90 (20), 9398-9402 (1993); and Benovic and Gomez, *J. Biol. Chem.* 268 (26), 19521-19527 (1993); reference to the amino acid or nucleic acid sequence of GRK6 includes the amino acid or nucleic acid sequence of any of these references and allelic variants thereof.

Casein kinase 2 (also called Casein kinase II, CKII, CSNK2 and CSNKII) has been reported to phosphorylate alpha-synuclein. For consistency, the name CKII will be used herein. The sequence for CKII has been provided in Genbank under the following accession numbers: NM_001896, NM_001320 and/or can be found in any one of Panasyu, et al. *J. Biol. Chem.* 281 (42), 31188-31201 (2006); Salvi, et al. *FEBS Lett.* 580 (16), 3948-3952 (2006); Lim et al. *Cell* 125 (4), 801-814 (2006); Llorens, et al. *Biochem. J.* 394 (Pt. 1), 227-236, (2006); Bjorling-Poulsen, et al. *Oncogene* 24 (40), 6194-6200 (2005); Schubert, et al. *Eur. J. Biochem.* 204 (2), 875-883 (1991); Voss, et al. *J. Biol. Chem.* 266 (21), 13706-13711 (1991); Yang-Feng, et al. *Genomics* 8 (4), 741-742 (1990); Heller-Harrison, et al. *Biochemistry* 28 (23), 9053-9058 (1989); Ackermann, et al. *Mol. Cell. Biochem.* 274 (1-2), 91-101 (2005); Barrios-Rodiles, et al. *Science* 307 (5715), 1621-1625 (2005); Andersen, et al. *Nature* 433 (7021), 77-83 (2005); Ballif, et al. *Mol. Cell. Proteomics,* 3 (11), 1093-1101 (2004); Beausoleil, et al. *PNAS, USA* 101 (33), 12130-12135 (2004); Marais, et al. *EMBO J.* 11 (1), 97-105 (1992). Reference to the amino acid or nucleic acid sequence of CKII includes the amino acid or nucleic acid sequence of any of these references and allelic variants thereof.

IKBKB and the related IKBKA are positive regulators of the NFkB inflammatory pathway. The sequence for IKBKB has been provided in Genbank under the following accession number: NM_001556 and/or can be found in any one of: Caterino, et al. *FEBS Lett.* 580 (28-29), 6527-6532 (2006); Castle, et al. *Genome Biol.* 4 (10), R66 (2003); Satoh, et al.

Biochim, Biophys. Acta 1600 (103), 61-67 (2002), Caohuy, and Pollard, *J. Biol. Chem.* 277 (28), 25217-25225 (2002); Yu, et al. *J. Biol. Chem.* 277 (18), 15819-15827 (2002); Selbert, et al. *J. Cell. Sci.* 108 (Pt. 1), 85095 (1995); Shirvan, et al. *Biochemistry* 33 (22), 6888-6901 (1994); Creutz, et al. *Biochem. Biophys. Res. Commun.* 184 (1), 347-352 (1992); Megendzo, et al. *J. Biol. Chem.* 266 (5), 3228-3232 (1991); Burns, et al. *PNAS, USA* 86 (10), 3798-3802 (1989). Reference to the amino acid or nucleic acid sequence of IKBKB includes the amino acid or nucleic acid sequence of any of these references and allelic variants thereof.

Synphilin is a synuclein-associated protein that has been shown to bind alpha-synuclein. Although not a kinase itself, Synphilin was found herein to promote phosphorylation of synuclein particularly in combination with PLK2. The synphilin appeared to promote phosphorylation of synuclein in a PLK2-dependent manner. The sequence for synphilin has been provided in Genbank under the following accession number: NM_005460 and/or can be found in any one of: Tanji, et al. Am. J. Pathol. 169 (2), 553-565 (2006); Eyal, et al. *PNAS, USA* 103 (15), 5917-5922 (2006); Avraham, et al. *J. Biol. Chem.* 280 (52), 42877-42886 (2005); Bandopadhyay, et al. *Neurobiol. Dis.* 20 (2), 401-411 (2005); Lim et al. *J. Neurosci.* 25 (8), 2002-2009 (2005); Ribeiro, et al. *J. Biol. Chem.* 277 (26), 23927-23933 (2002); Chung, et al. *Nat. Med.* 7 (10), 1144-1150 (2001); Engelender, et al. *Mamm. Genome* 11 (9), 763-766 (2000); Engelender, et al. *Nat. Genet.* 22 (1), 110-114 (1999). Reference to the amino acid or nucleic acid sequence of synphilin includes the amino acid or nucleic acid sequence of any of these references and allelic variants thereof.

V. Agents to Modulate Synuclein Kinase Activity or Expression

In one aspect, the invention provides methods of effecting treatment or prophylaxis of an LBD by administering an agent that modulates activity or expression of a kinase described herein. A number of agents of well-characterized general classes can be used. Without limitation these include inhibitory nucleic acids (e.g., siRNA, antisense RNA, ribozymes), inhibitory proteins (e.g., zinc finger proteins), antibodies, and small molecule inhibitors.

Preferably the gene to be inhibited is PLK2 or GRK6 because the kinases encoded by these genes directly phosphorylate alpha-synuclein, and particularly PLK2. APEG1, CDC7L1, MET GRK1, GRK2, GRK6, IKBKB, CKII and GRK7 genes are also preferred targets for inhibition because they are likely to encode indirect activators of the direct kinase(s). PRKG1, MAPK13, and GAK are preferred candidates for activation in Lewy body diseases because they encode negative regulators of the phosphorylation of alpha-synuclein. The synphilin gene is a preferred target for inhibition because, although synphilin is not a kinase, it is associated with increased phosphorylation of alpha-synuclein (typically in the presence of a kinase such as PLK2).

Inhibitors that show specificity for PLK2 over one or more other polo-like kinase family members (i.e., PLK1, PLK3, and PLK4) are preferred. Inhibitors especially suited for therapeutic use may be identified by selecting for at least one of the following properties:
  I. Inhibits PLK2 activity and has no, or reduced, effect on PLK1.
  II. Inhibits PLK2 activity and has no, or reduced, effect on PLK3.
  III. Inhibits PLK2 activity and has no, or reduced, effect on PLK4.
  IV. Inhibits PLK2 activity and has no, or reduced, effect on PLK1 and PLK3.
  V. Inhibits PLK2 activity and has no, or reduced, effect on PLK1 and PLK4.
  VI. Inhibits PLK2 activity and has no, or reduced, effect on PLK1, PLK3 and PLK4.

As used in this context, "no effect" means administration of the agent does not reduce expression, or reduces expression by a physiologically insignificant degree. "Reduced effect" means that the $EC_{50}$ or $K_i$ values for inhibiting PLK2 is lower than the $EC_{50}$ for the reference PLK(s). In some embodiments the $EC_{50}$ may be at least 2-fold lower, and is sometimes at least 10-fold lower, and may be at least 100-fold, or even at least 1000-fold lower.

As used in this context, inhibition of PLK2 "activity" can result from reducing protein expression (e.g., reducing expression of the PLK2 gene, interfering with processing of PLK2 RNA, reducing the half-life of PLK2 mRNA or protein) or by competitive or noncompetitive inhibition of the PLK2 kinase activity.

Inhibitors that show specificity for PLK2 over non-polo kinases, especially other kinases expressed in the tissues to which the agent is delivered are especially preferred. In preferred embodiments the agent does not inhibit non-polo kinases (or has a $EC_{50}$ greater than 10-times higher, sometimes 100-times greater, and sometimes greater than 1000-times higher) for non-polo kinases compared to PLK2. However, inhibition of other kinases may be tolerated depending on the role and expression of the kinase. For example, a kinase that functions in the gut may not be affected by an inhibitor delivered to the brain.

To further guide the reader, inhibitory nucleic acids (e.g., siRNA, antisense RNA, ribozymes), inhibitory proteins (e.g., zinc finger proteins), antibodies, and small molecule inhibitors are discussed below.

A. Inhibitory Polynucleotides

Several examples of inhibitors of target kinases, including PLK2, are described below. Polynucleotide inhibitors are designed to bind specific target sequences within a target transcript. Preferably the inhibitors bind to a target site in a PLK2 RNA without binding a target site in: PLK1 and/or PLK3 and/or PLK4. Suitable target sites are identified by selecting segments of PLK2 that have no exact corresponding segment in other PLKs. Preferably, a selected segment of PLK2 lacks a corresponding segment having substantial sequence identity (for example, a selected segment from PLK2 should show less than 95, 90, 75 or 50% sequence identity with the closest corresponding segment in PLK4). A selected target segment is also preferably screened against a gene database to ensure that it does not show significant sequence identity with unrelated genes by chance.

Polynucleotide inhibitors of PLK2 preferably show at least 30, 50, 75, 95, or 99% inhibition of levels of PLK2 mRNA or protein with little or no detectable reduction in levels of PLK1 and/or PLK3 and/or PLK4 mRNA or protein (i.e, less than 10, 5 or 1% inhibition). Protein expression can be quantified by forming immunological analyses using an antibody that specifically binds to the protein followed by detection of complex formed between the antibody and protein. mRNA levels can be quantified by, for example, dot blot analysis, in-situ hybridization, RT-PCR, quantitative reverse-transcription PCR (i.e., the so-called "TaqMan" methods), Northern blots and nucleic acid probe array methods.

i) Short Inhibitory RNAs siRNAs are relatively short, at least partly double stranded, RNA molecules that serve to inhibit expression or translation of a complementary mRNA transcript, such as a kinase transcript. Although an understanding of mechanism is not required for practice of the invention, it is believed that siRNAs act by inducing degradation of a complementary mRNA transcript. Principles for design and use of siRNAs generally are described by WO 99/32619, Elbashir, *EMBO J.* 20, 6877-6888 (2001) and Nykanen et al., *Cell* 107, 309-321 (2001); WO 01/29058. siRNAs are formed from two strands of at least partly complementary RNA, each strand preferably of 10-30, 15-25, or 17-23 or 19-21 nucleotides long. The strands can be perfectly complementary to each other throughout their length or can have single stranded 3'-overhangs at one or both ends of an otherwise double stranded molecule. Single stranded overhangs, if present, are usually of 1-6 bases with 1 or 2 bases being preferred. The antisense strand of an siRNA is selected to be substantially complementary (e.g., at least 80, 90, 95% and preferably 100% complementary) to a segment of a transcript from a gene of the invention. Any mismatched bases preferably occur at or near the ends of the strands of the siRNA. Mismatched bases at the ends can be deoxyribonucleotides. The sense strand of an siRNA shows an analogous relationship with the complement of the segment of the gene transcript of interest. siRNAs having two strands, each having 19 bases of perfect complementarity, and having two unmatched bases at the 3' end of the sense strand and one at the 3' end of the antisense strand are particularly suitable.

If an siRNA is to be administered as such, as distinct from the form of DNA encoding the siRNA, then the strands of an siRNA can contain one or more nucleotide analogs. The nucleotide analogs are located at positions at which inhibitor activity is not substantially affected, e.g. in a region at the 5'-end and/or the 3'-end, particularly single stranded overhang regions. Preferred nucleotide analogues are sugar- or backbone-modified ribonucleotides. Nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8 position, e.g. 8-bromo guanosine; deaza nucleotides, e.g. 7-deaza-adenosine; O- and N-alkylated nucleotides, e.g. N6-methyl adenosine are also suitable. In preferred sugar-modified ribonucleotides, the 2' OH-group is replaced by a group selected from H, OR, R, halo, SH, SR, NH2, NHR, NR2 or CN, wherein R is C1-C6 alkyl, alkenyl or alkynyl and halo is F, Cl, Br or I. In preferred backbone-modified ribonucleotides the phosphoester group connecting to adjacent ribonucleotides is replaced by a modified group, e.g. of phosphothioate group. A further preferred modification is to introduce a phosphate group on the 5' hydroxide residue of an siRNA. Such a group can be introduced by treatment of an siRNA with ATP and T4 kinase. The phosphodiester linkages of natural RNA can also be modified to include at least one of a nitrogen or sulfur heteroatom. Modifications in RNA structure can be tailored to allow specific genetic inhibition while avoiding a general panic response in some organisms which is generated by dsRNA. Likewise, bases can be modified to block the activity of adenosine deaminase.

One example of such an agent is siRNA specific for PLK2. siRNAs to the gene encoding PLK2 can be specifically designed using methods described below. An exemplary accession number for PLK2 is [NM_006622] as provided in Table 1A. The amino acid sequence of human PLK2 is also set forth as SEQ ID NO:2 and SEQ ID NO:1 is the nucleic acid sequence encoding the amino acid sequence. For convenience exemplary sequences are provided below.

```
Human PLK2
                                                                  (SEQ ID NO: 1)
   1 gcacaagtgg accggggtgt tgggtgctag tcggcaccag aggcaagggt gcgaggacca 61 cggccggctc ggacgtgtga ccgcgcctag ggggtggcag cgggcagtgc ggggcggcaa 121 ggcgaccatg gagcttttgc ggactatcac ctaccagcca gccgccagca ccaaaatgtg 181 cgagcaggcg ctgggcaagg gttgcggagc ggactcgaag aagaagcggc cgccgcagcc 241 ccccgaggaa tcgcagccac ctcagtccca ggcgcaagtg cccccggcgg cccctcacca 301 ccatcaccac cattcgcact cggggccgga gatctcgcgg attatcgtcg accccacgac 361 tgggaagcgc tactgccggg gcaaagtgct gggaaagggt ggctttgcaa aatgttacga 421 gatgacagat ttgacaaata acaaagtcta cgccgcaaaa attattcctc acagcagagt 481 agctaaacct catcaaaggg aaaagattga caaagaaata gagcttcaca gaattcttca 541 tcataagcat gtagtgcagt tttaccacta cttcgaggac aaagaaaaca tttacattct 601 cttggaatac tgcagtagaa ggtcaatggc tcatattttg aaagcaagaa aggtgttgac 661 agagccagaa gttcgatact acctcaggca gattgtgtct ggactgaaat accttcatga 721 acaagaaatc ttgcacagag atctcaaact agggaacttt tttattaatg aagccatgga 781 actaaaagtt ggggacttcg gtctggcagc caggctagaa cccttggaac acagaaggag 841 aacgatatgt ggtaccccaa attatctctc tcctgaagtc ctcaacaaac aaggacatgg 901 ctgtgaatca gacatttggg ccctgggctg tgtaatgtat acaatgttac tagggaggcc 961 cccatttgaa actacaaatc tcaaagaaac ttataggtgc ataagggaag caaggtatac 1021 aatgccgtcc tcattgctgg ctcctgccaa gcacttaatt gctagtatgt tgtccaaaaa 1081 cccagaggat cgtcccagtt tggatgacat cattcgacat gactttttttt tgcagggctt
```

-continued

```
1141 cactccggac agactgtctt ctagctgttg tcatacagtt ccagatttcc acttatcaag 1201 cccagctaag aatttcttta agaaagcagc tgctgctctt tttggtggca aaaaagacaa 1261 agcaagatat attgacacac ataatagagt gtctaaagaa gatgaagaca tctacaagct 1321 taggcatgat ttgaaaaaga cttcaataac tcagcaaccc agcaaacaca ggacagatga 1381 ggagctccag ccacctacca ccacagttgc caggtctgga acaccagcag tagaaaacaa 1441 gcagcagatt ggggatgcta ttcggatgat agtcagaggg actcttggca gctgtagcag 1501 cagcagtgaa tgccttgaag acagtaccat gggaagtgtt gcagacacag tggcaagggt 1561 tcttcgggga tgtctggaaa acatgccgga agctgattgc attcccaaag agcagctgag 1621 cacatcattt cagtgggtca ccaaatgggt tgattactct aacaaatatg ctttgggta 1681 ccagctctca gaccacaccg tcggtgtcct tttcaacaat ggtgctcaca tgagcctcct 1741 tccagacaaa aaaacagttc actattacgc agagcttggc caatgctcag ttttcccagc 1801 aacagatgct cctgagcaat ttattagtca agtgacggtg ctgaaatact tttctcatta 1861 catggaggag aacctcatgg atggtggaga tctgcctagt gttactgata ttcgaagacc 1921 tcggctctac ctccttcagt ggctaaaatc tgataaggcc ctaatgatgc tctttaatga 1981 tggcaccttt caggtgaatt tctaccatga tcatacaaaa atcatcatct gtagccaaaa 2041 tgaagaatac cttctcacct acatcaatga ggataggata tctacaactt tcaggctgac 2101 aactctgctg atgtctggct gttcatcaga attaaaaaat cgaatggaat atgccctgaa 2161 catgctctta caaagatgta actgaaagac ttttcgaatg gaccctatgg gactcctctt 2221 ttccactgtg agatctacag ggaagccaaa agaatgatct agagtatgtt gaagaagatg 2281 gacatgtggt ggtacgaaaa caattcccct gtggcctgct ggactggttg gaaccagaac 2341 aggctaaggc atacagttct tgactttgga caatccaaga gtgaaccaga atgcagtttt 2401 ccttgagata cctgttttaa aaggtttttc agacaatttt gcagaaaggt gcattgattc 2461 ttaaattctc tctgttgaga gcatttcagc cagaggactt tggaactgtg aatatacttc 2521 ctgaagggga gggagaaggg aggaagctcc catgttgttt aaaggctgta attggagcag 2581 cttttggctg cgtaactgtg aactatggcc atatataatt tttttttcatt aatttttgaa 2641 gatacttgtg gctggaaaag tgcattcctt gttaataaac tttttattta ttacagccca 2701 aagagcagta tttattatca aaatgtcttt tttttttatgt tgaccatttt aaaccgttgg 2761 caataaagag tatgaaaacg cagaaaaaaa aaaaa
```

Human PLK2

(SEQ ID NO: 2)
MELLRTITYQPAASTKMCEQALGKGCGADSKKKRPPQPPEESQPPQSQAQ

VPPAAPHHHHHHSHSGPEISRIIVDPTTGKRYCRGKVLGKGGFAKCYEMT

DLTNNKVYAAKIIPHSRVAKPHQREKIDKEIELHRILHHKHVVQFYHYFE

DKENIYILLEYCSRRSMAHILKARKVLTEPEVRYYLRQIVSGLKYLHEQE

ILHRDLKLGNFFINEAMELKVGDFGLAARLEPLEHRRRTICGTENYLSPE

VLNKQGHGCESDIWALGCVMYTMLLGRPPFETTNLKETYRCIREARYTMP

SSLLAPAKHLIASMLSKNPEDRPSLDDIIRHDFFLQGFTPDRLSSSCCHT

VPDFHLSSPAKNFFKKAAAALFGGKKDKARYIDTHNRVSKEDEDIYKLRH

DLKKTSITQQPSKHRTDEELQPPTTTVARSGTPAVENKQQIGDAIRMIVR

GTLGSCSSSSECLEDSTMGSVADTVARVLRGCLENMPEADCIPKEQLSTS

FQWVTKWVDYSNKYGFGYQLSDHTVGVLFNNGAHMSLLPDKKTVHYYAEL

GQCSVFPATDAPEQFISQVTVLKYFSHYNEENLMDGGDLPSVTDIRRPRL

YLLQWLKSDKALMMLFNDGTFQVNFYHDHTKIIICSQNEEYLLTYINEDR

ISTTFRLTTLLMSGCSSELKNRMEYALNMLLQRCN ii) Design and Production of siRNA

An advantage of inhibitory polynucleotides is that they can be designed to be highly target specific. For example, siRNAs specific for PLK2 can be designed using target sequences that distinguish PLK2 from other PLKs. The program "siDE-SIGN" (Dharmacon, Inc., Lafayette, Colo.) can be used to predict siRNA sequences for any nucleic acid sequence, and is available on the World Wide Web at dharmacon.com. A number of other programs for designing siRNAs are available from others, including Genscript (available on the Web at genscript.com/ss1-bin/app/rnai) and from the Whitehead Institute for Biomedical Research jura.wi.mit.edu/pubint/ http://iona.wi.mit.edu/siRNAext/. Guidelines for designing siRNA are available in the scientific literature (see, e.g., Elbashir et al., 2001, "Duplexes of 21-nucleotide RNAs mediate RNA interference in cultured mammalian cells" *Nature.* 411:494-8.; and Elbashir et al., 2001, "RNA interference is mediated by 21- and 22-nucleotide RNAs" *Genes Dev.* 15:188-200) and published on the Web (see, e.g., "rnaiweb.com/RNAi/siRNA_Design/" and "protocol-online.org/prot/Protocols/Rules-of-siRNA-design-for-RNA-interference—RNAi—3210.html").

There are a variety of ways to produce siRNAs. siRNAs can be generated using kits which generate siRNA from the kinase (e.g., PLK2) gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By producing a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs of the invention can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. Further, 5-6 T's are often added to the 3' end of the oligonucleotide to serve as a termination site for Polymerase III. See also, Yu et al., *Mol Ther* 7(2):228-36 (2003); Matsukura et al., *Nucleic Acids Res* 31(15):e77 (2003).

The siRNA targets can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence.

The siRNA of the invention can be made using any suitable method for producing a nucleic acid, such as the chemical synthesis and recombinant methods disclosed herein and known to one of skill in the art. It will be appreciated that the oligonucleotides can be made using nonstandard bases (e.g., other than adenine, cytidine, guanine, and uridine) or nonstandard backbone structures to provide desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, *Science* 254:1497) or incorporating 2'-O-methyl ribonucleotides, phosphorothioate nucleotides, methyl phosphonate nucleotides, phosphotriester nucleotides, phosphorothioate nucleotides, phosphoramidates.

For example and not limitation, the following are examples of siRNA sequences that can be used to inhibit PLK2. "Start position" refers to the sequence at accession number NM_006622.

|    | Sense Strand Sequence | Region | Start Pos |
|----|----------------------|--------|-----------|
| 1  | CCGGAGATCTCGCGGATTA  | ORF    | 326       |
| 2  | GGGGCAAAGTGCTGGGAAA  | ORF    | 378       |
| 3  | TCACAGCAGAGTAGCTAAA  | ORF    | 469       |
| 4  | GGGAAAAGATTGACAAAGA  | ORF    | 498       |
| 5  | GATTGTGTCTGGACTGAAA  | ORF    | 691       |
| 6  | GCACAGAGATCTCAAACTA  | ORF    | 733       |
| 7  | ACACAGAAGGAGAACGATA  | ORF    | 829       |
| 8  | AGGAGAACGATATGTGGTA  | ORF    | 836       |
| 9  | CATAAGGGAAGCAAGGTAT  | ORF    | 1000      |
| 10 | GCTAGTATGTTGTCCAAAA  | ORF    | 1061      |
| 11 | GAAGACATCTACAAGCTTA  | ORF    | 1304      |
| 12 | CATCAATGAGGATAGGATA  | ORF    | 2062      |
| 13 | GACATGTGGTGGTACGAAA  | 3' UTR | 2281      |
| 14 | CAGAACAGGCTAAGGCATA  | 3' UTR | 2335      |
| 15 | GTGCATTCCTTGTTAATAA  | 3' UTR | 2660      |

The siRNAs above were designed using the siDESIGN® center at www followed by dharmacon.com/DesignCenter/DesignCenterPage.aspx. Each will be double stranded and have a "TT" overhang.

As additional examples, siRNAs from the Ambion Kinase siRNA Library (Ambion, Austin, Tex.) can be used to inhibit PLK2. Exemplary sequences are provided below. Each siRNA is double-stranded with the final TT's (present on both strands) as overhangs:

16.   GGUAUACAAUGCCGUCCUCUTT
17.   GGACUUUGGAACUGUGAAUTT
18.   GGGAAAAGAUUGACAAAGATT iii) Antisense Polynucleotides Antisense polynucleotides can cause suppression by binding to, and interfering with the translation of sense mRNA, interfering with transcription, interfering with processing or localization of RNA precursors, repressing transcription of mRNA or acting through some other mechanism (see, e.g., Sallenger et al. *Nature* 418, 252 (2002). The particular mechanism by which the antisense molecule reduces expression is not critical. Typically antisense polynucleotides comprise a single-stranded antisense sequence of at least 7 to 10 to typically 20 or more nucleotides that specifically hybridize to a sequence from mRNA of a kinase gene of the invention. Some antisense polynucleotides are from about 10 to about 50 nucleotides in length or from about 14 to about 35 nucleotides in length. Some antisense polynucleotides are polynucleotides of less than about 100 nucleotides or less than about 200 nucleotides. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

iv) Ribozymes

Ribozymes are RNA molecules that act as enzymes and can be engineered to cleave other RNA molecules at specific sites. The ribozyme itself is not consumed in this process, and can act catalytically to cleave multiple copies of mRNA target molecules. General rules for the design of ribozymes that cleave target RNA in trans are described in Haseloff & Gerlach, (1988) *Nature* 334:585-591 and Hollenbeck, (1987) *Nature* 328:596-603 and U.S. Pat. No. 5,496,698. Ribozymes typically include two flanking segments that show complementarity to and bind to two sites on a transcript (target subsites) of a gene encoding a kinase of the invention and a catalytic region between the flanking segments. The flanking segments are typically 5-9 nucleotides long and optimally 6 to 8 nucleotides long. The catalytic region of the ribozyme is generally about 22 nucleotides in length. The mRNA target contains a consensus cleavage site between the target subsites having the general formula NUN, and preferably GUC. (Kashani-Sabet and Scanlon, (1995) *Cancer Gene Therapy* 2:213-223; Perriman, et al., (1992) *Gene (Amst.)* 113:157-163; Ruffner, et al., (1990) *Biochemistry* 29: 10695-10702); Birikh, et al., (1997) *Eur. J. Biochem.* 245:1-16; Perrealt, et al., (1991) *Biochemistry* 30:4020-4025). The specificity of a ribozyme can be controlled by selection of the target subsites and thus the flanking segments of the ribozyme that are complementary to such subsites. Ribozymes can be delivered either as RNA molecules or in the form of DNA encoding the ribozyme as a component of a replicable vector or in nonreplicable form as described below.

Expression of a target kinase gene can also be reduced by delivering nucleic acids having sequences complementary to the regulatory region of the target gene (i.e., the target gene promoter and/or enhancers) to form triple helical structures which prevent transcription of the target gene in target cells in the body. See generally, Helene, (1991), *Anticancer Drug Des.*, 6(6):569-584; Helene, et al., (1992), *Ann. N.Y. Acad. Sci.*, 60:27-36; and Maher, (1992), *Bioassays* 14(12):807-815.

v) Administration of siRNA and Other Inhibitory Nucleic Acids

The brain is the therapeutic target of kinase inhibitors of the invention. Therapeutic polynucleotides such as siRNAs, ribozymes and antisense polynucleotides can be administered in a number of ways. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. In general, therapeutic polynucleotides can be administered remotely (e.g., by i.v. injection) with a carrier that facilitates transfer to the brain or they can be delivered directly to the brain.

For direct administration to the brain, siRNAs (i.e., pharmaceutical compositions containing siRNAs) can be administered by any suitable route, including intraventricular and intrathecal injection; intraventricular injection may be facilitated by an intraventricular catheter, for example, attached to a reservoir, such as an Ommaya reservoir, direct injection or perfusion at the lesion site, injection into the brain arterial system, or by chemical or osmotic opening of the blood-brain barrier.

In one approach the therapeutic polynucleotide (e.g., siRNA) is delivered as a peptide conjugate. Kumar et al. exploited the fact that neurotropic viruses, such as rabies viruses, that preferentially infect the nervous system can penetrate the brain. The rabies virus achieves this through glycoprotein on its lipid envelope. To transfer siRNA to the neural cells in the brain, Kumar et al. identified a 29-residue peptide from the rabies virus glycoprotein (RVG) envelope that selectively binds to the acetylcholine receptor expressed by neurons. They fused this peptide with a sequence of 9 arginine residues that binds to siRNAs. After intravenous injection into mice with this peptide-conjugated siRNA, they found that the peptide not only enabled the transvascular delivery of siRNA to the brain but also resulted in efficient gene silencing (Kumar et al., (2007) Nature 448:39-43).

The therapeutic polynucleotide (e.g., siRNA) can be delivered using a liposome and targeted monoclonal antibody system. Pardridge reported that chemically modified liposomes conjugated to monoclonal antibodies raised against epidermal growth factor can penetrate mouse brain. Plasmid DNA encoding for short hairpin RNA (shRNA) was delivered to the brain following intravenous administration with pegylated immunoliposomes (PILs). The plasmid DNA is encapsulated in liposome, which is pegylated, and conjugated with receptor specific targeting monoclonal antibodies. Intravenous RNAi with PILs enables a 90% knockdown of the human epidermal growth factor receptor, which results in a 90% increase in survival time in mice with intra-cranial brain cancer (Pardridge, (2007) Adv. Drug Deliv. Rev. 59:141-152).

Similarly, Boado disclosed the use of the "Trojan Horse Liposome" (THL) technology as an effective delivery system to deliver shRNA to the brain. The tissue target specificity of THL is given by conjugation of approximately 1% of the PEG residues in the liposome to peptidomimetic monoclonal antibodies that bind to specific endogenous receptors (i.e. insulin and transferrin receptors) located on both the BBB and the brain cellular membranes, respectively. (Boado (2007) Pharm. Res. 24:1772-1787).

The therapeutic polynucleotide (e.g., siRNA) can be delivered by the combined use of receptor specific antibody delivery systems and avidin-biotin technology. The siRNA was mono-biotinylated on either terminus of the sense strand, in parallel with the production of a conjugate of the targeting monoclonal antibody and streptavidin. Rat glial cells permanently transfected with the luciferase gene were implanted in the brain of adult rats. Following the formation of intracranial tumors, the rats were treated with a single intravenous injection of biotinylated siRNA attached to a transferrin receptor antibody via a biotin-streptavidin linker. The intravenous administration of the siRNA caused a 69-81% decrease in luciferase gene expression in the intracranial brain cancer in vivo (Xia et al., (2007) Pharm. Res. 24:2309-2316).

The therapeutic polynucleotide (e.g., siRNA) can be delivered by stereotactic surgery or injection. Davidson and Boudreau reviewed in their article that siRNA can be delivered into the brain using neurosurgical method of stereotaxis and showed that a decrease in the transcription of certain genes alleviated symptoms of neuronal diseases (Davidson and Boudreau, (2007) Neuron 53:781-788).

Xia et al. reported that upon intracerebellar injection, recombinant adeno-associated virus vectors expressing short hairpin RNAs, which once expressed are processed into siRNAs, improved motor coordination, restored cerebellar morphology and resolved characteristic ataxin-1 inclusions in Purkinje cells of spinocerebellar ataxia type 1 mice (Xia et al., (2004) Nature Med. 10:816-820).

Further, DiFiglia et al. reported injecting intrastriatally cholesterol-conjugated siRNA that targets human huntingtin mRNA. The authors found that a single administration into the adult mouse striatum of the siRNA effected silencing of the gene, attenuated neuronal pathology, and delayed the abnormal behavioral phenotype observed in a rapid-onset, viral transgenic mouse model of Huntington's disease (DiFiglia et al. (2007) Proc. Natl. Acad. Sci. USA 104:17204-17209). It is noted that such method results only in localized delivery around the injection site, with no widespread effect within the brain.

Singer et al. disclosed using modified lentiviral vectors to deliver siRNAs into the brain cells of the transgenic mice that were producing vast amounts of human beta-amyloid and whose brains where littered with plaques. They found that lentiviral vector delivery of beta-secretase siRNA specifically reduced the cleavage of amyloid precursor protein and neurodegeneration in vivo and indicated that this approach could have potential therapeutic value for treatment of Alzheimer disease (Singer et al. (2005) Nature Neurosci. 8:1343-1349; reviewed in Orlacchio et al. (2007) Mini. Rev. Med. Chem. 7:1166-1176).

Koutsilieri et al. reviewed the literature in the field of siRNA, disclosed different siRNA target strategies aiming for an allele-specific degradation of disease-inducing mRNA and its application in animal models of neurodegenerative diseases, including Alzheimer's disease (AD), amyotrophic lateral sclerosis (ALS), Huntington's disease (HD) and spinocerebellar ataxia (SCA1) (Koutsilieri et al. (2007) J. Neural Transm Suppl. (72):43-49).

Hassani et al. demonstrated that cationic lipids and polyethylenimine (PEI) based polyplexes provided efficient delivery of siRNAs into the brains of new born mice, producing >80% inhibition of an exogenous gene with only picomolar levels of siRNA (Hassani et al. (2005) J. Gene Med. 7:198-207).

Kateb et al. employed nanotechnology as a method for delivering drugs to the brain for treatment of brain cancers. Specifically, the authors disclosed the use Multi-Walled Carbon Nanotubes (MWCNTs) as nanovectors for transporting siRNA (Kateb et al. (2007) Neuroimage 37 Suppl 1:S9-17).

The therapeutic polynucleotide (e.g., siRNA) can be used in combination with other agents to improve or enhance the therapeutic effect of either. This process can involve administering both agents to the patient at the same time, either as a single composition or pharmacological formulation that includes both agents, or by administering two distinct compositions or formulations, wherein one composition includes the siRNA of the invention and the other includes the second agent(s). The siRNA therapy also can precede or follow the other agent treatment by intervals ranging from minutes to weeks.

Polynucleotides can be delivered via a controlled release system. As an example, a pump may be used (Langer, supra; Sefton, 1987, CRC Crit. Ref. Biomed. Eng. 14:201-240; Buchwald et al., 1980, Surgery 88:507-516; Saudek et al., 1989, N. Engl. J. Med. 321:574-579). Alternatively, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, N.Y., 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J. Neurosurg. 71:858-863). In yet another alternative, a controlled release system can be placed in proximity of the therapeutic target, i.e., the brain, thus requiring only a fraction of the systemic dose (e.g., Goodson, 1984, In: Medical Applications of Controlled Release, supra, Vol. 2, pp. 115-138). Other controlled release systems are discussed in the review by Langer (1990, Science 249:1527-1533).

Other approaches can include the use of various transport and carrier systems, for example though the use of viral and/or non-viral delivery systems. For example, siRNA can be introduced into the brain in a virus modified to serve as a vehicle without causing pathogenicity. The virus can be, e.g., adenovirus, fowlpox virus, vaccinia virus, lentivirus, or neurotropic virus such as HIV, herpes simplex virus, flavivirus, or rabies virus. (Li et al., Methods Mol. Biol. 309:261-272 (2005); Davidson et al., Neuron 53:781-788 (2007); Xia et al., Nature Med 10:816-820 (2004); Kumar et al., Nature 448:39-43 (2007); U.S. Pat. Nos. 6,344,445, 6,924,144, 6,521,457). Furthermore, gene therapy approaches, for example as described in Kaplitt et al., U.S. Pat. No. 6,180,613 and Davidson, WO 04/013280, can be used to express nucleic acid molecules in the brain.

Various non-viral delivery systems are known and can be used to administer a therapeutic polynucleotide (e.g., siRNA) to the brain, e.g., encapsulation in liposomes, microparticles, microcapsules, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly (lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722) or by the use of conjugates. For example, chemically modified liposomes encapsulating small hairpin RNA can be conjugated to monoclonal antibodies specific for specific endogenous receptors (e.g., such as insulin and transferrin) located on the blood brain barrier and brain cellular membranes (see Boado, Pharm. Res. 24(9): 1772-1787 (2007)). As a further example, siRNA duplexes can be delivered with the combined use of receptor specific antibody delivery systems and avidin-biotin technology. The siRNA can be mono-biotinylated in parallel with the production of a conjugate of the targeting monoclonal antibody and streptavidin (see Xia et al., Pharm Res. 24(12):2309-16 (2007)). Other methods to deliver siRNA across plasma membranes in vivo include chemically modified siRNAs such as cholesterol-conjugated siRNAs (see DiFiglia et al., Proc Natl Acad Sci USA. 104(43):17204-9 (2007); Wolfrum et al., Nature Biotech. 25(10):1149-1157 (2007); Soutschek et al., Nature 432:173-178 (2003)).

C. Zinc Finger Proteins

Zinc finger proteins can be engineered or selected to bind to any desired target site within a kinase gene of known sequence including, for example, PLK2. An exemplary motif characterizing one class of these proteins ($C_2H_2$ class) is -Cys-$(X)_{2-4}$-Cys-$(X)_{12}$-His-$(X)_{3-5}$-His (where X is any amino acid). A single finger domain is about 30 amino acids in length, and several structural studies have demonstrated that it contains an alpha helix containing the two invariant histidine residues and two invariant cysteine residues in a beta turn co-ordinated through zinc. In some methods, the target site is within a promoter or enhancer. In other methods, the target site is within the structural gene. In some methods, the zinc finger protein is linked to a transcriptional repressor, such as the KRAB repression domain from the human KOX-1 protein (Thiesen et al., *New Biologist* 2, 363-374 (1990); Margolin et al., *Proc. Natl. Acad. Sci. USA* 91, 4509-4513 (1994); Pengue et al., *Nucl. Acids Res.* 22:2908-2914 (1994); Witzgall et al., *Proc. Natl. Acad. Sci. USA* 91, 4514-4518 (1994)). In some methods, the zinc finger protein is linked to a transcriptional activator, such as VIP16. Zinc finger proteins can also be used to activate expression of desired genes. Methods for selecting target sites suitable for targeting by zinc finger proteins, and methods for designing zinc finger proteins to bind to selected target sites are described in WO 00/00388. Methods for selecting zinc finger proteins to bind to a target using phage display are described by EP.95908614.1. The target site used for design of a zinc finger protein is typically of the order of 9-19 nucleotides.

For example, proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

D. Antibodies

Kinase activity can be reduced by administering anti-kinase (e.g., anti-PLK2) antibodies, both intact and binding fragments thereof, such as Fabs, Fvs, which specifically bind to a kinase of the invention. Usually the antibody is a monoclonal antibody although polyclonal antibodies can also be expressed recombinantly (see, e.g., U.S. Pat. No. 6,555,310). Examples of antibodies that can be expressed include mouse antibodies, chimeric antibodies, humanized antibodies, veneered antibodies and human antibodies. Chimeric antibodies are antibodies whose light and heavy chain genes have been constructed, typically by genetic engineering, from immunoglobulin gene segments belonging to different species (see, e.g., Boyce et al., *Annals of Oncology* 14:520-535 (2003)). For example, the variable (V) segments of the genes from a mouse monoclonal antibody may be joined to human constant (C) segments. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions substantially from a mouse-antibody, (referred to as the donor immunoglobulin). See Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539. The constant region(s), if present, are also substantially or entirely from a human immunoglobulin. Antibodies can be obtained by conventional hybridoma approaches, phage display (see, e.g., Dower et al., WO 91/17271 and McCafferty et al., WO 92/01047), use of transgenic mice with human immune systems (Lonberg et al., WO93/12227 (1993)), among other sources. Nucleic acids encoding immunoglobulin chains can be obtained from hybridomas or cell lines producing antibodies, or based on immunoglobulin nucleic acid or amino acid sequences in the published literature.

Antibodies can be administered by intravenous injection. A portion of the injected antibodies will cross the blood-brain barrier. Alternatively antibodies can be administered directly to the brain (e.g., by intraventricular or intrathecal injection). Antibodies may be internalized by synuclein-expressing cells by endocytosis. Alternatively, antibodies may be linked to carrier moiety that facilitates transport across the cell membrane.

In one embodiment an intrabody is used to reduce PLK2 activity. The term "intrabody" or "intrabodies" refers to intracellularly expressed antibody constructs, usually single-chain Fv antibodies, directed against a target inside a cell. Nam, et al. (2002) Methods Mol. Biol. 193:301; der Maurr et al. (2002) J. Biol Chem Nov 22; 277(47):45075; Cohen (2002) Methods Mol Biol 178:367. The scFv gene can be transferred into cells, where scFv protein expression can modulate the properties of its target, e.g. PLK2, sometimes extinguishing protein function and causing a phenotypic knockout. Indeed, the scFv intrabody can be expressed in the cytoplasm and directed to any cellular compartment where it can target intracellular proteins and elicit specific biological effects. Intrabodies thus provide effective means for blocking or modulating the activity of proteins such as PLK2.

E. Kinase Inhibitors to Modulate Activity

In addition to the biological molecules discussed above, small molecule compounds can be used to modulate (usually inhibit) expression or activity of kinases. As discussed below, known kinase inhibitors can be screened for desired target specificity and other properties, and additional inhibitors can be identified based on target specificity. PLK2 or GRK6 are preferred kinases for inhibition because they are candidates for directly phosphorylating alpha-synuclein. PLK2 is a particularly preferred kinase because it has been shown to phosphorylate alpha-synuclein to a much higher level than GRK6 or other kinases tested herein.

Other kinase targets include APEG1, CDC7L1, MET GRK1, GRK2, GRK6, IKBKB, CKII and GRK7 are also preferred kinases for inhibition because they are likely to be indirect activators of the direct kinase(s). PRKG1, MAPK13, and GAK are preferred kinases for activation in Lewy body diseases because they are negative regulators of the phosphorylation of alpha-synuclein. Alternatively, these kinases themselves or fragments or mimetics thereof having similar activity can be used directly as inhibitors of alpha-synuclein phosphorylation. Synphilin can be used as an alternative therapeutic target for inhibition of alpha-synuclein phosphorylation. For example, synphilin can be added to an assay having alpha-synuclein and PLK-2 expression and inhibitors of synphilin identified.

Compounds to be screened for capacity to modulate expression or activity of kinases include the modulators of expression described in Section IV. These compounds also include many known examples of kinase inhibitors, some of which are already approved for therapeutic uses or in clinical trials, usually for treatment of cancer. Lead structures include quinazolines, pyrido[d]- and pyrimidol[d]pyrimidines, pyrazolo[d]-pyrimidines, pyrrolo[d]pyrimidines, pheylamino-pyrimidines, 1-oxo-3-aryl-1H-indene-2-carboxylic acid derivatives, and substituted indolin-2-ones and natural products such as strauosporine (see Traxler et al., 2001, *Medicinal Research Reviews* 21:499-512). Some such compounds are commercially available from Calbiochem-Novabiochem Corp. (La Jolla, Calif.) including H89, Y27632, AT877 (fasudil hydrochloride), rottlerin, KN62, U0123, PD184352, PD98059, SB203580, SB202190, wortmannin, Li$^+$, Ro 318220, chelerythrein and 10-[3-(1-piperazinyl)propyl]-2-trifluoromethyl-phenothiazine (see Davies, *Biochem. J.* 351, 95-105 (2000)). Other compounds currently in clinical trials include STI571 (Glivec™, a phenylamino-pyrimidine derivative) (Novartis), ZD1839 (Iressa) (AstraZeneca), OSI-774 (Roche/OSI), PKI166 (Novartis), CI1033 (Pfizer/Warner-Lambert), EKB-569 (Wyeth-Ayerst), SU5416 (SUGEN), PTK787/ZK224584, aniline-phthalazine derivative (Novartis/Schering AG), SU6668 (Sugen), ZD6474 (AstraZeneca), and CEP2583 (Cephalon). Caveolin-1 is an example of a compound known to modulate the activity of the GRK kinases. Examples of compounds known to modulate the activity of the PLK2/SNK kinases include the RING-H2 domain of hVPS18 (human vacuolar protein sorting 18), and calcium- and integrin-binding protein CIB.

In certain embodiments the therapeutic agent is a small molecule that is a thiazolidone, a quinazoline, a pyrimidine (e.g., a pyrido[d]-pyrimidine, pyrimidol[d]pyrimidine, a pyrazolo[d]-pyrimidine, a pyrrolo[d]pyrimidine, a pheylamino-pyrimidines, or a phenylamino-pyrimidine derivative); an indazole-pyridine derivative, a carboxylic acid derivative (e.g., a 1-oxo-3-aryl-1H-indene-2-carboxylic acid derivative), a substituted indolin-2-one, an aniline-phthalazine derivative; a quinolinone derivative, a benzthiazole-3 oxide compound, an azaindazole compound, or a dihydropteridinone. In certain embodiments the therapeutic agent is a small molecule protein kinase inhibitor described in US 20070203143; US 2007/0179177; US 2007/0135387; US 2007/0010565; US 2007/0037862; US 2007/0010566; US 2006/0074119; US 2006/0079503; US 2006/0223833; US 2005/0014761; US 2004/0176380; US 2006/0040997; U.S. Pat. No. 6,861,422; US 2005/0014760; US 2006/0025411; US 2004/0176380; US 2005/0014761; US 2007/0203143; US 2007/0072833; US 2007/0135387 or WO 03087095. Each of the aforelisted publications is incorporated herein by reference.

Compounds may be synthetic or can be obtained from natural sources, such as, e.g., marine microorganisms, algae, plants, and fungi. Other compounds that can be tested include compounds known to interact with alpha-synuclein, such as synphilin. Alternatively, compounds can be from combinatorial libraries of agents, including peptides or small molecules, or from existing repertories of chemical compounds synthesized in industry, e.g., by the chemical, pharmaceutical, environmental, agricultural, marine, cosmeceutical, drug, and biotechnological industries. Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax WO 95/12608, Affymax WO 93/06121, Columbia University WO 94/08051, Pharmacopeia WO 95/35503 and Scripps WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like. Compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules.

As discussed above, kinase inhibitors that preferentially inhibit PLK2 are of particular value. As is shown in Examples 13-16, below, we assayed the effect of several kinase inhibitors levels of phosphorylation of alpha-synuclein in rat ventral mesencephalon and mouse cortical cell cultures, and other cells.

An exemplary compound for use according to the invention is the compound BI2536 having the structure:

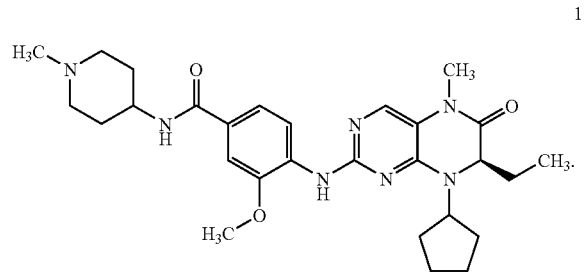

1

As demonstrated in the Examples below, BI 2536 (4-[[(7r)-8-cyclopentyl-7-ethyl-5,6,7,8-tetrahydro-5-methyl-6-oxo-2-pteridinyl]amino]-3-methoxy-n-(1-methyl-4-piperidinyl)-benzamide; also called ELN-481574-2;) reduced phosphorylation of alpha synuclein in a variety of cell types. BI 2536 inhibits PLK1, PLK2 and PLK3 (see, Steegmaier et al., 2007, *Current Biology*, 17:316-322) and does not inhibit PLK4 (Johnson et al., 2007, *Biochemistry* 46:9551-9563). Steegmaier et al. reported an $IC_{50}$ of 0.83 nM for PLK1, 3.5 nM for PLK2 and 9 nM for PLK3. In tests described in Example 15, below, BI2536 was shown to have 16-fold selectivity for PLK2 ($IC_{50}$ 11 nM) and 13-fold selectivity for PLK3 ($IC_{50}$ 14 nM). BI 2536 has category IV PLK2 specificity (Inhibits PLK2 activity and has no, or reduced, effect on PLK4) and is a candidate for Parkinson's disease therapeutics.

Accordingly, in one aspect the invention provides a method for inhibiting phosphorylation of alpha-synuclein in a mammalian cell by contacting the cell with an amount of BI 2536 that reduces PLK2 activity in the cell such that phosphorylation of alpha-synuclein is reduced. In a related aspect, the invention provides a method of treating a patient diagnosed with Parkinson's disease by administering a therapeutically effective amount of BI 2536.

U.S. Pat. No. 6,861,422, incorporated herein by reference, describes BI 2536 and structurally related dihydropteridinone kinase inhibitors. Dihydropteridinone compounds that inhibit PLK2 are useful for inhibiting phosphorylation of synuclein.

Another exemplary compound for use according to the invention is the compound ELN-481080 having the structure:

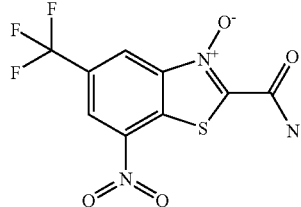

2

See, McInnes et al., 2006, *Current Topics in Medicinal Chemistry* 5:181-97 (Compound 8). Also see US 2006/0040997, "Benzthiazole-3 oxides useful for the treatment of proliferative disorders" incorporated herein by reference. See Example 14, below.

Several inhibitors of polo-like kinases are described in Johnson et al., 2007, "Pharmacological and functional comparison of the polo-like kinase family: insight into inhibitor and substrate specificity" *Biochemistry* 46:9551-63. Of those characterized in that study, several preferentially inhibit PLK2 and may be used as therapeutic agents.

For example, CHIR-258 (3) is a multitarget growth factor kinase inhibitor developed for treatment of t(4;14) multiple myeloma (Trudel et al., 2005, *Blood*. 105:2941-8).

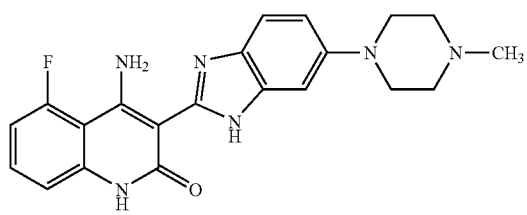

3

$K_i$ values for CHIR-258 for PLK1, PLK2, PLK3 and PLK4 are >20, 0.85, >20, and 1.4 uM respectively meaning CHR-258 is a Type VI inhibitor (inhibits PLK2 activity and has reduced effect on PLK1, PLK3 and PLK4). Although CHIR-258 is an inhibitor of receptor tyrosine kinases, warranting study of the side effect profile, targeted delivery to the brain and/or particular treatment regimens can be investigated to determine whether the compound has an acceptable therapeutic index for treatment and prevention of Parkinson's Disease, and a clinically acceptable side effect profile. CHIR-258 and related quinolinone derivatives are described in WO03087095, incorporated herein by reference.

Sunitinib (SU11248) (4) is an example of a Type IV inhibitor, based on the Johnson et al., 2007, studies (inhibits PLK2 activity with reduced effect on PLK1 or PLK3). Sunitinib was identified as an inhibitor of FLT3 receptor tyrosine kinase (RTK) approved for treatment of advanced renal cell carcinoma and gastrointestinal stromal tumors that are refractory or intolerant to imatinib (Gleevec). O'Farrell et al., 2003, *Blood* 101:3597-605.

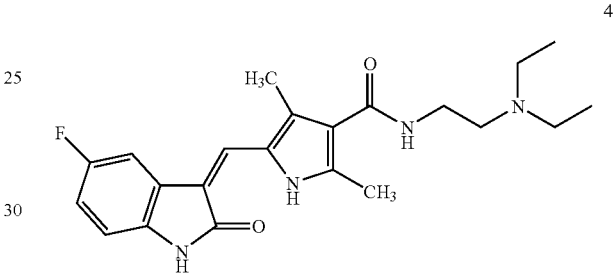

4

5-(5,6-dimethoxy-1H-benzimidazol-1-yl)-3-{[2-(trifluoromethyl)-benzyl]oxy}thiophene-2-carboxamide (5) is an example of a Type III agent (inhibits PLK2 activity and has reduced effect on PLK4). The compound was initially identified as a selective thiophene benzimidazole ATP-competitive inhibitor of PLK1 and PLK3 for treatment of neoplasms. Lansing et al., 2007, *Mol Cancer Ther.* 6:450-9. Also see US 20060074119, incorporated herein by reference, describing other inhibitors of PLKs.

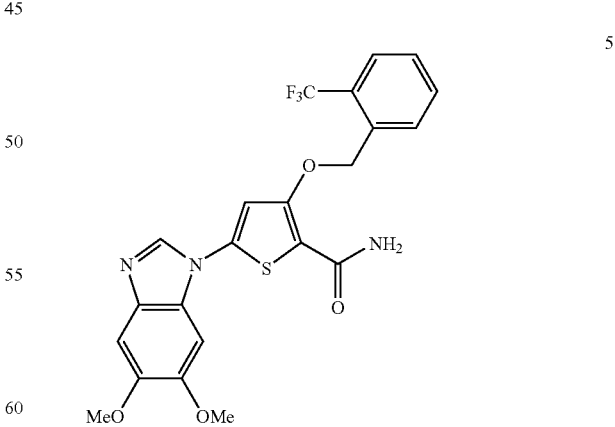

5

Compounds 6 and 7 are indazole-pyridine based inhibitors of protein kinase B/Akt proposed as antitumor agents (see Woods et al., 2006, *Bioorg Med Chem.* 14:6832-46). Each has a lower $K_i$ for PLK2 than for PLK1 or PLK3 (Type IV inhibitor) and may be used for treatment of Parkinson's disease.

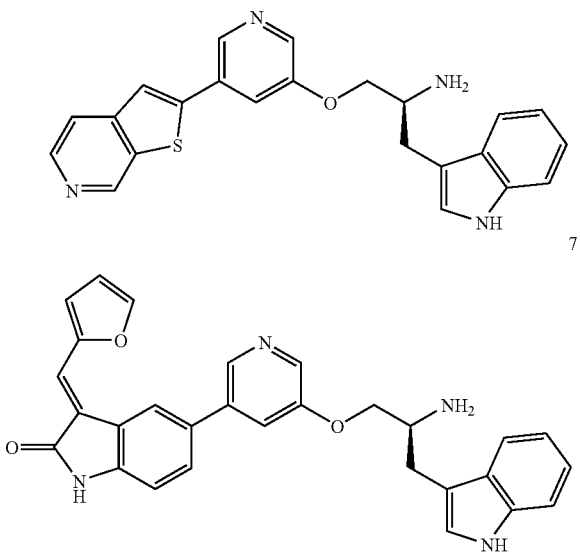

In some embodiments the agent is a naturally occurring agent. In some embodiments the agent has a molecular weight less than 4000, sometimes less than 3000, sometimes less than 2000, usually less than 1000, and sometimes less than 500.

In certain embodiments the therapeutic agent is a small molecule other than a thiazolidone. In certain embodiments the therapeutic agent is a small molecule other than X, where X is one of, or an independently selected one or more of, (i) a thiazolidone, (ii) a quinazoline, (iii) a pyrimidine, (iv) pyrido[d]-pyrimidine, (v) a pyrimidol[d]pyrimidine, (vi) a pyrazolo[d]-pyrimidine, (vii) a pyrrolo[d]pyrimidine, (viii) a pheylamino-pyrimidines, (ix) phenylamino-pyrimidine derivative, (x) a indazole-pyridine derivative, (xi) a carboxylic acid derivative, (xii) a 1-oxo-3-aryl-1H-indene-2-carboxylic acid derivative, (xiii) a substituted indolin-2-one, (xiv) an aniline-phthalazine derivative; (xv) a quinolinone derivative, (xvi) a thiazolidinone compound, (xvii) a benzthiazole-3 oxide (xviii) a dihydropteridinone or (xix) an aza-indazole compound.

In certain embodiments the therapeutic agent is a small molecule with the proviso it is not a compound described in US 2007/0179177. In certain embodiments the therapeutic agent is a small molecule with the proviso it is not a compound described in US 2007/0010565. In certain embodiments the therapeutic agent is a small molecule with the proviso it is not a compound described in US 2007/0037862. In certain embodiments the therapeutic agent is a small molecule with the proviso it is not a compound described in 2007/0010566. In certain embodiments the therapeutic agent is a small molecule with the proviso it is not a compound described in 2006/0079503. In certain embodiments the therapeutic agent is a small molecule with the proviso it is not a compound described in US 2006/0223833. Each of the aforelisted publications is incorporated herein by reference.

VI. Methods of Treatment

The invention provides several methods of preventing or treating Lewy Body disease in patients suffering from or at risk of such disease. Therapeutic agents include any of the agents described above that inhibit phosphorylation of alpha-synuclein and/or reduce total levels of alpha-synuclein.

The experimental examples below provide strong evidence that PLK2 is a synuclein kinase. Thus, in a particular aspect, the invention provides a method of effecting treatment or prophylaxis of an LB disease by administering to a patient suffering from or at risk of the disease an effective regime of an agent effective to suppress activity or expression of PLK2. It is preferred that the agent shows a high level of specificity for PLK2.

Patients amenable to treatment include individuals at risk of disease of a LBD but not showing symptoms, as well as patients presently showing symptoms. Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHL1, LRRK2, and CYP2D6 genes; particularly mutations at positions 30 and 53 of the alpha-synuclein gene. Another genetic marker of risk toward PD includes measuring the levels or SNCA dosage or transcription. Individuals presently suffering from Parkinson's disease can be recognized from its clinical manifestations including resting tremor, muscular rigidity, bradykinesia and postural instability.

In some methods, the patient is free of clinical symptoms or risk factors for any amyloidogenic disease other than one characterized by Lewy bodies. In some methods, the patient is free of clinical symptoms or risk factors of any disease characterized by extracellular amyloid deposits.

In some methods the patient is not diagnosed with cancer and/or Alzheimer's disease.

Treatment typically entails multiple dosages over a period of time. Treatment can be monitored by assaying signs or symptoms of the disease being treated relative to base line measurements before initiating treatment. In some methods, administration of an agent results in reduction of intracellular levels of aggregated alpha-synuclein. In some methods, administration of the agent results in a reduction in levels of phosphorylated synuclein. In some methods, administration of an agent results in improvement in a clinical symptom of a LBD, such as motor or cognitive function in the case of Parkinson's disease.

In prophylactic applications, pharmaceutical compositions or medicaments are administered to a patient susceptible to, or otherwise at risk of a LBD in regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylactically-effective regime.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

The dosage and frequency of administration can vary depending on whether the treatment is prophylactic or therapeutic. Guidance can be obtained from the dosing schedules of kinase inhibitors currently approved or in clinical trials for other indications. Dosages in the range of 0.1-1000 mg, preferably 10-500 mg, may be used. Frequency of dosing (e.g., daily, weekly or monthly) depends on the half-life of the drug. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Therapeutic agents can be administered by parenteral, topical, intravenous, oral, subcutaneous, intraarterial, intracranial, intrathecal, intraperitoneal, intranasal or intramuscular means for prophylactic and/or therapeutic treatment. In some methods, agents are injected directly into a particular tissue where deposits have accumulated, for example intracranial injection. In some methods, agents are administered as a sustained release composition or device, such as a Medipad™ device. Small molecules that pass through the blood brain barrier sufficiently are usually administered orally, but can also be administered intravenously.

Agents of the invention can optionally be administered in combination with other agents that are at least partly effective in treatment of LBD. Agents of the invention can also be administered in conjunction with other agents that increase passage of the agents of the invention across the blood-brain barrier.

Agents of the invention are often administered as pharmaceutical compositions comprising an active therapeutic agent and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body.

Compositions may be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein. Alternatively, transdermal delivery can be achieved using a skin patch or using transferosomes (Paul et al., *Eur. J. Immunol.* 25, 3521-24 (1995); Cevc et al., *Biochem. Biophys. Acta* 1368, 201-15 (1998)).

VII. Lewy Body Diseases

Lewy Body Diseases (LBD) are characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Lewy Bodies are spherical protein deposits found in nerve cells. Their presence in the brain may disrupt the brain's normal function interrupting the action of chemical messengers including acetylcholine and dopamine. Lewy Body diseases include Parkinson's disease (including idiopathic Parkinson's disease (PD)), Diffuse Lewy Body Disease (DLBD) also known as Dementia with Lewy Bodies (DLB), Combined Alzheimer's and Parkinson disease and multiple system atrophy (MSA). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form in selected regions throughout the brain stem, midbrain, and in advanced disease, cerebral cortex. See, Braak et al., 2003, "Staging of brain pathology related to sporadic Parkinson's disease" *Neurobiology of Aging* 24:197-211. Other Lewy Body diseases include Pure Autonomic Failure, Lewy body dysphagia, Incidental LBD, Inherited LBD (e.g., mutations of the alpha-synuclein gene, PARK3 and PARK4) and Multiple System Atrophy (e.g., Olivopontocerebellar Atrophy, Striatonigral Degeneration and Shy-Drager Syndrome).

VIII. Identification of Modulators of Kinases that Directly or Indirectly Phosphorylate Alpha-Synuclein Agents that modulate expression or activity of a kinase that directly or indirectly phosphorylates alpha-synuclein can be identified by a variety of assays. Particularly preferred are agents that inhibit kinases PLK2 or GRK6, or APEG1, CDC7L1, MET GRK1, GRK2, GRK6, IKBKB, CKII and GRK7, or agents that activate PRKG1, MAPK13, and GAK. Agents that modulate expression can be identified in cell-based assays in which an agent under test is introduced into a cell expressing alpha-synuclein and a kinase that directly or indirectly effects phosphorylation of the alpha-synuclein or modulates levels of total alpha-synuclein. Optionally, particularly for PLK2, synphilin can be expressed as well to augment activity of the kinase. The agent can be introduced directly or in the form of a nucleic acid encoding the agent and capable of expressing the agent. The cell can naturally express the alpha-synuclein and kinase or one or both of these can be introduced into the cell by transfection of a suitable nucleic acid. The effect of the agent on expression of the kinase can be measured directly from the level of the kinase or its mRNA, or indirectly by measuring the level of phosphorylated alpha-synuclein or total alpha-synuclein as described above. The level of kinase mRNA can be assayed by a hybridization type assay. The level of the kinase can be assayed by an immunoassay. Optionally, the kinase is tagged with a peptide label such as Flag™ (Hopp et al., *BioTechnology* 6, 1204-1210 (1988)) to facilitate detection. An agent that decrease the level of the kinase, decrease the level of phosphorylation of alpha-synuclein and/or decrease the level of total alpha-synuclein relative to similar control cells not treated with an agent have a pharmacological activity potentially useful for treatment of Lewy body diseases.

Agents are also screened for activity to modulate activity of a kinase suspected of phosphorylating alpha-synuclein or increasing total levels of alpha-synuclein. An initial screen can be performed to select a subset of agents capable of specifically binding to a kinase. Such an assay can be performed in vitro using an isolated kinase or fragment thereof having kinase activity.

In one embodiment an agent that reduces alpha-synuclein phosphorylation in a mammalian cell expressing alpha-synuclein, and which may be used as a therapeutic agent, is identified based on the following criteria: a) reduces activity of PLK2 in a cell expressing PLK2; and b) does not reduce activity of PLK1 in a cell expressing PLK1, or reduces activity of PLK1 at a higher $EC_{50}$ than for PLK2; and/or c) does not reduce activity of PLK3 in a cell expressing PLK3, or reduces activity of PLK3 at a higher $EC_{50}$ than for PLK2; and/or d) does not reduce activity of PLK4 in a cell expressing PLK4, or reduces activity of PLK4 at a higher $EC_{50}$ than for PLK2. In one embodiment an agent is selected that meets all of criteria a-d. The mammalian cell may be a cell overexpressing alpha-synuclein (e.g., transfected with a vectors expressing exogenous, e.g., human, alpha-synuclein). The mammalian cell may be a neuronally-derived cell such as, for example, cells from mouse cortical cell cultures, rat ventral mesencephalon cell cultures, or other neuronal cells from humans or non-human mammals.

Agents identified by such a screen can then be assayed functionally. Agents can also be directly assayed functionally without the binding assay. For a kinase that directly phosphorylates alpha-synuclein, modulators can be screened by an in vitro assay combining the kinase, alpha-synuclein, ATP and the modulator in comparison with a control in which the modulator is omitted. Optionally, synphilin can be included as well to increase phosphorylation particularly if the kinase is PLK2. The modulator has potentially useful pharmacological activity if it reduces the level of phosphorylation beyond the margin of typical experimental error relative to the control.

Agents can also be screened in cells expressing alpha-synuclein and the kinase under test, and optionally, particularly if the kinase is PLK2, synphilin. Such screens are effective regardless of whether the kinase phosphorylates alpha-synuclein directly or indirectly, or otherwise affects levels of alpha-synuclein. Cells are contacted with the agent and levels of total alpha-synuclein and phosphorylated alpha-synuclein are measured, as above, relative to a control cell not treated with the agent. A reduction in the level of phosphorylated alpha-synuclein or total alpha-synuclein relative to the corresponding level in a control cell not treated with the agent, beyond the margin of typical experimental error, is an indication that the compound has pharmacological activity potential useful in treating Lewy body diseases. Agents may also be screened in cells for ability to reduce aggregation of alpha-synuclein in the cell.

Agents can also be screened in transgenic animal models of Lewy body disease, alone or in combination with the other assays described above. Total levels of alpha-synuclein, phosphorylated alpha-synuclein or Lewy-like bodies or other indica of Lewy Body pathology or symptoms are measured in a transgenic animal treated with an agent under test relative to corresponding levels in a similar control animal not treated with the agent. A reduction in one or more of these levels is an indication, the agent has pharmacological activity potentially useful in treating Lewy body diseases.

The kinase used in the above assays and cellular and transgenic models is preferably a human kinase having a sequence in one of the references or accession numbers provided in this disclosure. However, allelic (variants within a species) and species variants (variants between species) of such a kinase can also be used, as can variants having at least 90% sequence identity to such a kinase. For subsequent clinical use, agents identified by such assays are capable of modulating the activity or expression of a natural kinase, preferably a form occurring in humans.

IX. Transgenic Animal and Cellular Models of Lewy Body Disease

Transgenic animal models are useful for testing the capacity of kinases to effect phosphorylation of alpha-synuclein and formation of Lewy-like bodies as described above. Transgenic animals are also useful for screening agents for activity in modulating phosphorylation or production of alpha-synuclein. Particularly preferred are agents that inhibit or are suspected of inhibiting kinases including PLK2 and GRK6, or APEG1, CDC7L1, MET GRK1, GRK2, GRK6, IKBKB, CKII and GRK7. Also preferred are agents that activate or are suspected of activating kinases PRKG1, MAPK13, and GAK. Further, knockout animals (i.e., animals in which an endogenous kinase is inactivated either by insertional inactivation or trans inhibition by an siRNA, zinc finger protein or the like) are useful for identifying the effect of eliminating activity of a kinase on an animal. For example, analysis of a PLK2-knockout mouse can indicate whether inhibitors of PLK2 have any side effects. Analogous knockouts can reveal similar information for other kinases.

In general, transgenic models have a genome comprising an alpha-synuclein transgene in operable linkage with one or more regulatory sequences to ensure its expression. Expression of the transgene leads to Lewy-body like deposits of alpha-synuclein in the brain of the animal. Several such transgenic animals have been described in the scientific and patent literature (see Masliah et al., *Am. J. Pathol.* (1996) 148:201-10 and Feany et al., *Nature* (2000) 404:394-8)), U.S. Pat. No. 5,811,633 (for transgenic animals with a mutant form of APP). Some transgenic animals express variant or mutant alpha-synuclein, such as familial mutants A30P, A53T, and E46K of alpha synuclein. Some transgenic animals have an additional transgene, such as a transgene encoding a kinase as described above. Transgenic animals bearing a transgene expressing alpha-synuclein protein can also be crossed with other transgenic models of neurogenic disease, such as models of Alzheimer's disease. For example, transgenic animals bearing a transgene expressing a truncated alpha-synuclein protein can be crossed with transgenic animals bearing a transgene expressed APP with a FAD mutation as described by e.g., Games et al., *Nature* 373, 523 (1995) McConlogue et al., U.S. Pat. No. 5,612,486, Hsiao et al., *Science* 274, 99 (1996); Staufenbiel et al., *Proc. Natl. Acad. Sci. USA* 94, 13287-13292 (1997); Sturchler-Pierrat et al., *Proc. Natl. Acad. Sci. USA* 94, 13287-13292 (1997); Borchelt et al., *Neuron* 19, 939-945 (1997)). The procedure for performing such a cross is described by e.g., Masliah et al., *PNAS USA* 98:12245-12250 (2001), which reports a cross between transgenic mice expressing a full length alpha-synuclein with PDAPP mice as described by Games et al Transgenic animals of the invention are preferably rodents, such as mice or rats, or insects, such as *Drosophila*. Transgenic animals can be produced by introduction of a transgene at the germline stage in which case all or substantially all (except for rare loss through somatic mutation) of the cells of the transgenic animal include the transgene integrated into the genome. Transgenes can be introduced by microinjection, nuclear transfer or viral infection into cells or animals. Adeno Associated Viruses and Lentiviruses are particularly suitable for the latter. Alternatively, transgenes can be introduced by viral infection into the brain of the animal. Such transgenes are not part of the germline of recipient animals but can be targeted to regions of the brain responsible for disease (e.g., the substantia nigra). Such animal models incorporate an alpha-synuclein into the genome of brain cells and are disposed to develop at least one characteristic of LBD disease. Lentiviruses provide a suitable vehicle for so introducing an alpha-synuclein transgene into the brain (see *Brain Pathology* 13, 364-372 (2003); Bjorklund, *Trends Neurosci.* 26, 386-92 (2003), Lotharius et al., *J. Biol. Chem.* 277, 38884-94 (2002), Zhou et al., *Brain Research* 866, 33-43 (2000)). Transgenic animals can also include a transgene capable of expressing one of the kinases of the invention (e.g., a nucleic acid encoding the kinase in operable linkage with regulatory elements to ensure its expression in the brain of an animal), instead of or as well as a transgene expressing alpha synuclein. Optionally, a transgene expressing synphilin can be included as well. Some cellular models express variant or mutant alpha-synuclein, such as familial mutants A30P, A53T, and E46K of alpha synuclein. Some cells have an additional transgene, such as a transgene encoding a kinase as described above, e.g., PLK2.

Cellular models of Lewy body disease can also be used in the screening methods of the invention. Cells transfected with alpha-synuclein form inclusion bodies containing aggregated alpha-synuclein. The transformed cells are preferably neuronal cells, such as GT1-7 neuronal cells (Hsue et al. *Am. J. Pathol.* 157:401-410 (2000)), PC12 cells or SY5Y neuroblastoma cells. PEAK and/or HCC cells can also be used (see Example 10). The cells are preferably human cells. A vector comprising a segment encoding a form of alpha-synuclein operably linked to one or more regulatory sequences that ensure expression of the expression is transfected into the cells. Cells can also be transfected with a nucleic acid encoding a kinase of the invention as described above. Transfected cells can be used to screen agents for activity in clearing alpha-synuclein inclusions. An exemplary cellular model is identified in Example 10 in which HCC neuronal cells are transfected with synuclein and PLK2 with the result that aggregation and phosphorylation of the synuclein matching LB formation occurs. In order to identify inhibitors of the kinase, the cell is contacted with the inhibitor and a reduction in the amount of phosphorylation and/or aggregation is identified.

X. Alpha-Synuclein Isolation and Phosphorylation

Human alpha-synuclein is a polypeptide of 140 amino acids having the following amino acid sequence:

```
                                         (SEQ ID NO: 1)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Ueda et al., *Proc. Natl. Acad. Sci. USA* (1993) 90:11282-6); GenBank accession number: P37840). The protein has three recognized domains, a KTKE repeat domain covering amino acids 1-61, a NAC (Non-Amyloid Component) domain running from about amino acids 60-95, and a C-terminal acidic domain running from about amino acid 98 to 140.

Unless otherwise apparent from the context, reference to alpha-synuclein includes the natural human amino acid sequence indicated above as well as analogs including allelic, species and induced variants (e.g., E83Q, A90V, A76T) having at least 90% sequence identity to natural human alpha-synuclein. Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. Some natural allelic variants are genetically associated with hereditary LBD. The term "allelic variant" is used to refer to variations between genes of different individuals in the same species and corresponding variations in proteins encoded by the genes. Allelic variants include familial mutants or variants, such as E46K, A30P and A53T (the first letter indicates the amino acid in SEQ ID NO:1, the number is the residue position in SEQ ID NO:1, and the second letter is the amino acid in the allelic variant). Analogs can include any combination of allelic variants. The A53T variation is associated with enhanced levels of phosphorylation at position 129 of alpha-synuclein in an individual having the mutation relative to the norm of phosphorylation in undiseased individuals who lack the mutation.

Alpha-synuclein, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989).

A method was developed herein to prepare large amounts of wild-type phospho-S129 alpha-synuclein, mutant and/or familial forms in a bacterial expression system. When recombinant hPLK2 was co-expressed with alpha-synuclein in bacteria, the phospho-S129 alpha-synuclein that was produced in the cell was recovered with a very high yield and purity. This is because, unlike most *E. coli* proteins, the alpha-synuclein could resist heating. After boiling of the bacterial lysate, alpha-synuclein purity reached about 95% before chromatography.

To co-express recombinant protein in a bacterial system, the plasmids harboring each gene of interest were chosen be compatible within the bacterial cell by ensuring that they possessed a different origin of replication and a different antibiotic selection. The alpha-synuclein gene was subcloned into a pDEST24 compatible vector, pCDF1b. BL21-DE3 bacteria were then co-transformed with both the pDEST24 containing wild-type hPLK2 or hPLK2 constitutive mutant constructs without a GST tag and the pCDF1b/AS plasmid. The bacterial lysates were boiled and the supernatant, expected to contain alpha-synuclein was analyzed by Western blot with an anti-phospho-S129-alpha-synuclein antibody (11A5), by using the SYPRO Ruby™ and ProZDiamond™ dyes (total protein and phospho-Ser/Thr specific dye respectively), by SDS-PAGE and by mass spectrometry, with the results that a fairly pure phospho-S129-alpha-synuclein product was isolated that, upon analysis by mass spectrometry was revealed to be more than 95% phosphorylated. To ensure that the final product was 100% phosphorylated and highly pure, the supernatant of the last centrifugation was passed through an 11A5-sepharose-affinity purification column one or more times. Any contamination was removed using HPLC.

XI. Examples

EXAMPLE 1

Screen for Kinases that Modulate Alpha-Synuclein Phosphorylation

To identify the kinase or kinases that phosphorylates α-synuclein at serine-129 an siRNA kinase library (Ambion) was screened on cells containing a quantifiable amount of phosphorylated α-synuclein. Human embryonic kidney cell line HEK293 cells (PEAK cells) stably transfected with human wild-type α-synuclein under control of a CMV promoter (PEAK-Syn cells) were transfected with 100 nM siRNAs targeting 597 human kinases and were assayed by ELISA assays to quantitate total and phospho-synuclein levels. Ninety-five kinases with siRNAs that altered the percentage of phosphorylated alpha-synuclein were identified (see Tables 1-2). Of those, 28 belonged to the class of kinases that phosphorylate serine residues and hence were capable of directly phosphorylating α-synuclein at serine-129. Others were tyrosine kinases. Although tyrosine kinases do not phosphorylate α-synuclein at ser-129 directly, they can act as upstream regulators of the alpha-synuclein kinase. Two of these ser/thr kinases, casein kinase 2 and calcium/calmodulin dependent protein kinase II, have been reported to phosphorylate α-synuclein in vitro (Pronin et al, *J. Biol. Chem.* 275: 26515-26522 (2000), Okochoa et al, *J. Biol. Chem.* 275: 390-397 (2000); Nakajo et al, *Eur. J. Biochem.* 217: 1057-1063 (1993) and a casein kinase 2 inhibitor has been reported to decrease phospho-synuclein levels in cells (Okochoa et al, 2000). Several of the GRK family members (although not GRK6) have been reported to phosphorylate alpha-synuclein in vitro (Pronin et al, 2000). GRK2 expression in flies has been reported to increase phospho-synuclein levels (Chen and Feany, *Nature Neurosci.* 8: 657-663 (2005)).

In addition to kinases that lower phospho-synuclein levels, 99 kinases whose siRNAs altered total α-synuclein levels in the PEAK-Syn cells were identified in Table 2 and included fucokinase (FUK), Genbank number NM_145059; Protein Kinase N1 (PRKCL1, PKN1), Genbank number NM_002741; Doublecortin and CaM kinase-like 1 (DCAMKL1) NM_004734; Branched chain Ketoacid dehydrogenase kinase (BCKDK) NM_005881; Aurora Kinase C (AURKC, STK13); NM_003160, Kinase suppressor of ras 2 (FLJ25965), NM_173598; FLJ32704; MAP2K6; and Tousled-like kinase 2 (TLK2) NM_006842. The mechanism of action may involve either regulation of alpha-synuclein turnover or synthesis (See Table 2).

Tables 1A, 1B and 1C show kinases whose inhibition modulates the phosphorylation at position ser-129. Table 1A, B, and C differ in the type of kinase. Table 1A shows kinases that can phosphorylate serine residues and often tyrosine and/or threonine as well. Table 1B shows tyrosine kinases that cannot (so far as is known) modify serine residues. Table 1C shows kinases not known to have phosphorylate proteins. Kinases from the upper portion of Table 1A are candidates for direct phosphorylation of ser-129 of alpha-synuclein. Kinases from the upper part of Table 1B are also useful therapeutic targets via roles indirectly phosphorylating alpha-synuclein. Proteins in the upper part of Table 1C are also useful therapeutic targets for the same reason. Cols. 1, 2 and 3 of each table indicate the gene name, kinase name and Genbank accession number of kinases. The next column indicates whether inhibiting expression of the kinase decreased ("down") or increased ("up") phosphorylation. The next three columns indicate the number of standard deviations the measured level of phosphorylation departs from the mean in three independent experiments. The final two columns indicate the kinase family (i.e., amino acid specificity) and group.

Tables 2 and 3 show kinases whose inhibition modulates the overall levels of human alpha-synuclein without changing the percentage of phosphorylation. Table 2 shows all of the kinases with the strongest reduction in levels of human alpha-synuclein. The columns are labeled similarly to Tables 1A, 1B and 1C.

Tables 1A-C: Complete list of Kinase candidates that reduce phosphorylation

TABLE 1A

| | | | Serine/Threonine Kinases | | | | | |
|---|---|---|---|---|---|---|---|---|
| Gene Name | Kinase Name | Genbank | Up/Down | # of SD | # of SD | # of SD | Kinase Family | Kinase Group |
| GPRK6 | G protein-coupled receptor kinase 6 | NM_002082 | Down | 1.25 | 1.25 | | Ser/Thr | AGC |
| PDPK1 | 3-Phosphoinositide dependent protein kinase-1 | NM_002613 | Down | 2.25 | 2.75 | | Ser/Thr | AGC |
| FLJ11159 | RIO kinase 2 (yeast) | NM_018343 | Down | 1.5 | 1.5 | | Ser/Thr | Atypical |
| *APEG1 | Aortic preferentially expressed gene 1 | NM_005876 | Down | 1.75 | 2 | 2.25 | Ser/Thr/Tyr | CAMK |
| ARK5 | AMP-activated protein kinase family member 5 | NM_014840 | Down | 1 | 1 | 1.5 | Ser/Thr | CAMK |
| *CAMK1 | Calcium/calmodulin-dependent protein kinase I | NM_003656 | Down | 1.5 | 1.75 | 2 | Ser/Thr | CAMK |
| SSTK | Serine/threonine protein kinase SSTK | NM_032037 | Down | 1 | 1 | | Ser/Thr | CAMK |
| PHKG2 | Phosphorylase kinase, gamma 2 (testis) | NM_000294 | Down | 1 | 2 | | Ser/Thr | CAMK |
| CASK | Calcium/calmodulin-dependent serine protein kinase | NM_003688 | Down | 1.25 | 1.25 | | Ser/Thr | CAMK |
| PRKAA2 | Protein kinase, AMP-activated, alpha 2 catalytic subunit | NM_006252 | Down | 1 | 1.75 | | Ser/Thr | CAMK |
| CDK8 | Cyclin-dependent kinase 8 | NM_001260 | Down | 1 | 1 | 1.25 | Ser/Thr | CMGC |
| *CDC2L5 | Cell division cycle 2-like 5 | NM_003718 | Down | 1.25 | 1.5 | | Ser/Thr/Tyr | CMGC |
| ERK8 | Extracellular signal-regulated kinase 8 | NM_139021 | Down | 1.5 | 1.5 | | Ser/Thr | CMGC |
| *CDK4 | Cyclin-dependent kinase 4 | NM_000075 | Down | 1 | 1 | | Ser/Thr** | CMGC |
| CLK3 | CDC-like kinase 3 | NM_003992 | Down | 1 | 1.5 | | Ser/Thr/Tyr | CMGC |
| PRP4 | Pre-mRNA processing factor 4 homolog B (yeast) | NM_003913 | Down | 1.25 | 1.75 | | Ser/Thr | GO |
| CKIIA2 | Casein kinase 2, alpha prime subunit | NM_001896 | Down | 1 | 1.5 | | Ser/Thr | Other |
| PLKII/SNK | Polo like kinase 2 | NM_006622 | Down | 1 | 1.5 | 2.25 | Ser/Thr | Other |
| CKIIA1 | Casein kinase 2, alpha subunit | NM_001895 | Down | 1 | 1.75 | 2.25 | Ser/Thr | Other |
| MAP2K1 | mitogen-activated protein kinase kinase 1 (MEK1; MKK1) | NM_002755 | Down | 1 | 1.75 | | Ser/Thr/Tyr | STE |
| MAP2K4 | mitogen-activated protein kinase kinase 4 (MEK4; MKK4; JNKK) | NM_003010 | Down | 1 | 2 | | Ser/Thr/Tyr | STE |
| MAP2K5 | mitogen-activated protein kinase kinase 5 (MEK5; MKK5) | NM_002757 | Down | 1 | 1.25 | | Ser/Thr/Tyr | STE |
| TESK2 | testis-specific kinase 2 | NM_007170 | Down | 1 | 1 | 1.5 | Ser/Thr/Tyr | TKL |
| RIPK3 | receptor-interacting serine-threonine kinase 3 | NM_006871 | Down | 1 | 1.25 | | Ser/Thr/Tyr | TKL |
| PRKG2 | protein kinase, cGMP-dependent, type II | NM_006259 | Down | 2.25 | | | Ser/Thr | AGC |
| JIK | TAO Kinase 3 (MAP3K18) | NM_016281 | Down | 2 | | | Ser/Thr | STE |
| PAK6 | p21(CDKN1A)-activated kinase 6 | NM_020168 | Down | 2.5 | | | Ser/Thr | STE |
| *CAMK2D | Calcium/calmodulin-dependent protein kinase II-delta | NM_001221 | Down | 1.25 | 1.5 | 2 | Ser/Thr | CAMK |
| *CDC7L1 | CDC7 cell division cycle 7-like 1 | NM_003503 | Down | 1.25 | 2 | 3 | Ser/Thr | Other |

TABLE 1A-continued

| | | Serine/Threonine Kinases | | | | | | |
|---|---|---|---|---|---|---|---|---|
| Gene Name | Kinase Name | Genbank | Up/Down | # of SD | # of SD | # of SD | Kinase Family | Kinase Group |
| CDK5 | Cyclin-dependent kinase 5 | NM_004935 | Up | 1 | 1 | 1.25 | Ser/Thr | CMGC |
| PRKWNK1 | Protein kinase, lysine deficient 1 | NM_018979 | Up | 1 | 1.5 | 6.25 | Ser/Thr | Other |
| CDC42BPB | CDC42 binding protein kinase beta (DMPK-like) | NM_006035 | Up | 2.5 | 3.75 | | Ser/Thr | AGC |
| PRKCI | protein kinase C, iota | NM_002740 | Up | 1 | 1.75 | | Ser/Thr | AGC |
| PRKG1 | Protein kinase, cGMP-dependent, regulatory, Type I | NM_006258 | Up | 1 | 1.25 | | Ser/Thr | AGC |
| SMG1 | PI3-kinase-related kinase SMG1 | NM_015092 | Up | 1.25 | 1.5 | | Ser/Thr | Atypical |
| *BRD3 | Bromodomain-containing protein 3 | NM_007371 | Up | 1.25 | 1.75 | | Ser/Thr | Atypical |
| DAPK1 | Death-associated protein kinase 1 | NM_004938 | Up | 1 | 1.25 | 1.25 | Ser/Thr | CAMK |
| PASK | PAS domain containing serine/threonine kinase | NM_015148 | Up | 1 | 1 | | Ser/Thr | CAMK |
| LOC283629 | Chromosome 14 open reading frame 20; Testis-specific serine kinase 4 | NM_174944 | Up | 1 | 1.25 | | Ser/Thr/Tyr | CAMK |
| CDC2 | Cell division cycle 2, G1 to S and G2 to M | NM_001786 | Up | 1.25 | 2.75 | | Ser/Thr/Tyr | CMGC |
| MAPK13 | Mitogen-activated protein kinase 13 | NM_002754 | Up | 1 | 1.25 | 1.75 | Ser/Thr/Tyr | CMGC |
| STK35 | Serine/threonine kinase 35, Clik1 | NM_080836 | Up | 1 | 1.25 | 1.5 | Ser/Thr | Other |
| GAK | Cyclin G associated kinase | NM_005255 | Up | 1 | 1.25 | 1.75 | Ser/Thr | Other |
| ANKRD3 | ankyrin repeat domain 3 | NM_020639 | Up | 1 | 1.75 | | Ser/Thr/Tyr | TKL |
| IRAK3 | Interleukin-1 receptor-associated kinase 3 | NM_007199 | Up | 1.5 | 1.75 | | Ser/Thr | TKL |
| LIMK2 | LIM domain kinase 2 | NM_005569 | Up | 1 | 2 | | Ser/Thr/Tyr | TKL |
| PKMYT1 | Protein kinase, membrane-associated, tyrosine/threonine 1 | NM_004203 | Both | 1.25 | 1.5 | 1.75 | Ser/Thr/Tyr | Other |
| ADRBK2 | adrenergic, beta, receptor kinase 2 (GRK3; BARK2) | NM_005160 | Up | 2 | | | Ser/Thr | AGC |
| AKT3 | v-akt murine thymoma viral oncogene homolog 3 (protein kinase B, gamma) | NM_005465 | Up | 2 | | | Ser/Thr | AGC |
| CDK10 | cyclin-dependent kinase (CDC2-like) 10 | NM_003674 | Up | 5.75 | | | Ser/Thr/Tyr | CMGC |
| EIF2AK3 | eukaryotic translation initiation factor 2-alpha kinase 3 | NM_004836 | Up | 2.5 | | | Ser/Thr | Other |
| BIKE | BMP2 inducible kinase (BMP2K), transcript variant | NM_017593 | Up | 6 | | | Ser/Thr | Other |
| IKBKE | inhibitor of kappa light polypeptide gene enhancer in B-cells, kinase epsilon | NM_014002 | Up | 2 | | | Ser/Thr | Other |
| SDCCAG43 | serologically defined colon cancer antigen 43 | NM_006648 | Up | 4.25 | | | Ser/Thr/Tyr | Other |
| FLJ10074 | SCY1-like 2 (S. cerevisiae) | NM_017988 | Up | 2.25 | | | Ser/Thr | Other |
| FLJ32685 | hypothetical protein FLJ32685 | NM_152534 | Up | 3 | | | Ser/Thr/Tyr | Other |
| NEK11 | NIMA (never in mitosis gene a)-related kinase 11 | NM_024800 | Up | 4 | | | Ser/Thr/Tyr | Other |
| TTK | TTK protein kinase | NM_003318 | Up | 2.5 | | | Ser/Thr/Tyr | Other |

TABLE 1B

Tyrosine Kinases

| Gene Name | Kinase Name | Genbank | Up/Down | # of SD | # of SD | # of SD | Kinase Family | Kinase Group |
|---|---|---|---|---|---|---|---|---|
| PDGFRA | Platelet-derived growth factor receptor, alpha | NM_006206 | Down | 1.5 | 2 | | Tyr | TK |
| SRMS | src-related kinase lacking C-terminal regulatory tyrosine and N-terminal myristylation sites | NM_080823 | Down | 1.25 | 1.75 | | Tyr | TK |
| PTK6 | Protein tyrosine kinase 6 | NM_005975 | Down | 1.25 | 1.5 | | Tyr | TK |
| ZAP70 | zeta-chain (TCR) associated protein kinase 70kDa | NM_001079 | Down | 1.5 | 2 | | Tyr | TK |
| ERBB4 | v-erb-b2 erythroblastic leukemia viral oncogene homolog 4 (avian) | NM_005235 | Down | 1.25 | 1.5 | | Tyr | TK |
| IGF1R | insulin-like growth factor 1 receptor | NM_000875 | Down | 1 | 1.5 | | Tyr | TK |
| MET | met proto-oncogene (hepatocyte growth factor receptor) | NM_000245 | Down | 1 | 1.5 | | Tyr | TK |
| MERTK | c-mer proto-oncogene tyrosine kinase | NM_006343 | Down | 1 | 1.25 | | Tyr | TK |
| JAK2 | Janus kinase 2 (a protein tyrosine kinase) | NM_004972 | Down | 1 | 1.5 | | Tyr | TK |
| YES1 | v-yes-1 Yamaguchi sarcoma viral oncogene homolog 1 | NM_005433 | Up | 1.25 | 1.25 | | Tyr | TK |
| ERBB3 | v-erb-b2 erythroblastic leukemia viral oncogene homolog 3 (avian) | NM_001982 | Up | 1 | 1 | | Tyr | TK |
| EPHA7 | EphA7 | NM_004440 | Up | 1 | 1.25 | 1.5 | Tyr | TK |
| BTK | Bruton agammaglobulinemia tyrosine kinase | NM_000061 | Up | 1.25 | 1.5 | | Tyr | TK |
| EPHB3 | EphB3 | NM_004443 | Up | 1 | 1.75 | | Tyr | TK |
| RET | ret proto-oncogene (multiple endocrine neoplasia and medullary thyroid carcinoma 1, Hirschsprung disease) | NM_020975 | Up | 3 | | | Tyr | TK |

TABLE 1C

No Protein Phosphorylation Activity

| Gene Name | Kinase Name | Genbank | Up/Down | # of SD | # of SD | # of SD | Kinase Family | Kinase Group |
|---|---|---|---|---|---|---|---|---|
| C8FW | Tribbles homolog 1 | NM_025195 | Down | 1 | 1 | | X | CAMK |
| CHK | Choline kinase | NM_001277 | Down | 1 | 1.5 | | X | GO |
| FLJ13052 | NAD kinase | NM_023018 | Down | 1.25 | 1.75 | | X | GO |
| FLJ22055 | Phosphatidylinositol-4-phosphate 5-kinase, type II, gamma | NM_024779 | Down | 1 | 1 | | X | GO |
| CKMT2 | Creatine kinase, mitochondrial 2 (sarcomeric) | NM_001825 | Down | 1.75 | 2 | | X | GO |
| DKFZP586B1621 | DKFZP586B1621 protein, function unknown | NM_015533 | Down | 1 | 1.25 | | X | GO |
| GK | Glycerol kinase | NM_000167 | Down | 1.5 | 1.75 | | X | GO |
| ITPKC | Inositol 1,4,5-trisphosphate 3-kinase C | NM_025194 | Down | 1 | 1.25 | | X | GO |
| NME4 | Non-metastatic cells 4, protein expressed in | NM_005009 | Down | 1 | 1.25 | | X | GO |
| NM23-H6 | Non-metastatic cells 6, protein expressed in (nucleoside-diphosphate kinase) | NM_005793 | Down | 1.25 | 1.25 | 1.75 | X | GO |
| RBSK | Ribokinase | NM_022128 | Down | 2.25 | | | X | GO |
| ITPKC | Inositol 1,4,5-trisphosphate 3-kinase C | NM_025194 | Down | 1 | 1.25 | | X | GO |
| PMVK | Phosphomevalonate kinase | NM_006556 | Both | 1 | 1.25 | 2.5 | X | GO |

TABLE 1C-continued

No Protein Phosphorylation Activity

| Gene Name | Kinase Name | Genbank | Up/Down | # of SD | # of SD | # of SD | Kinase Family | Kinase Group |
|---|---|---|---|---|---|---|---|---|
| GS3955 | Tribbles homolog 2 | NM_021643 | Up | 1.25 | 1.25 | | X | CAMK |
| DGKI | diacylglycerol kinase, iota | NM_004717 | Up | 3 | | | X | GO |
| HK2 | hexokinase 2 | NM_000189 | Up | 2.25 | | | X | GO |
| DGKG | diacylglycerol kinase, gamma 90kDa | NM_001346 | Up | 2.25 | | | X | GO |
| NBP | Coenzyme A synthase (COASY), | NM_025233 | Up | 2.75 | | | X | GO |
| DGKA | Diacylglycerol kinase, alpha 80kDa | NM_001345 | Up | 1.5 | 1.75 | | X | GO |
| XYLB | Xylulokinase homolog (*H. influenzae*) | NM_005108 | Up | 1.25 | 3.5 | | X | GO |
| SPHK2 | Sphingosine kinase 2 | NM_020126 | Up | 1.5 | 2 | | X | GO |
| PRKRA | Protein kinase, interferon-inducible double stranded RNA dependent activator | NM_003690 | Up | 1 | 1 | 2.5 | X | GO |
| PIP5K2A | Phosphatidylinositol-4-phosphate 5-kinase, type II, alpha | NM_005028 | Up | 1 | 1 | | X | GO |

TABLE 2

Kinase whose inhibition modulates synuclein levels

| Gene Name | Kinase Name | Genbank | TF Plates | Up/Down | # of SD | # of SD | # of SD | Kinase Family | Kinase Group |
|---|---|---|---|---|---|---|---|---|---|
| PRKCD | protein kinase C, delta | NM_006254 | 1, 4, 7 | Down | 1 | 1.5 | | Ser/Thr | AGC |
| GPRK2L | G protein-coupled receptor kinase 2-like (*Drosophila*) | NM_005307 | 3, 6, 9 | Down | 1.25 | 1.5 | | Ser/Thr | AGC |
| GPRK5 | G protein-coupled receptor kinase 5 | NM_005308 | 3, 6, 9 | Down | 1.5 | 1.5 | 1.75 | Ser/Thr | AGC |
| AD034 | RIO kinase 1 (yeast) | NM_031480 | 10, 13, 16 | Down | 1.25 | 1.5 | | Ser/Thr | Atypical |
| BRDT | bromodomain, testis-specific | NM_001726 | 12, 15, 18 | Down | 1 | 1.25 | | Ser/Thr | Atypical |
| EEF2K | eukaryotic elongation factor-2 kinase | NM_013302 | 12, 15, 18 | Down | 1.5 | 2.25 | | Ser/Thr | Atypical |
| FASTK | Fas-activated serine/threonine kinase | NM_006712 | 12, 15, 18 | Down | 1.25 | 1.5 | | Ser/Thr | Atypical |
| LOC283629 | Testis-specific serine kinase 4 (TSSK4) | NM_174944 | 21, 24, 27 | Down | 1 | 1 | | Ser/Thr/Tyr | CAMK |
| STK22D | serine/threonine kinase 22D (spermiogenesis associated); TSSK1 | NM_032028 | 21, 24, 27 | Down | 1.25 | 1.25 | | Ser/Thr | CAMK |
| ALS2CR7 | amyotrophic lateral sclerosis 2 (juvenile) chromosome region, candidate 7 | NM_139158 | 28, 31, 34 | Down | 1 | 1.5 | | Ser/Thr | CMGC |
| CLK4 | CDC-like kinase 4 | NM_020666 | 30, 33, 36 | Down | 1 | 1.5 | | Ser/Thr/Tyr | CMGC |
| CDK5 | cyclin-dependent kinase 5 | NM_004935 | 30, 33, 36 | Down | 1 | 2 | | Ser/Thr | CMGC |
| CSNK2A2 | casein kinase 2, alpha prime polypeptide | NM_001896 | 55, 58, 61 | Down | 1 | 1.25 | 1.5 | Ser/Thr | Other |
| MAP2K4 | mitogen-activated protein kinase kinase 4 | NM_003010 | 65, 68, 71 | Down | 1 | 2 | | Ser/Thr/Tyr | STE |
| MAP2K1 | mitogen-activated protein kinase kinase 1 | NM_002755 | 65, 68, 71 | Down | 1 | 1.75 | | Ser/Thr/Tyr | STE |
| MAP2K5 | mitogen-activated protein kinase kinase 5 | NM_002757 | 66, 69, 72 | Down | 1 | 1.25 | | Ser/Thr/Tyr | STE |
| ANKRD3 | ankyrin repeat domain 3 (RIPK4) | NM_020639 | 83, 86, 89 | Down | 1 | 1.75 | | Ser/Thr | TKL |
| IRAK3 | interleukin-1 receptor-associated kinase 3 | NM_007199 | 83, 86, 89 | Down | 1 | 1.25 | | Ser/Thr | TKL |

TABLE 2-continued

Kinase whose inhibition modulates synuclein levels

| Gene Name | Kinase Name | Genbank | TF Plates | Up/Down | # of SD | # of SD | # of SD | Kinase Family | Kinase Group |
|---|---|---|---|---|---|---|---|---|---|
| BMPR2 | bone morphogenetic protein receptor, type II (serine/threonine kinase) | NM_001204 | 84, 87, 90 | Down | 1 | 2 | | Ser/Thr | TKL |
| PRKG2 | protein kinase, cGMP-dependent, type II | NM_006259 | 1, 4, 7 | Down | 2 | | | Ser/Thr | AGC |
| CHEK2 | CHK2 checkpoint homolog (S. pombe) | NM_007194 | 19, 22, 25 | Down | 3.25 | | | Ser/Thr | AGC |
| CDK9 | cyclin-dependent kinase 9 (CDC2-related kinase) | NM_001261 | 28, 31, 34 | Down | 2 | | | Ser/Thr | CMGC |
| CDK2 | cyclin-dependent kinase 2 | NM_001798 | 29, 32, 35 | Down | 2 | | | Ser/Thr | CMGC |
| CDKL3 | cyclin-dependent kinase-like 3 | NM_016508 | 29, 32, 35 | Down | 2.25 | | | Ser/Thr | CMGC |
| CDK10 | cyclin-dependent kinase (CDC2-like) 10 | NM_003674 | 29, 32, 35 | Down | 3 | | | Ser/Thr/Tyr | CMGC |
| CDK7 | cyclin-dependent kinase 7 (MO15 homolog, Xenopus laevis, cdk-activating kinase) | NM_001799 | 30, 33, 36 | Down | 2 | | | Ser/Thr | CMGC |
| PK428 | CDC42 binding protein kinase alpha (DMPK-like) | NM_003607 | 40, 46, 52 | Down | 2 | | | Ser/Thr/Tyr | GO |
| FLJ32685 | hypothetical protein FLJ32685 | NM_152534 | 57, 60, 63 | Down | 2.75 | | | Ser/Thr/Tyr | Other |
| NEK11 | NIMA (never in mitosis gene a)-related kinase 11 | NM_024800 | 57, 60, 63 | Down | 3.5 | | | Ser/Thr/Tyr | Other |
| JIK | TAO Kinase 3 (MAP3K18) | NM_016281 | 64, 67, 70 | Down | 2 | | | Ser/Thr | STE |
| PAK6 | p21(CDKN1A)-activated kinase 6 | NM_020168 | 65, 68, 71 | Down | 2.25 | | | Ser/Thr | STE |
| KSR | kinase suppressor of ras | NM_013571 | 83, 86, 89 | Down | 2.25 | | | Ser/Thr/Tyr | TKL |
| AMHR2 | anti-Mullerian hormone receptor, type II | NM_020547 | 83, 86, 89 | Down | 2 | | | Ser/Thr/Tyr | TKL |
| LIMK2 | LIM domain kinase 2 | NM_005569 | 84, 87, 90 | Down | 2 | | | Ser/Thr/Tyr | TKL |
| BCR | breakpoint cluster region | NM_004327 | 11, 14, 17 | Both | 1 | 1.25 | 1.5 | Ser/Thr | Atypical |
| ROCK2 | Rho-associated, coiled-coil containing protein kinase 2 | NM_004850 | 2, 5, 8 | Up | 1 | 1 | | Ser/Thr/Tyr | AGC |
| SGK2 | serum/glucocorticoid regulated kinase 2 | NM_170693 | 2, 5, 8 | Up | 1.25 | 1.5 | | Ser/Thr | AGC |
| SGKL | serum/glucocorticoid regulated kinase-like | NM_013257 | 2, 5, 8 | Up | 1.25 | 1.25 | | Ser/Thr/Tyr | AGC |
| pknbeta | protein kinase N3 | NM_013355 | 3, 6, 9 | Up | 1 | 1.75 | | Ser/Thr | AGC |
| PRKCH | protein kinase C, eta | NM_006255 | 3, 6, 9 | Up | 1 | 1.75 | | Ser/Thr | AGC |
| ROS1 | v-ros UR2 sarcoma virus oncogene homolog 1 (avian) | NM_002944 | 10, 13, 16 | Up | 1 | 1.5 | | Ser/Thr/Tyr | TK |
| CAMK1 | calcium/calmodulin-dependent protein kinase I | NM_003656 | 20, 23, 26 | Up | 1.25 | 2 | | Ser/Thr | CAMK |
| CAMK2B | calcium/calmodulin-dependent protein kinase (CaM kinase) II beta | NM_172078 | 20, 23, 26 | Up | 1.5 | 1.75 | | Ser/Thr/Tyr | CAMK |
| CAMK2D | calcium/calmodulin-dependent protein kinase (CaM kinase) II delta | NM_001221 | 21, 24, 27 | Up | 1.5 | 2.25 | | Ser/Thr | CAMK |
| STK22B | serine/threonine kinase 22B (spermiogenesis associated) | NM_053006 | 21, 24, 27 | Up | 1.25 | 1.25 | | Ser/Thr/Tyr | CAMK |
| STK29 | serine/threonine kinase 29 | NM_003957 | 21, 24, 27 | Up | 1 | 2 | | Ser/Thr/Tyr | CAMK |

TABLE 2-continued

Kinase whose inhibition modulates synuclein levels

| Gene Name | Kinase Name | Genbank | TF Plates | Up/Down | # of SD | # of SD | # of SD | Kinase Family | Kinase Group |
|---|---|---|---|---|---|---|---|---|---|
| DYRK1B | dual-specificity tyrosine-(Y)-phosphorylation regulated kinase 1B | NM_004714 | 28, 31, 34 | Up | 1 | 1.25 | | Ser/Thr/Tyr | CMGC |
| PCTK1 | PCTAIRE protein kinase 1 | NM_033018 | 28, 31, 34 | Up | 1 | 1.25 | | Ser/Thr | CMGC |
| SRPK2 | SFRS protein kinase 2 | NM_182692 | 30, 33, 36 | Up | 1 | 1.25 | | Ser/Thr/Tyr | CMGC |
| NEK7 | NIMA (never in mitosis gene a)-related kinase 7 | NM_133494 | 55, 58, 61 | Up | 1 | 1 | | Ser/Thr/Tyr | Other |
| PACE-1 | SCY1-like 3 (*S. cerevisiae*) | NM_020423 | 56, 59, 62 | Up | 1 | 1.5 | | Ser/Thr | Other |
| CNK | cytokine-inducible kinase (polo-like kinase 3-*Drosophila*) | NM_004073 | 57, 60, 63 | Up | 1.25 | 2 | | Ser/Thr | Other |
| TTBK | tau tubulin kinase 2 | NM_173500 | 84, 87, 90 | Up | 1.25 | 1.25 | | Ser/Thr/Tyr | CK1 |
| PRKCZ | protein kinase C, zeta | NM_002744 | 3, 6, 9 | Up | 2 | | | Ser/Thr | AGC |
| TTK | TTK protein kinase | NM_003318 | 64, 67, 70 | Up | 2.25 | | | Ser/Thr/Tyr | Other |
| ZAP70 | zeta-chain (TCR) associated protein kinase 70 kDa | NM_001079 | 66, 69, 72 | Down | 1.25 | 2 | | Tyr | TK |
| FLT3 | fms-related tyrosine kinase 3 | NM_004119 | 73, 76, 79 | Down | 1 | 1 | | Tyr | TK |
| HCK | hemopoietic cell kinase | NM_002110 | 74, 77, 80 | Down | 1.5 | 1.75 | | Tyr | TK |
| BMX | BMX non-receptor tyrosine kinase | NM_001721 | 74, 77, 80 | Down | 1.25 | 1.5 | | Tyr | TK |
| BTK | Bruton agammaglobulinemia tyrosine kinase | NM_000061 | 74, 77, 80 | Down | 1 | 1 | | Tyr | TK |
| DDR2 | discoidin domain receptor family, member 2 | NM_006182 | 75, 78, 81 | Down | 1 | 1.25 | | Tyr | TK |
| CSF1R | colony stimulating factor 1 receptor, formerly McDonough feline sarcoma viral (v-fms) oncogene homolog | NM_005211 | 75, 78, 81 | Down | 2 | | | Tyr | TK |
| LCK | lymphocyte-specific protein tyrosine kinase | NM_005356 | 39, 45, 51 | Both | 1 | 1.25 | 1.5 | Tyr | GO |
| PRKCA | protein kinase C, alpha | NM_002737 | 1, 4, 7 | Up | 1 | 1.25 | | Tyr | AGC |
| ROR2 | receptor tyrosine kinase-like orphan receptor 2 | NM_004650 | 10, 13, 16 | Up | 1 | 1 | 1 | Tyr | TK |
| PDGFRA | platelet-derived growth factor receptor, alpha polypeptide | NM_006206 | 11, 14, 17 | Up | 1 | 1.25 | | Tyr | TK |
| SRMS | src-related kinase lacking C-terminal regulatory tyrosine and N-terminal myristylation sites | NM_080823 | 11, 14, 17 | Up | 1.25 | 1.25 | | Tyr | TK |
| TXK | TXK tyrosine kinase | NM_003328 | 12, 15, 18 | Up | 1 | 1.5 | | Tyr | TK |
| YES1 | v-ros UR2 sarcoma virus oncogene homolog 1 (avian) | NM_005433 | 66, 69, 72 | Up | 1.25 | 1.25 | | Tyr | TK |
| DKFZp61P1010 | serine/threonin/tyrosine kinase 1 (STYK1) | NM_018243 | 73, 76, 79 | Up | 1.25 | 1.25 | | Tyr | TK |
| EPHA2 | EphA3 | NM_004431 | 73, 76, 79 | Up | 1 | 1.5 | | Tyr | TK |
| FGR | Gardner-Rasheed feline sarcoma viral (v-fgr) oncogene homolog | NM_005248 | 75, 78, 81 | Up | 1 | 1.25 | | Tyr | TK |

TABLE 2-continued

Kinase whose inhibition modulates synuclein levels

| Gene Name | Kinase Name | Genbank | TF Plates | Up/Down | # of SD | # of SD | # of SD | Kinase Family | Kinase Group |
|---|---|---|---|---|---|---|---|---|---|
| FLT1 | fms-related tyrosine kinase 1 (vascular endothelial growth factor/vascular permeability factor receptor) | NM_002019 | 75, 78, 81 | Up | 1.25 | 1.5 | | Tyr | TK |
| EPHB3 | EphB3 | NM_004443 | 75, 78, 81 | Up | 1 | 1.25 | | Tyr | TK |
| CSS3R | colony stimulating factor 1 receptor, formerly McDonough feline sarcoma viral (v-fms) oncogene homolog | NM_005211 | 38, 44, 50 | Up | 2.75 | | | Tyr | GO |
| GUCY2C | guanylate cyclase 2C (heat stable enterotoxin receptor) | NM_004963 | 57, 60, 63 | Up | 2.25 | | | Tyr | Other |
| BCKDK | branched chain ketoacid dehydrogenase kinase | NM_005881 | 10, 13, 16 | Down | 1.25 | 1.5 | 2.25 | ? | Atypical |
| BRD4 | bromodomain containing 4 | NM_014299 | 11, 14, 17 | Down | 1.75 | 2 | | ? | Atypical |
| AK3 | adenylate kinase 3 | NM_013410 | 37, 43, 49 | Down | 1 | 1.25 | | X | GO |
| FLJ12476 | hypothetical protein FLJ12476 | NM_022784 | 39, 45, 51 | Down | 1 | 1.25 | | ? | GO |
| PAPSS2 | 3-phosphoadenosine 5-phosphosulfate synthase 2 | NM_004670 | 42, 48, 54 | Down | 1 | 1.5 | | ? | GO |
| C20orf97 | chromosome 20 open reading frame 97 (Tribbles homolog 3) | NM_021158 | 19, 22, 25 | Down | 2 | | | X | CAMK |
| C8FW | Tribbles homolog 1 | NM_025195 | 19, 22, 25 | Down | 2 | | | X | CAMK |
| GS3955 | Tribbles homolog 2 | NM_021643 | 20, 23, 26 | Down | 2 | | | X | CAMK |
| FLJ32704 | chromosome 9 open reading frame 98 | NM_157572 | 37, 43, 49 | Down | 3.75 | | | X | GO |
| DCK | deoxycytidine kinase | NM_000788 | 38, 44, 50 | Down | 2.25 | | | X | GO |
| KIAA0626 | microfibrillar-associated protein 3-like | NM_021647 | 39, 45, 51 | Down | 2.5 | | | X | GO |
| XYLB | Xylulokinase homolog (*H. influenzae*) | NM_005108 | 40, 46, 52 | Down | 3 | | | X | GO |
| UCK1 | uridine-cytidine kinase 1 | NM_031432 | 42, 48, 54 | Down | 2 | | | X | GO |
| GUK1 | guanylate kinase 1 | NM_000858 | 39, 45, 51 | Both | 1 | 2 | 2.75 | ? | GO |
| MGC26954 | chromosome 6 open reading frame 199 | NM_145025 | 40, 46, 52 | Both | 1 | 1 | 1.25 | ? | GO |
| HK1 | hexokinase 1 | NM_033498 | 37, 43, 49 | Up | 2.25 | 2.75 | | X | GO |
| CALM3 | calmodulin 3 (phosphorylase kinase, delta) | NM_005184 | 38, 44, 50 | Up | 2 | 2.25 | | X | GO |
| RBSK | ribokinase | NM_022128 | 40, 46, 52 | Up | 1.25 | 1.5 | | X | GO |
| PANK1 | pantothenate kinase 1 | NM_148978 | 41, 47, 53 | Up | 1.5 | 1.5 | | X | GO |
| P15RS | hypothetical protein FLJ10656 | NM_018170 | 41, 47, 53 | Up | 1 | 1.5 | | ? | GO |
| PFKFB2 | 6-phosphofructo-2-kinase/fructose-2,6-biphosphatase 2 | NM_006212 | 42, 48, 54 | Up | 1 | 1.25 | | ? | GO |
| CKMT2 | Creatine kinase, mitochondrial 2 (sarcomeric) | NM_001825 | 38, 44, 50 | Up | 3.5 | | | X | GO |
| PGK1 | phosphoglycerate kinase 1 | NM_000291 | 40, 46, 52 | Up | 2.5 | | | X | GO |

EXAMPLE 2

Verification of Alpha-Synuclein Phosphorylation Modulation by Re-Screening and by qRT-PCR The kinases that showed either an increase or decrease in alpha-synuclein phosphorylation from Example 1 were retested to verify the effect on alpha-synuclein. The confirmation screen was performed using 10 nM siRNA on the targets identified in Example 1 along with several additional kinases of interest. The higher concentration of siRNA in Example 1 was used to ensure that marginal knockdown caused by poorly designed siRNAs could be observed. By using a much lower siRNA concentration in the confirmation screens, the chance of effects due to a general response to the siRNA itself could be much reduced. Some siRNAs that were later reported by Ambion to be ineffective were also re-screened (see replacement library screen below). Finally, some newly identified kinases were screened and those results were added to the pool of results. The kinases that were identified as candidates were tested by quantitative RT-PCR (qRT-PCR) to confirm that they were actually present in the PEAK-Syn cells (see Example 6). The experimental procedures and results for the confirmation and rescreening were as follows:

Confirmation Screen

The results for the confirmation screen were grouped into four categories shown below:

Completely Confirmed: This category included the kinases for which all three siRNAs produced identical phenotypes in the 10 nM screen and in the 100 nM screen.

Mostly Confirmed: This category included the kinases for which ⅔ of the siRNAs produced identical phenotypes in the 10 nM and in the 100 nM screen, but one third did not; or, alternatively one siRNA result was replicated, but for a second siRNA there was a trend for the same phenotype but with a different siRNA from that used in the original screen.

Partly Confirmed: This category included the kinases for which ⅓ of the siRNAs produced the same phenotype in the 10 nM screen and in the 100 nM screen.

Not Confirmed: This category included the kinases for which either or both of the following occurred:
  a) None of the three siRNAs had any effect on phosphor-alpha-synuclein levels at 10 nM, and/or
  b) The siRNAs produced the opposite phenotype to what was observed in the primary 100 nM screen The number of kinases that fell into each category was tabulated and the results are shown in Table 3. Seven kinases were completely confirmed, and they are listed in Table 4. Of these seven, only three were identified as possessing the qualities to be good candidates for a kinase that directly phosphorylates alpha-synuclein at ser-129. This is because only three were both ser/thr kinases and decreased phospho alpha-synuclein levels when the kinase levels were reduced by the specific siRNA. These included: APEG1, which is believed to play a role in growth and differentiation of smooth muscle, PLK2 (SNK), which is expressed in brain and is believed to play a role in normal cell division, and CDC7L1, a cell division cycle protein with kinase activity. Of the three, PLK2 was of the most interest due to its role and localization in cells, such as activated neurons. Alpha-synuclein is a synaptic-associated protein thought to be involved in synaptic plasticity and vesicular transport. Thus, PLK2 was identified as a very good candidate for a kinase that directly phosphorylates α-synuclein.

TABLE 3

Breakdown of Candidate Hits From 10 nM Confirmation Screen

| Hit Category | Number of Hits |
| --- | --- |
| Completely Confirmed | 7 |
| Mostly Confirmed | 29 |
| Partly Confirmed | 22 |
| No Reactivity at 10 nM | 19 |
| Opposite Reaction to Primary Screen | 23 |
| Total Number Of Hits Re-Screened at 10 nM | 100 |

NOTES:

For all subsequent tables

*** denotes where a replacement siRNA has been analyzed and the new data substituted for that from the ineffective siRNA Key to shading:

| |
| --- |
| Significant decrease in phospho-synclein compared to controls |
| Significant increase in phospho-synuclein compared to controls |

TABLE 4

Completely Confirmed Hits

| | | Number of SD | | | | |
| --- | --- | --- | --- | --- | --- | --- |
| Gene Name | Kinase Name | siRNA A | siRNA B | siRNA C | Kinase Family | Kinase Group |
| APEG1 | Aortic preferentially expressed gene 1 | 1.5 | 1.25 | 1 | Ser/Thr/Tyr | CAMK |
| PLK2/SNK | Polo like kinase 2 | 1.5 | 1.75 | 3.25 | Ser/Thr | Other |
| CDLC7L1 | CDC7 cell division cycle 7-like 1 | 2.5 | 1.5 | 1.75 | Ser/Thr | Other |
| PRKG1 | Protein kinase, cGMP-dependent, regulartory, Type I | 1.5 | | 1.75 | Ser/Thr | AGC |
| MAPK13 | Mitogen-activated protein kinase 13 | 2.75 | 6.7 | 4.5 | Ser/Thr/Tyr | CMGC |
| GAK | Cyclin G associated kinase | 2.25 | | | Ser/Thr | Other |
| MET | met proto-oncogene (hepatocyte growth factor receptor) | 1.5 | 1.25 | | Tyr | TK |

Table 4 shows the seven candidates whose results were completely replicated at 10 nM. Only the first three were identified as having strong potential to be a direct kinase, because they are ser/thr kinases that reduce phospho-synuclein levels when the kinase level is reduced.

There were 29 kinases that fell into the mostly confirmed category, 12 of which were candidates for a direct kinase. These are listed in Table 5. There were 17 additional kinases that were mostly confirmed at 10 nM. Although not likely to be a direct kinase, these could play a role in the regulation of a direct kinase and are listed in Table 6. Twenty-two kinases fell into the partly confirmed category. The ser/thr kinases that decreased phospho alpha-synuclein (i.e. potentially a direct kinase for alpha-synuclein) are listed in Table 8, and the remaining potentially regulatory kinases are listed in Table 8.

TABLE 5

Potential Direct Serine/Threonine Kinases that Mostly Confirmed at 10 nM siRNA

| Gene Name | Kinase Name | Number of SD | | | Kinase Family | Kinase Group |
| --- | --- | --- | --- | --- | --- | --- |
| | | siRNA A | siRNA B | siRNA C | | |
| FLJ11159 | RIO kinase 2 (yeast) | 2 | *** | *** | Ser/Thr | Atypical |
| ARK5 | AMP-activated protein kinase family member 5 | | 1.25 | 1 | Ser/Thr | CAMK |
| CAMK1 | Calcium/calmodulin-dependent protein kinase I | | 1.25 | 1.75 | Ser/Thr | CAMK |
| CDC2L5 | Cell division cycle 2-like 5 | 2.25 | | | Ser/Thr/Tyr | CMGC |
| ERK8 | Extracellular signal-regulated kinase 8 | 2.25 | 1.25 | 1 | Ser/Thr | CMGC |
| CKIIA2 | Casein kinase 2, alpha prime subunit | 2 | 1 | 2.5 | Ser/Thr | Other |
| MAP2K4 | mitogen-activated protein kinase kinase 4 (MEK4; MKK4; JNKK) | | 2.75 | 1 | Ser/Thr/Tyr | STE |
| MAP2K5 | mitogen-activated protein kinase kinase 5 (MEK5; MKK5) | 1.25 | 2*** | | Ser/Thr/Tyr | STE |
| RIPK3 | receptor-interacting serine-threonine kinase 3 | 2.25 | | | Ser/Thr/Tyr | TKL |
| PRKG2 | protein kinase, cGMP-dependent, type II | 1 | 1.75 | | Ser/Thr | AGC |
| ADRBK1 | adrenergic, beta, receptor kinase 1 (GRK2; BARK1) | | 1.25 | 1.75 | Ser/Thr | AGC |
| RHOK | rhodopsin kinase; G protein-coupled receptor kinase 1; GRK1 | 1.25*** | 2.25*** | | Ser/Thr | AGC |

The ser/thr kinases shown in Table 5 were identified as having potential to be a direct kinase that phosphorylates alpha-synuclein because they significantly reduced phospho-synuclein levels when the kinase level was reduced. ⅔ of the siRNAs produced identical results at 10 nM as they did at 100 nM, and as such, were designated as Mostly Confirmed hits.

The kinases in Table 6 were designated as Mostly Confirmed, because ⅔ of the siRNAs produced identical results at 10 nM and 100 nM concentration of siRNA. However, because they did not produce the appropriate phenotype or were the wrong class of kinase (i.e. tyr or non-protein kinase as opposed to a ser/thr kinase), they were identified as not likely to be a direct kinase that phosphorylates ser-129 on alpha-synuclein. Instead, they may be upstream modulators of alpha-synuclein phosphorylation.

TABLE 6

Other Kinases That Were Mostly Confirmed at 10 nM sirRNA

| Gene Name | Kinase Name | Number of SD | | | Kinase Family | Kinase Group |
| --- | --- | --- | --- | --- | --- | --- |
| | | siRNA A | siRNA B | siRNA C | | |
| CDC42BPB | CDC42 binding protein kinase beta (DMPK-like) | | 3 | | Ser/Thr | AGC |
| PRKCI | protein kinase C, iota | 2 | 1.25 | 1.5*** | Ser/Thr | AGC |
| SMG1 | PI3-kinase-related kinase SMG1 | 3.75 | | 1 | Ser/Thr | Atypical |
| PASK | PAS domain containing serine/threonine kinase | *** | | 1.25 | Ser/Thr | CAMK |
| CDC2 | Cell division cycle 2, G1 to S and G2 to M | | 3 | 1.5 | Ser/Thr/Tyr | CMGC |
| ANKRD3 | ankyrin repeat domain 3 | | 2.25 | | Ser/Thr/Tyr | TKL |
| ADRBK2 | adrenergic, beta, receptor kinase 2 (GRK3; BARK2) | | 6.25 | 1.25 | Ser/Thr | AGC |
| AKT3 | v-akt murine thymoma viral oncogene homolog 3 (protein kinase B, gamma | 1 | 6.25 | 2*** | Ser/Thr | AGC |
| SDCCAG43 | serologically defined colon cancer antigen 43 | 2.25 | 1 | | Ser/Thr/Tyr | Other |

TABLE 6-continued

| Gene | Kinase Name | siRNA A | siRNA B | siRNA C | Family | Group |
|---|---|---|---|---|---|---|
| ERBB4 | v-erb-b2 erythroblastic leukemia viral oncogene homolog 4 (avian) | 1.75 | 1.75 | | Tyr | TK |
| MERTK | c-mer proto-oncogene tyrosine kinase | | | 1.5 | Tyr | TK |
| ERBB3 | v-erb-b2 erythroblastic leukemia viral oncogene homolog 3 (avian) | | 1.75 | | Tyr | TK |
| CHK | Choline kinase | | 1.75 | | Non-protein | GO |
| CKMT2 | Creatine kinase, mitochondrial 2 (sarcomeric) | | 2.5 | 1.25 | Non-protein | GO |
| NM23-H6 | Non-metastatic cells 6, protein expressed in (nucleoside-diphosphate kinase) | 1.5 | | 1.5 | Non-protein | GO |
| RBSK | Ribokinase | 2 | 1.75 | 2.25 | Non-protein | GO |
| SPHK2 | Sphingosine kinase 2 | 1.5 | 1 | | Non-protein | GO |

TABLE 7

Potential Direct Serine/Threonine Kinases that Partly Confirmed at 10 nM siRNA

| | | Number of SD | | | | |
|---|---|---|---|---|---|---|
| Gene Name | Kinase Name | siRNA A | siRNA B | siRNA C | Kinase Family | Kinase Group |
| GPRK6 | G protein-coupled receptor kinase 6 | | 1.25 | 1 | Ser/Thr | AGC |
| PDPK1 | 3-Phosphoinositide dependent protein kinase-1 | | 2.75 | 1 | Ser/Thr | AGC |
| PRKAA2 | Protein kinase, AMP-activated, alpha 2 catalytic subunit | 1 | 4.75 | 1 | Ser/Thr | CAMK |
| CDK8 | Cyclin-dependent kinase 8 | 2.25 | | | Ser/Thr | CMGC |
| CKIIA1 | Casein kinase 2, alpha subunit | 3.5 | | | Ser/Thr | Other |
| TESK2 | testis-specific kinase 2 | *** | 1.5 | | Ser/Thr/Tyr | TKL |
| JIK | TAO Kinase 3 (MAP3K18) | 1.25 | 1.25 | 1.5 | Ser/Thr | STE |
| PAK6 | p21(CDKN1A)-activated kinase 6 | | | 1 | Ser/Thr | STE |

The ser/thr kinases in Table 7 were identified as having potential to be a direct kinase that phosphorylates alpha-synuclein because they significantly reduced phospho-synuclein levels when the kinase levels were reduced. Only ⅓ of the siRNAs produced identical results at 10 nM as they did at 100 nM, and as such, were designated as Partly Confirmed hits.

Several candidates had contradictory results and, thus, were identified as having less potential to be a direct kinase for alpha-synuclein.

TABLE 8

Other Kinases That Were Partly Confirmed at 10 nM siRNA

| Gene Name | Kinase Name | siRNA A | siRNA B | siRNA C | Kinase Family | Kinase Group |
|---|---|---|---|---|---|---|
| CDK5 | Cyclin-dependent kinase 5 | 2.25 | | 1 | Ser/Thr | CMGC |
| PRKWNK1 | Protein kinase, lysine deficient 1 | | 1.75 | 1 | Ser/Thr | Other |
| DAPK1 | Death-associated protein kinase 1 | | 3.5 | | Ser/Thr | CAMK |
| STK35 | Serine/threonine kinase 35, Clik1 | 1.25 | 1.25 | | Ser/Thr | Other |
| PKMYT1 | Protein kinase, membrane-associated, tyrosine/threonine 1 | 5.75 | 1.5 | | Ser/Thr/Tyr | Other |
| IKBKE | inhibitor of kappa light polypeptide gene enhancer in B-cells, kinase epsilon | | 1.5 | | Ser/Thr | Other |
| RET | ret proto-oncogene (multiple endocrine neoplasia and medullary thyroid carcinoma 1, Hirschsprung dis) | 3.75 | 8.25 | 1.75 | Tyr | TK |
| FLJ13502 | NAD kinase | | | 1.25 | Non-protein | GO |
| DKFZP586B1621 | DKFZP586B1621 protein, function unknown | 1.5 | | 1.25 | Non-protein | GO |
| ITPKC | Inositol 1,4,5-trisphosphate 3-kinase C | | 2 | 1.5 | Non-protein | GO |
| PMVK | Phosphomevalonate kinase | 1.75 | | 2 | Non-protein | GO |
| NBP | Coenzyme A synthase (COASY), | 1 | 5.75*** | | Non-protein | GO |
| PRKRA | Protein kinase, interferon-inducible double stranded RNA dependent activator | | 1 | | Non-protein | GO |
| PIP5K2A | Phosphatidylinositol-4-phosphate 5-kinase, type II, alpha | | 1.5 | | Non-protein | GO |

The kinases in Table 8 were identified as having less potential to be direct kinases in the phosphorylation of alpha-synuclein at ser-129 but could be upstream modulators of alpha-synuclein phosphorylation. ⅓ of the siRNAs produced identical results at 10 nM as they did at 100 nM, and as such, were designated as Partly Confirmed hits. However, several had contradictory results and, thus, were designated as having less potential to be direct kinases of alpha-synuclein.

Forty-two kinases did not have their initial results confirmed at 10 nM. Of these, 19 fell into category (a) listed above, and are listed in Table 9. At 10 nM, none of the three siRNAs at 10 nM produced any change in the phospho-alpha-synuclein phenotype, indicating that the results for these kinases from the 100 nM screen were possibly due to off-target effects. Twenty-three kinases (Table 10) produced the opposite effect on phospho-alpha-synuclein levels at 10 nM than at 100 nM siRNA. There is a possibility that the results at 10 nM were the true effects due to the fact that at 100 nM results are sometimes masked by off-target effects. This can happen at the much higher siRNA concentration. Alternatively, the true effect may have been seen at the higher concentration. In any case, these kinases were designated as less likely to be direct kinases of alpha-synuclein.

The nineteen kinases shown in Table 9 had no significant reactivity at 10 nM compared to controls. Thus, it is possible that the change in phospho-synuclein levels observed at 100 nM was due to off-target effects caused by high concentrations of siRNA. GPRK5 and GPRK7 were not candidates in the original 100 nM screen, but were analyzed at 10 nM siRNA because of additional interest in their role in alpha-synuclein phosphorylation.

TABLE 9

Kinases That Had No Reactivity at 10 nM siRNA

| Gene Name | Kinase Name | siRNA A | siRNA B | siRNA C | Kinase Family | Kinase Group |
|---|---|---|---|---|---|---|
| CAMK2D | Calcium/calmodulin-dependent protein kinase II-delta | | *** | | Ser/Thr | CAMK |
| CDK4 | Cyclin-dependent kinase 4 | | | | Ser/Thr** | CMGC |
| CLK3 | CDC-like kinase 3 | | | | Ser/Thr/Tyr | CMGC |
| PRP4 | Pre-mRNA processing factor 4 homolog B (yeast) | | | | Ser/Thr | GO |
| JAK2 | Janus kinase 2 (a protein tyrosine kinase) | | | | Tyr | TK |
| CDK10 | cyclin-dependent kinase (CDC2-like) 10 | | | | Ser/Thr/Tyr | CMGC |
| FLJ10074 | SCY1-like 2 (S. cerevisiae) | *** | *** | *** | Ser/Thr | Other |
| FLJ32685 | hypothetical protein FLJ32685 | *** | | | Ser/Thr/Tyr | Other |
| NEK11 | NIMA (never in mitosis gene a)-related kinase 11 | | | | Ser/Thr/Tyr | Other |
| GPRK7 | G protein-coupled receptor kinase 7; GRK7 | No siRNA | 2 | 2 | Ser/Thr | AGC |
| GPRK5 | G protein-coupled receptor kinase 5; GRK5 | *** | | 1.25 | Ser/Thr | AGC |
| PDGFRA | Platelet-derived growth factor receptor, alpha | | | | Tyr | TK |
| PTK6 | Protein tyrosine kinase 6 | | | | Tyr | TK |
| IGF1R | insulin-like growth factor 1 receptor | *** | | | Tyr | TK |
| EPHB3 | EphB3 | | | | Tyr | TK |
| YES1 | v-yes-1 Yamaguchi sarcoma viral oncogene homolog 1 | | | | Tyr | TK |
| C8FW | Tribbles homolog 1 | | | | Non-protein | CAMK |
| FLJ22055 | Phosphatidylinositol-4-phosphate 5-kinase, type II, gamma | | | | Non-protein | GO |
| DGKA | Diacylglycerol kinase, alpha 80kDa | | | | Non-protein | GO |

The results for the kinases in Table 10 were not confirmed at 10 nM because they had the opposite effect on phospho-synuclein levels from that seen at 100 nM. However, it is possible that the results at 10 nM siRNA were the true results, and that the high concentration (100 nM) of siRNA was masking the true effects. It is also possible that the initial effects observed at 100 nM were the true effects. These were designated as likely to be direct kinases of alpha-synuclein and set aside to be tested further at a later date.

TABLE 10

Kinases Whose Results Were Opposite To The Primary Screen

| Gene Name | Kinase Name | siRNA A | siRNA B | siRNA C | Kinase Family | Kinase Group |
|---|---|---|---|---|---|---|
| SSTK | Serine/threonine protein kinase SSTK | 1.25 | | | Ser/Thr | CAMK |
| PHKG2 | Phosphorylase kinase, gamma 2 (testis) | 1*** | *** | *** | Ser/Thr | CAMK |
| CASK | Calcium/calmodulin-dependent serine protein kinase | 1.75 | | | Ser/Thr | CAMK |
| MAP2K1 | mitogen-activated protein kinase kinase 1 (MEK1; MKK1) | 2 | | 1.5 | Ser/Thr/Tyr | STE |
| BRD3 | Bromodomain-containing protein 3 | | *** | 1*** | Ser/Thr | Atypical |
| LOC283629 | Chromosome 14 open reading frame 20; Testis-specific serine kinase 4 | 1.75 | | | Ser/Thr/Tyr | CAMK |
| IRAK3 | Interleukin-1 receptor-associated kinase 3 | 1.25 | 1.75 | | Ser/Thr | TKL |
| LIMK2 | LIM domain kinase 2 | 2.25 | | | Ser/Thr/Tyr | TKL |
| EIF2AK3 | eukaryotic translation initiation factor 2-alpha kinase 3 | 2.5 | 1.75 | | Ser/Thr | Other |
| BIKE | BMP2 inducible kinase (BMP2K), transcript variant | 3.75 | 1 | 1.5 | Ser/Thr | Other |
| TTK | TTK protein kinase | | 1.5 | 1.25 | Ser/Thr/Tyr | Other |
| GPRK2L | G protein-coupled receptor kinase 2 like; GRK4 | | | 1 | Ser/Thr | AGC |
| SRMS | src-related kinase lacking C-terminal regulatory tyrosine and N-terminal myristylation sites | | 2.75 | 3.5 | Tyr | TK |
| ZAP70 | zeta-chain (TCR) associated protein kinase 70kDa | 1.5*** | *** | | Tyr | TK |

TABLE 10-continued

| Gene | Name | col3 | col4 | col5 | Type | Family |
|---|---|---|---|---|---|---|
| EPHA7 | EphA7 | | 1.5 | | Tyr | TK |
| BTK | Bruton agammaglobulinemia tyrosine kinase | 1.5 | | 1 | Tyr | TK |
| GK | Glycerol kinase | | 1.25 | | Non-protein | GO |
| NME4 | Non-metastatic cells 4, protein expressed in | *** | 4 | | Non-protein | GO |
| GS3955 | Tribbles homolog 2 | | 1 | 1.25 | Non-protein | CAMK |
| DGKI | diacylglycerol kinase, iota | 1.25 | | | Non-protein | GO |
| HK2 | hexokinase 2 | | | 1 | Non-protein | GO |
| DGKG | diacylglycerol kinase, gamma 90kDa | | 1.5 | | Non-protein | GO |
| XYLB | Xylulokinase homolog (H. influenzae) | 1 | | | Non-protein | GO |

Replacement and Up-Dated Library Screens

Because some siRNAs used in the initial screen were later identified as being of poor quality, screens were performed at both concentrations with replacement siRNAs. The data for the replacement siRNAs was used to replace the data for that specific siRNA result from the original screen. Statistical data was tabulated for the three siRNAs for each kinase, and using this, nine additional kinases were identified as candidates from the original screen that were missed in the primary screen. These were retested, and two of the kinases were partially confirmed at 10 nM siRNA. These were BCKDK and FLJ25965 (KSR2).

During the process, a number of new kinases were identified and siRNAs became available. These were tested as in Example 1 as an AMBION Up-Dates library and new kinase candidates were identified. Many of the newly identified kinases fell under the GO (Gene Ontology Consortium) classification. As such, it was difficult to find detailed information on some of these kinases. Several of the genes included in this category were not true kinases, but were kinase binding proteins or adaptor proteins. At 10 nM siRNA, thirteen kinases were confirmed to be candidates for directly acting on alpha-synuclein. Two of these were likely candidates for being a direct kinase, see Table 11. The remaining eleven were designated as possible indirect regulators of phospho-synuclein levels, see Table 11. Table 11 provides Genbank accession numbers for the kinase sequences as deposited in Genbank as of Nov. 1, 2005.

TABLE 11

Potential Kinase Hits From the Ambion Updates Library

| Gene Name | Genbank # | Kinase Name | siRNA A | siRNA B | siRNA C | Kinase Family |
|---|---|---|---|---|---|---|
| IKBKB | NM_001556 | inhibitor of kappa light polypeptide gene enhancer in B-cells, kinsase beta | 1.75 | 1.25 | | Ser/Thr |
| PRKAG1 | NM_212461 | protein kinase, AMP-activated, gamma 1 non-catalytic subunit | 1 | | 1 | Ser/Thr |
| LOC375449 | NM_198828 | similar to microtubule associated testis specific serine/threonine protein kinase | 2 | | 1.25 | Ser/Thr |
| PRKRIR | NM_004705 | protein-kinase, interferon-inducible double strandard RNA dependent inhibitor, repressor of (P58 repressor) | 1.25 | | 1.25 | Ser/Thr |
| DLG3 | NM_021120 | discs, large homolog 3 (neuroendocrine-dlg, Drosophila) | | 2.5 | 1 | Non-protein |
| DLG4 | NM_001365 | discs, large homolog 4 (Drosophila) | 1.25 | 1.25 | | Non-protein |
| PIK3CG | NM_002649 | phosphoinositide-3-kinase, catalytic, gamma polypeptide | | 1 | 1.5 | Non-protein |
| LIM | NM_006457 | PDZ and LIM domain 5 | | 1 | 1.5 | Not a kinase |
| PCM1 | NM_006197 | pericentriolar material 1 | 1.25 | | 1 | Not a kinase |
| PIK3AP1 | NM_152309 | phosphoinositide-3-kinase adaptor protein 1 | | 2 | | Not a kinase |
| AKAP1 | NM_003488, NM_139275 | A kinase (PRKA) anchor protein 1 | 1 | 1.25 | 1 | Kinase Binding Protein |
| CIB2 | NM_006383 | calcium and integrin binding family member 2 | | 1.25 | 1 | Regulatory, not a kinase |
| CKIIB | NM_001320 | casein kinase 2, beta polypeptide | 2.25 | 1.25 | 2 | Regulatory subunit |

A summary of the results showing the kinase siRNAs that were identified and verified in Examples 1 and 2 are shown in Tables 12 and 13. From these results, PLK2, APEG1, CDC7L1, MET, IKBKB, CKII, GRK1, 2, 6 and 7 were identified as kinases that are very likely to phosphorylate alpha-synuclein directly or indirectly. The kinases that were identified as having siRNAs that increased alpha-synuclein phosphorylation (PRKG1, MAPK13, and GAK) could very well be negative regulators of alpha-synuclein phosphorylation.

Tables 12 and 13: Summary of Confirmation Studies

TABLE 12

| Gene Name | Kinase Name | Original Screen, 100 nM Number of SD above or below SynP mean | | | Confirmation Screen, 10 nM Number of SD above or below SynP mean | | |
|---|---|---|---|---|---|---|---|
| | | siRNA A | siRNA B | siRNA C | siRNA A | siRNA B | siRNA C |
| APEG1 | Aortic preferentially expressed gene 1 | 2.25 | 1.75 | 2 | 1.5 | 1.25 | 1 |
| SNK/PLK 2 | Polo like kinase 2 | 2.25 | 1 | 1.5 | 1.5 | 1.75 | 3.25 |
| CDC7L1 | CDC7 cell division cycle 7-like 1 | 1.25 | 2 | 3 | 2.5 | 1.5 | 1.75 |
| PRKG1 | Protein kinase, cGMP-dependent, regulatory, Type I | 1.25 | | 1 | 1.5 | | 1.75 |
| MAPK13 | Mitogen-activated protein kinase 13 | 1.25 | 1 | 1.75 | 2.75 | 6.7 | 4.5 |
| GAK | Cyclin G associated kinase | 1.75 | | | 2.25 | | |
| MET | met proto-oncogene (hepatocyte growth factor receptor) | 1.5 | 1 | | 2.5 | 1.25 | |

TABLE 13

GRK Results- Mixture of Mostly, Partially and Not Confirmed

| Gene Name | Kinase Name | Original Screen, 100 nM Number of SD above or below SynP mean | | | Confirmation Screen, 10 nM Number of SD above or below SynP mean | | |
|---|---|---|---|---|---|---|---|
| | | siRNA A | siRNA B | siRNA C | siRNA A | siRNA B | siRNA C |
| RHOK | rhodopsin kinase; G protein-coupled receptor kinase 1; GRK1 | | 1 | | 1.25*** | 2.25*** | |
| ADRBK1 | adrenergic, beta, receptor kinase 1 (GRK2; BARK1) | | | 1.5 | | 1.25 | 1.75 |
| ADRBK2 | adrenergic, beta, receptor kinase 2 (GRK3; BARK2) | | 2 | | | 6.25 | 1.25 |
| GPRK2L | G protein-coupled receptor kinase 2 like; GRK4 | 1.75 | | | | | 1 |
| GPRK5 | G protein-coupled receptor kinase 5; GRK5 | | | | *** | | 1.25 |
| GPRK6/ GRK6 | G protein-coupled receptor kinase 6 | 1.25 | | 1.25 | | 1.25 | 1 |
| GPRK7 | G protein-coupled receptor kinase 7; GRK7 | | | | No siRNA | 2 | 2 |

In the following examples, in vitro kinase assays were performed on a number of the potential targets identified in Examples 1 and 2.

EXAMPLE 3

Identification of Direct Phosphorylation of Alpha-Synuclein In Vitro

To determine which of the kinase(s) from the siRNA screen directly phosphorylated alpha-synuclein, purified kinases were incubated with alpha-synuclein in in vitro kinase reactions. These results showed that PLK2, GRK2, 5, 6. and 7 (GPRK2, 5, 6 and 7) were all capable of phosphorylating alpha-synuclein specifically at serine 129 and did not phosphorylate serine 87 in vitro, showing that they could directly phosphorylate alpha-synuclein. MET, CDC7L1, and IKBKB were shown to be incapable of directly phosphorylating alpha-synuclein (FIGS. 1A-C).

Assay conditions for testing recombinant kinase activities toward recombinant alpha-synuclein at serine 129 were established and found to be reproducible by immunoblot and ELISA analyses. Commercially available recombinant kinases were used when possible. Those that were not available were produced as indicated by recombinant means.

Figure 1B:
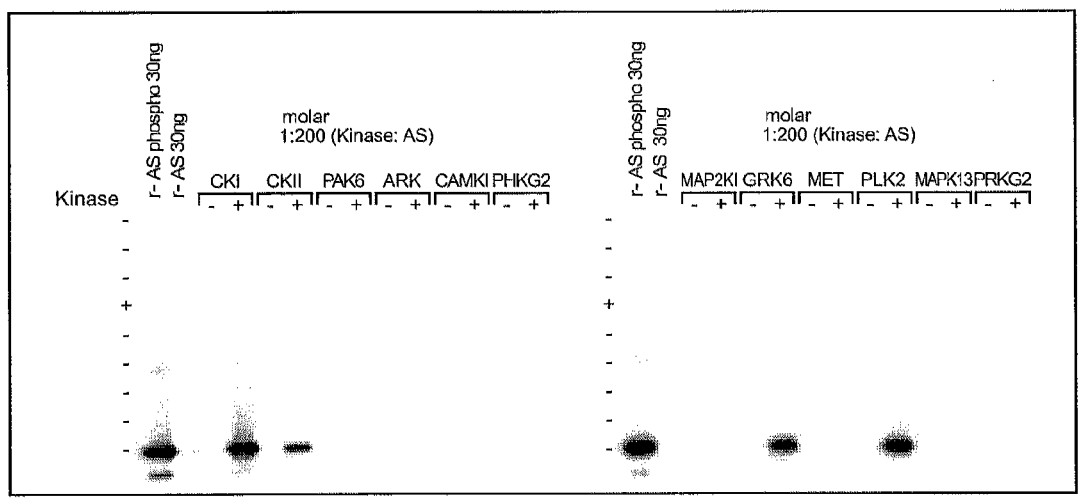
Figure 1C:
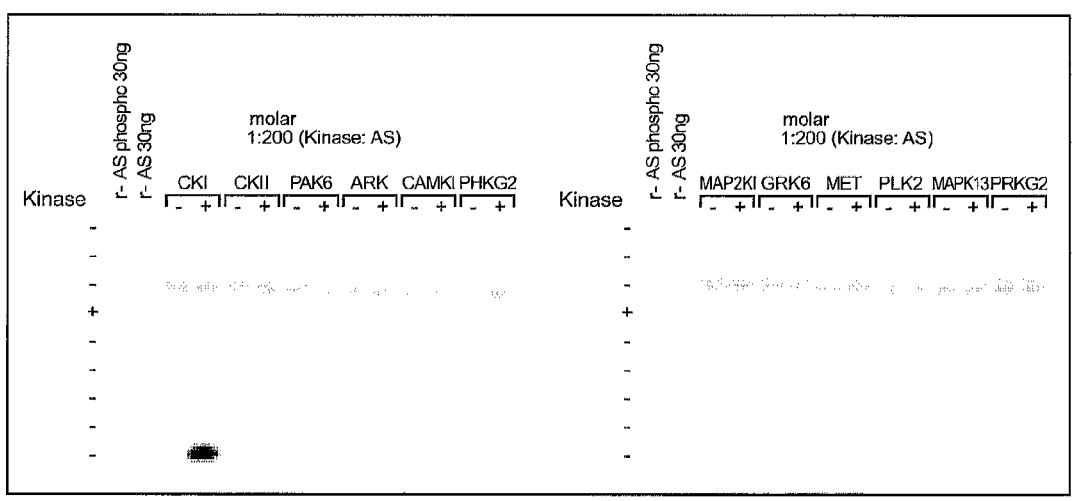

In FIGS. 1A-C, recombinant kinases were included in the in vitro alpha-synuclein (AS) assay by standardizing kinase to alpha-synuclein substrate at a constant molar ratio (derived from MW of predicted mature protein) in each reaction (1:200; kinase: recombinant alpha-synuclein kinase—rAS). −control, +kinase; In FIG. 1A, a probe for total alpha-synuclein (AS) (mAb Syn-1; 0.1 µg/mL) was used indicating equivalent substrate in each reaction; In FIG. 1B, a parallel blot was probed for S129 phosphorylation (mAb 11A5 1 µg/mL). Prominent signals came from GRK6, CKI, CKII and PLK2 (not previously tested by activity normalization). In FIG. 1C, a parallel blot probed for S87 phosphorylation (pAb, ELADW-110 5 µg/mL). A signal was detected only with CKI phosphorylation.

Figure 1D:
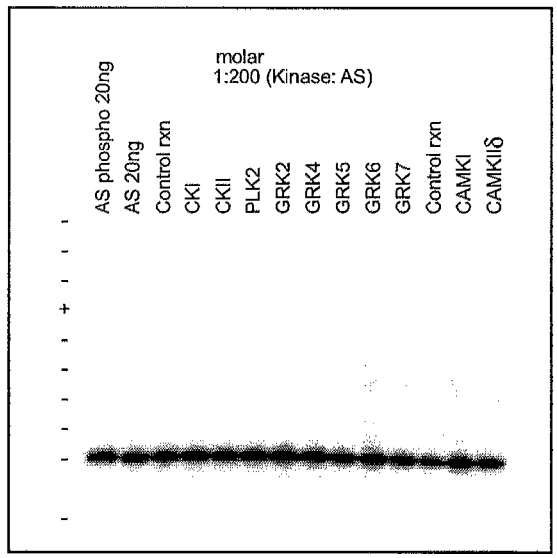
FIGS. 1D-F show a study with recombinant kinases, including kinases from the GPCR-receptor kinase (GRK) family and PLK2.
Figure 1E:
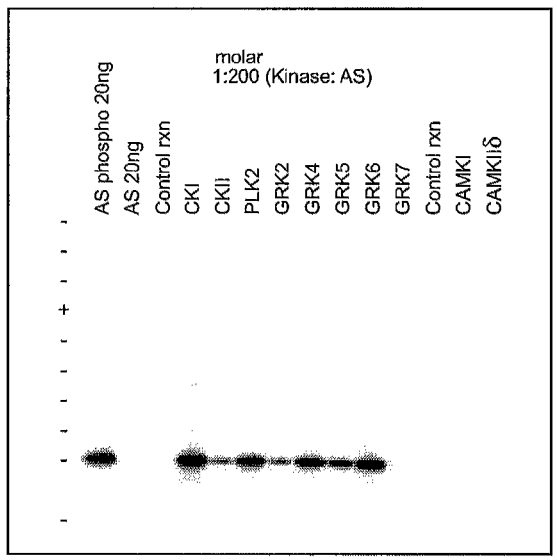
Figure 1F:
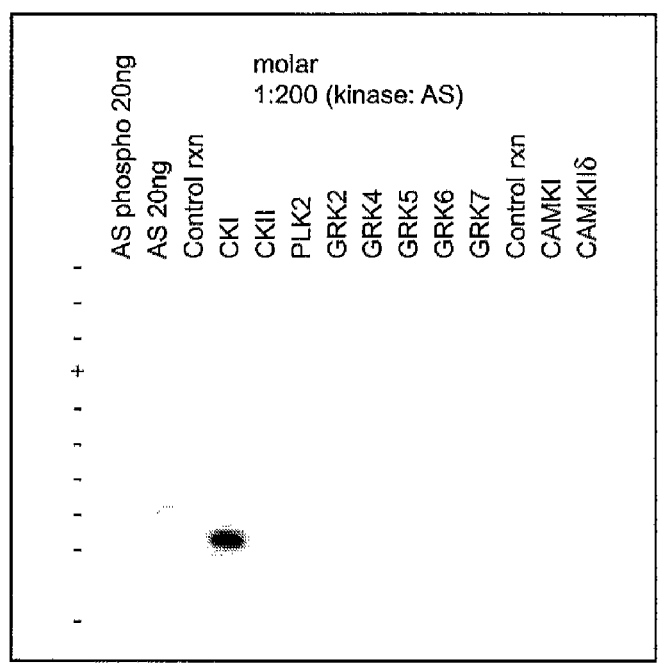

In FIGS. 1D-F, a more focused study was performed with recombinant kinases from the GPCR-receptor kinase (GRK) family and PLK2 were included in the in vitro alpha-synuclein (AS) assay by standardizing kinase to AS substrate at a constant molar ratio (derived from MW of predicted mature protein) in each reaction (1:200; kinase: rAS). −control, +kinase; CAM kinases served as negative controls while CKI and II served as positive controls. In FIG. 1D, a probe for total AS (mAb Syn-1; 0.1 µg/mL) was used indicating equivalent substrate in each reaction; In FIG. 1E, a parallel blot probed for S129 phosphorylation (mAb 11 A5 1 µg/mL). Prominent signals came from all GRKs except for GRK7. A specificity between GRK members could be seen with signal and can be represented as: CKI>GRK6>PLK2>GRK4>GRK5>GRK2. In FIG. 1F, a parallel blot probed for S87 phosphorylation (pAb, ELADW-110 5 µg/mL). Signal was detected only with CKI phosphorylation.

The assay conditions are defined in Table 14 and were held constant for all kinases tested. All of the kinases listed were available as tagged/recombinant protein with the exception of CDC7L1, PRKG1 and APEG. Those putative targets were expressed in an in vitro translation system and tested in the in vitro AS assay without protein concentration or activity measurements.

TABLE 14

Assay conditions for in vitro kinase reactions:

| # | Kin | Confirmation | MW kinase | 1:200 kinase:AS (molarity) ng kinase; ul in 100ul rxn | total ul kin. in stock | ng/ul kin | Units/ul | Dilution | Total ul kin./rxn | ng kin/rxn | co-factors |
|---|---|---|---|---|---|---|---|---|---|---|---|
| 1 | CKI a' | most | 49000 delta | 5.1 ng; 6.3 ul (1000x dilution) | 20 | 814 | 1000 | 100000x (0.01 U/ul) | 3 | 0.024 | |
| 2 | CKII a' | part | 44,000 alpha 26,000 beta | 4.6 ng; 4.3 ul (1000x dilution) | 20 | 1070 | 500 | 50000x (0.01 U/ul) | 3 | 0.0642 | |
| 3 | PAK6 | part | 38,000 | 4 ng; 1 ul (100x dilution) | 50 | 100 | 0.21 | 10x (0.021 U/ul) | 1.43 | 14.3 | |
| 4 | ARK5 | most | 78,000 | 8.1 ng; 8.1 ul (100x dilution) | 50 | 100 | 0.06 | | 0.5 | 50 | |
| 5 | CaMK1 | most | 68,000 | 7.1 ng; 7.1 ul (100x dilution) | 50 | 100 | 0.29 | 10x (0.029 U/ul) | 1 | 10 | calmodulin 1uM |
| 6 | PHKG2 | del | 52,000 | 5.4 ng; 7.7 ul (100x dilution) | 143 | 70 | 0.007 | | 4.3 | 301 | |
| 7 | MAP2K1 | del | 49,000 | 5.1 ng; 5.1 ul (100x dilution) | 20 | 500 | 1.69 | 100x (0.00169 U/ul) | 17.75 | 90 | |
| 8 | GRK6 | part | 94,000 | 9.8 ng; 3 ul (100x dilution) | 34 | 290 | 0.008 | | 3.75 | 1088 | |
| 9 | CAMKII delta | del | 59,000 | 6.2 ng; 1.9 ul (100x dilution) | 31 | 320 | 4.93 | 100x (0.0493 U/ul) | 0.61 | 195 | calmodulin 1uM |
| 10 | Met | conf | 50,000 | 5.2 ng; 5.2 ul (100x dilution) | 50 | 100 | 0.022 | | 1.363 | 136 | |
| 11 | MAPK13 | conf | 46,000 | 4.8 ng; 1.1ul (100x dilution) | 22 | 450 | 0.054 | | 0.56 | 250 | |
| 12 | PRKG2 | most | 117,000 | 12.2 ng; 2.8 ul (100x dilution) | 22 | 440 | 0.017 | | 1.76 | 776 | |
| 13 | PLK2 | conf | 106,000 | 11 ng; 4.1 ul (100x dilution) | 27 | 270 | 0.027 | | 1.1 | 297 | |
| 14 | GRK2 | most | 82,300 | 8.6 ng; 1.7 ul (100x dilution) | 20 | 500 | 0.0045 | | 6.7 | 3350 | |
| 15 | GRK4 | part | 94,000 | 9.8 ng; 2.5 ul (100x dilution) | 25 | 400 | 0.0012 | | 25 | 10,000 | |

TABLE 14-continued

Assay conditions for in vitro kinase reactions:

| # | Kin | Confirmation | MW kinase | 1:200 kinase:AS (molarity) ng kinase; ul in 100ul rxn | total ul kin. in stock | ng/ul kin | Units/ul | Dilution | Total ul kin./rxn | ng kin/rxn | co-factors |
|---|---|---|---|---|---|---|---|---|---|---|---|
| 16 | GRK5 | part | 95,200 | 9.9 ng; 2.1 ul (100x dilution) | 21 | 480 | 0.00018 | 167 | | 80,160 | |
| 17 | GRK7 | part | 89,700 | 9.3 ul; 1.9 ul (100x dilution) | 21 | 480 | 0.00067 | | 45 | 21,600 | |
| 18 | CDC7L1 | conf | 63,800 | undetermined; in vitro translation | nd | nd | nd | | nd | nd | |
| 19 | PRKG1 | conf | 76,200 | undetermined; in vitro translation | nd | nd | nd | | nd | nd | |
| 20 | PDK1 | part | 59,000 | 6.1 ng; 3 ul (200x dilution) | 50 | 200 | 0.074 | 10x (0.0074 U/ul) | 4.05 | 81 | SGK |
| 24 | APEG | conf | 12,600 | undetermined; in vitro translation | nd | nd | nd | | nd | nd | |

The Standard Conditions were: 40 mM MOPS-NaOH; 1 mM EDTA MgCl 10 mM pH 8.0, 0.1% BME; 0.01% Brij-35; 5 ug BSA, 100 uM ATP (5×[substrate]), 100 uL volume; 300 ng r-wt-AS (208 nM), (1:200 kinase: AS or activity normalized 0.03 U/rxn, 34 C; 17 hrs. Further, those kinases with varying levels of significance/confirmation from combined screening data were purchased as recombinant, tagged protein, annotated and incorporated into a table format for the purposes of establishing in vitro assays that were comparable based upon normalization to activity units (determined by the manufacturer from synthetic substrates) or substrate:enzyme molar ratios determined from MW and reaction volume. The details of reaction conditions are stipulated in Table 14. Kin.=kinase. For Confirmation: Most=mostly, Part=partially, del=deleted, conf=confirmed.

Figure 2A:
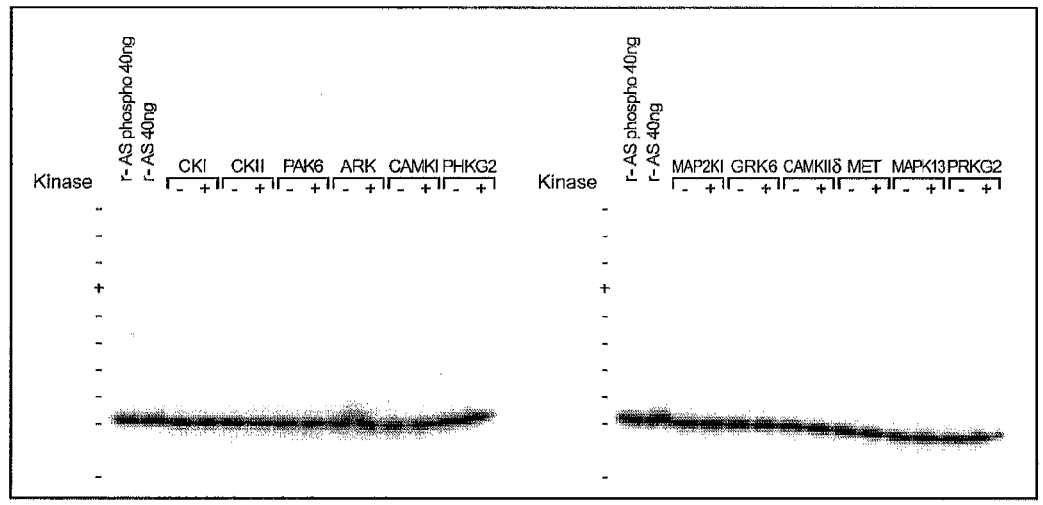
FIGS. 2A and B show the results of kinase activity in vitro for various kinases.
Figure 2B:
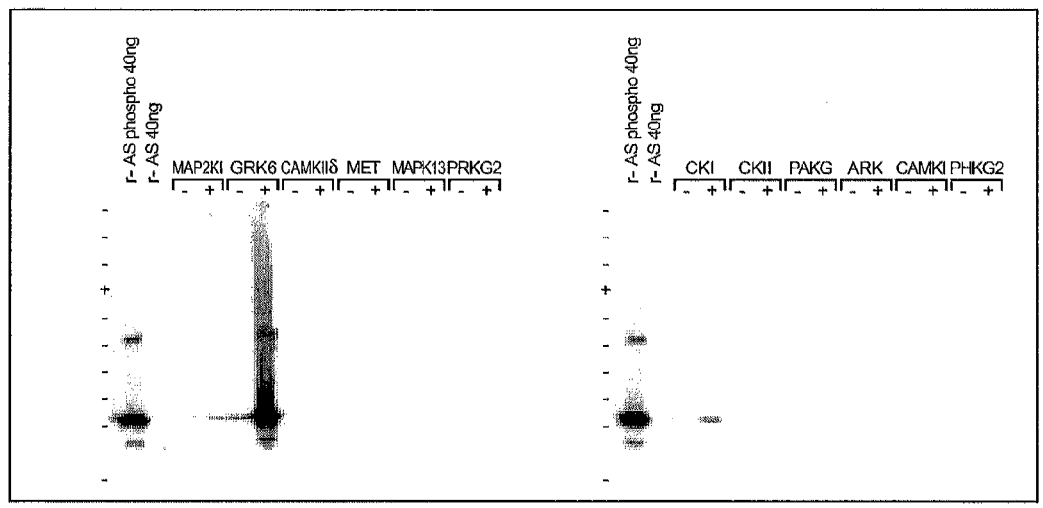
FIG. 2B shows phosphor-serine 129.

Kinase activity was initially tested against AS by activity units as determined from non-native substrates (peptides or casein). This method was used to get a rough estimate as to specificity between kinases and whether AS was an in vitro substrate for the kinase panel. The results of this study are found in FIGS. 2 and 3. At the time of this experiment, only a portion of available kinases were obtained and ⅔ kinases from the "most probable 7 confirmed" were included (PLK2 was not tested). The most prominent result came from GRK6 (G-protein coupled receptor kinase 6). CKI gave a modest signal and CKII was not detectable. Because both CK kinases are known to phosphorylate S129 AS, normalization by activity units was biased against those kinases which had higher specific activity for tested substrates vs AS. This was likely the situation for GRK6 which might have preferred AS as a substrate rather than the peptide substrate which defined its activity units.

Figure 3A:
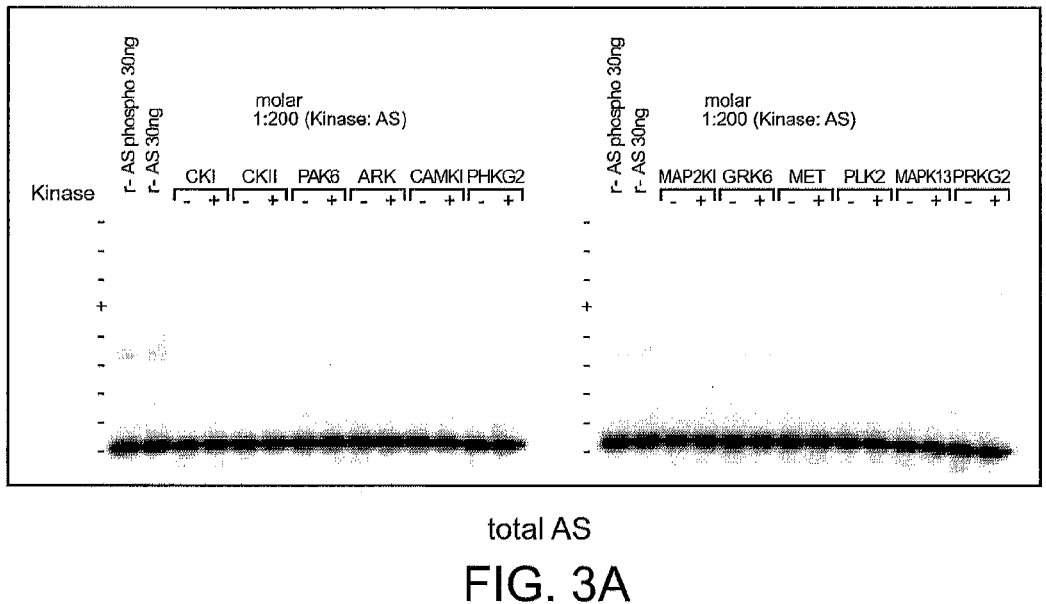
FIGS. 3A-C show the results of kinase activity in vitro for various kinases.
Figure 3B:
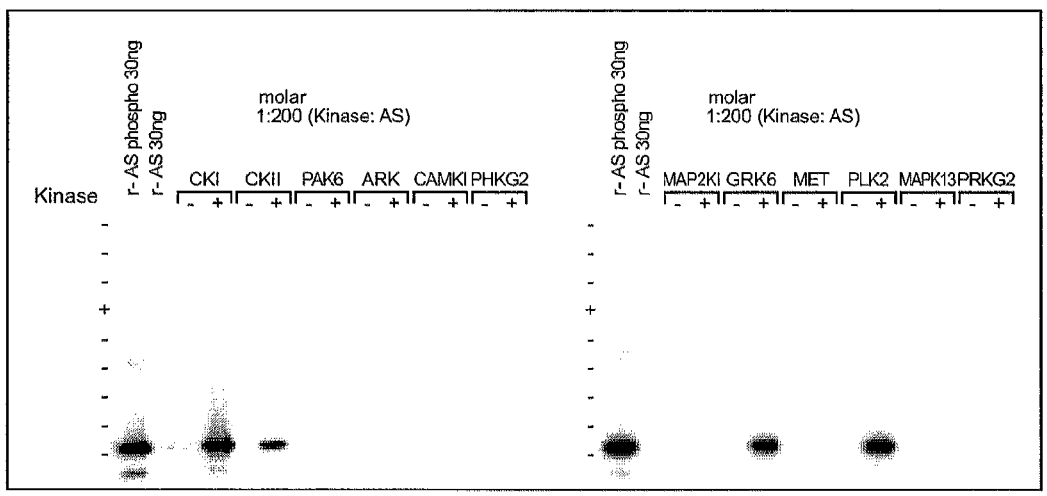
Figure 3C:
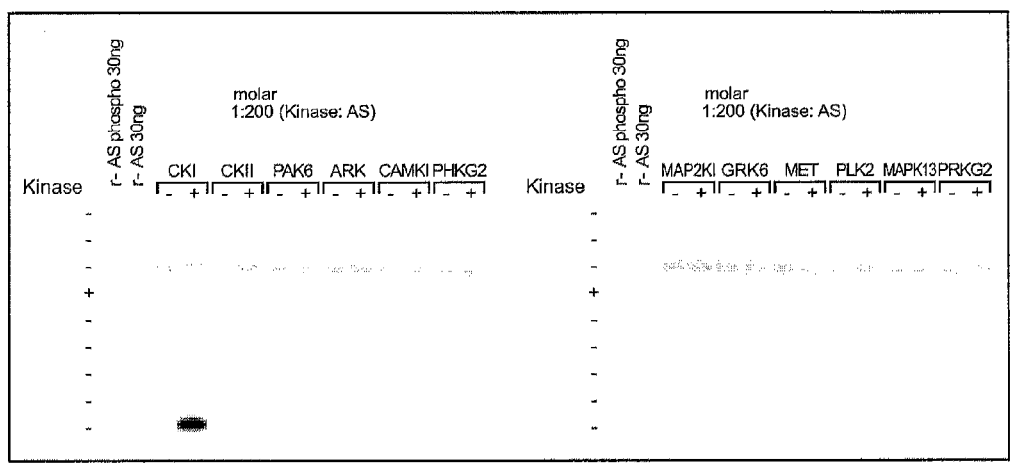

In the following examples, in vitro kinase assays were performed on a number of the potential targets identified in Examples 1 and 2. To correct for the activity bias, kinases were retested and newly procured kinases were put into an assay that normalized for molarity. This gave a better measurement of stoichiometric ratios between enzyme and substrate, thus reporting the phosphorylation event as a function of AS/kinase interaction. This was in contrast to the event in which unrelated substrate/kinase phosphorylation was measured. FIGS. 3A-C illustrate a more realistic view of AS phosphorylation with roughly equivalent levels of phospho ser-129 between CKI, GRK6 and PLK2 (one of 7 highly confirmed). With the exception of CKI, none of the tested kinases were capable of phosphorylating AS at the ser-87 residue. This observation confirmed the specificity/preference of these kinases for the ser-129 site and/or the low preference/inaccessibility for the ser-87 site. However, CKI has been reported to phosphorylate at both sites.

Effect of Acidic Phospholipid on the Assay Results

Figure 4A:
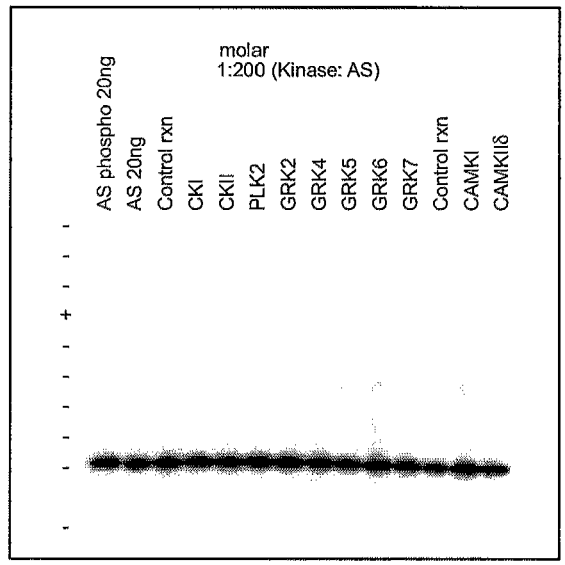
FIGS. 4A and B show the effect of phospholipid on the assay results in FIGS. 3A and 3B.
Figure 4B:
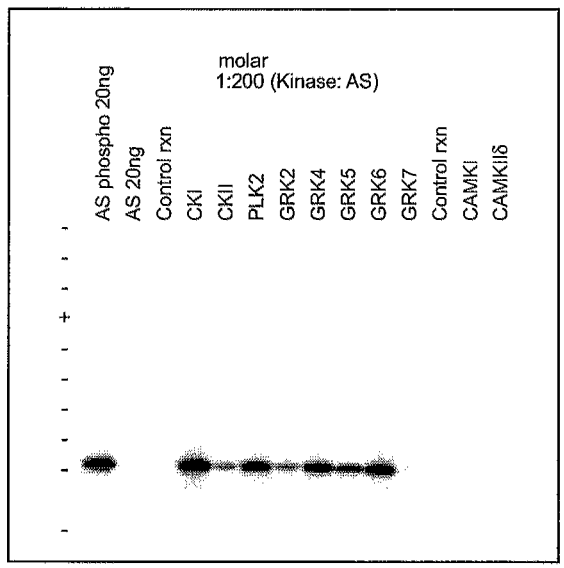
FIG. 4B shows Serine 129.
Figure 5:
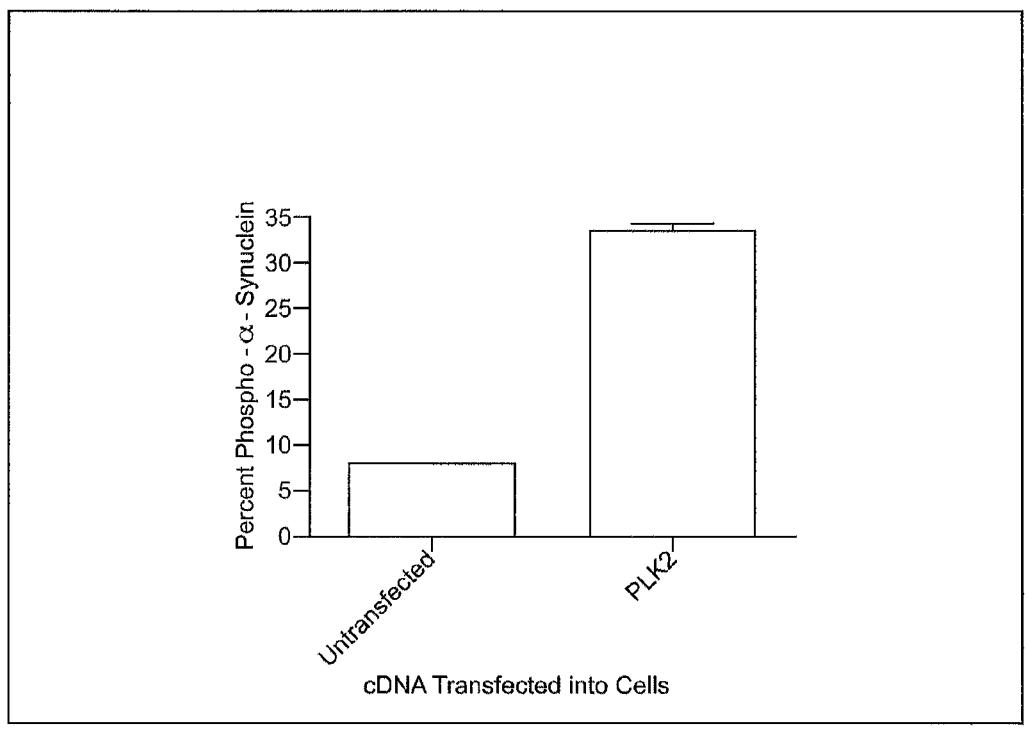
FIG. 5 shows the results of transfection of cDNA to PLK2 into 293-synuclein cells. Cells were analyzed by ELISA for total and phospho-synuclein levels.

The significant levels of activity by GRK6 and PLK2 (polo-like kinase phylogenetically related to the GRK family) in the in vitro assay combined with the identification of PLK2, GRK2 and GRK1 as decreasers of phosphorylation in the RNAi screen, prompted a more comprehensive survey of other GRK members. FIGS. 4A and B indicate the results of GRK 2, 4, 5, 6, 7 and PLK2 compared in the in vitro assay. This preference could be represented as CKI>GRK6>PLK2>GRK4>GRK5>GRK2. GRK 7 was not able to phosphorylate at appreciable levels. All GRKs were unable to phosphorylate at ser-87 pointing to a specificity for the acidic sequence flanking amino acid 129. These reactions were quantitated and confirmed by ELISA measurements. These values more or less agreed with the immunoblot data with an apparent decrease in PLK2 level vs GRKs. It is likely that most of the AS substrate was depleted (phosphorylated) based on the assay design (300 ng AS, 210 nM for 17 hr).

The positive effect of acidic phospholipids on the phosphorylation of AS has been previously reported Pronin et. al. JBC 275(34): 26515-26522 (2000) and a pronounced effect on GRK 2 and 5 was observed. Because of this report and the many studies indicating that acidic phospholipids modulate AS conformation, a mixture of phosphatidylcholine (PC): phosphatidylserine (PS): phosphatidyl-inositol-phosphate-3 (PIP3) was generated and incorporated into the established in vitro assay. The lipid mixture was shown to increase signal for almost all of the kinases tested. The addition of a lipid environment is likely to imitate the membrane surface in a cell where AS and GRKs are likely to associate. Without being bound by the following theory, it is probably due to a favorable exposure of the C-term of AS upon lipid binding of the N-term helices of AS. Interestingly, the lipid effect of ser-87 phosphorylation (as see by the CKI reaction) led to a decrease in the level of phosphorylation. This may be the result of epitope masking by lipid interaction if ser-87 is buried upon helix interaction.

EXAMPLE 4

Identification of Direct Phosphorylation of Alpha-Synuclein in Cell Lines

Figure 6:
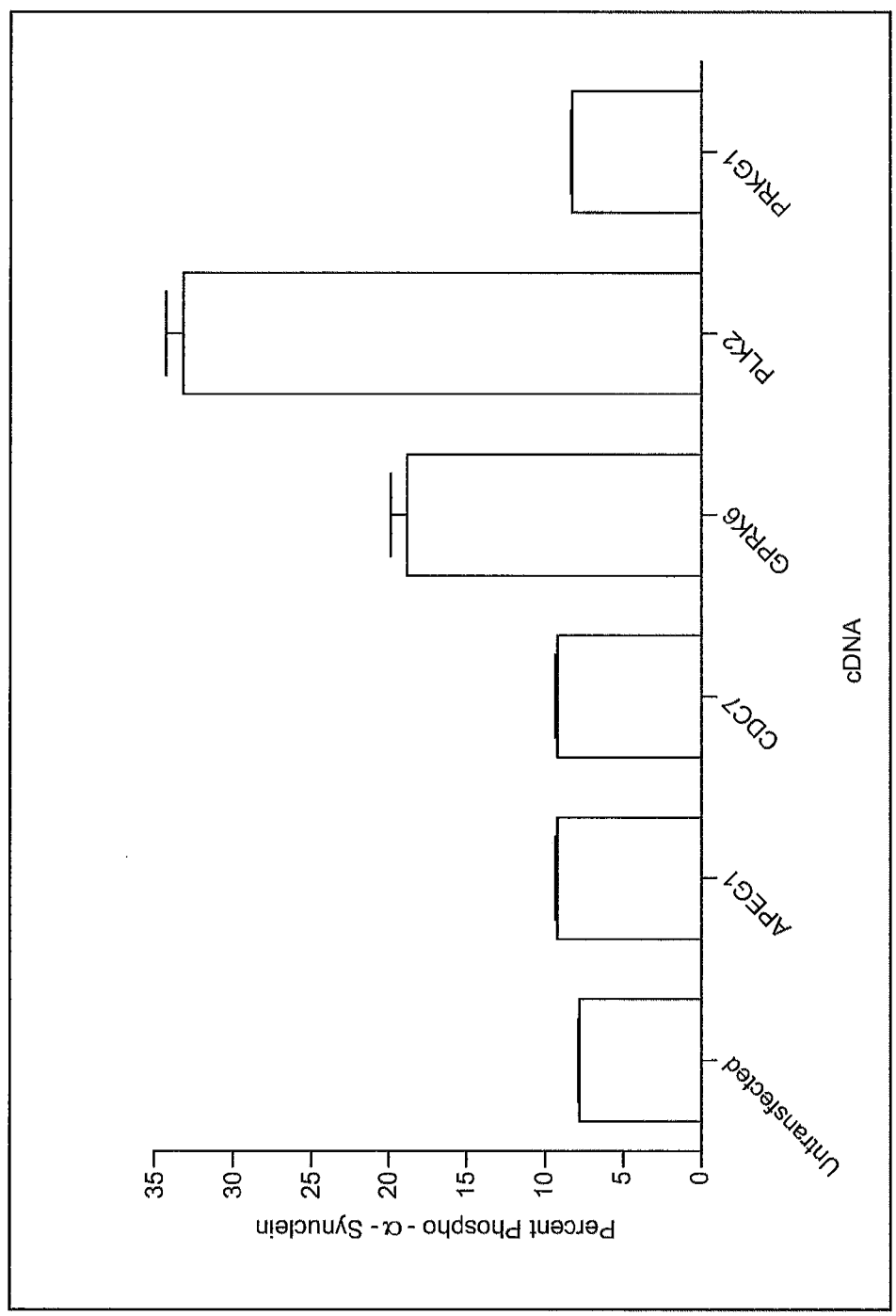
FIG. 6 shows the results of transfection of cDNA to GPRK6 and PLK2 into HEK-Synuclein cells.

Because kinases can be more promiscuous in vitro than they are in cells, an assay was performed in cell lines to confirm the direct interaction with alpha-synuclein. cDNAs for the kinases that phosphorylated alpha-synuclein in vitro from Example 3 were transfected into the PEAK-Syn cell line to see which was capable of phosphorylating alpha-synuclein ser-129 in cells. The results showed that GRK6 and, to an even greater extent, PLK2 were able to mediate alpha-synuclein phosphorylation in cells (FIG. 6).

cDNA clones for PLK2, GPRK6, APEG1, CDC7 and PRKG1 were obtained from Origene. The cDNA was transcribed and transfected into PEAK-Syn cells using Lipofectamine 2000™ (Invitrogen). For each cDNA analyzed, 12 wells of a 96-well plate were transfected, along with 12 control wells of untransfected cells. Cells were harvested at 48 hrs post-transfection as per the ELISA screening protocol, and analyzed by ELISA for total and phospho-synuclein, and values were normalized for total protein. For those kinase targets not commercially available as recombinant proteins (namely APEG, PRKGI and CDC7LI), an in vitro cell-free reticulocyte system (Promega) was employed to express protein from human full-length cDNA clones (Origene). Proper sequence was determined and DNA prepared. PLK2 and GRK6 cDNA was also included in the study as positive controls.

The percentage of phospho-synuclein in untransfected cells was calculated to be 7.8%. The percentage of phospho-synuclein for the cells transfected with APEG1, CDC7 and PRKG1 cDNA was only marginally higher than untransfected cells at 8.9%. These kinases were considered to have produced a negative result in altering phospho-synuclein levels, and were considered negative controls for experimental purposes, as they were subjected to the same rigors of transfection that the other kinases were exposed to cDNA to PLK2 was transfected into 293-synuclein cells. Cells were harvested 48 hrs following transfection and analyzed by ELISA for total and phospho-synuclein levels. ELISA values were corrected for total protein levels. Overexpression of PLK2 resulted in a dramatic increase in phospho-synuclein levels, increasing phospho-synuclein expression by 4.3-fold above expression in untransfected cells.

It is likely that when a direct kinase that phosphorylates α-synuclein is introduced into the cell an increase in phospho-synuclein levels would be observed. This was the case for both GPRK6 and PLK2 (FIG. 6). The percent phospho-synuclein in cells transfected with GPRK6 cDNA increased dramatically, from 8.9% to 18.9%. This increase is significant to 9.25 standard deviations above the percent phospho-synuclein observed for the negative kinases. The increase in phospho-synuclein levels for the PLK2-transfected cells was even more dramatic, increasing the percent phospho-synuclein almost four-fold to 33.2%. This represents an extremely significant change, an increase of 22.75 standard deviations above the phospho-synuclein levels observed for the negative kinases. This dramatic increase was by far the largest change observed previously in using this assay. This data strongly indicates GPRK6, and especially PLK2 as very solid contenders as direct kinases responsible for phosphorylating α-synuclein. Thus, as shown in FIG. 6, when GPRK6 cDNA is transfected into HEK-synuclein cells, the expression of phospho-synuclein increases 2-fold. Introduction of PLK2 cDNA into cells results in an even more dramatic increase in phospho-synuclein expression, a change of almost four-fold above control values.

EXAMPLE 5

Phosphorylation by PLK2 (SNK) GRK6, CKII and IKBKB

The data in Example 4 was further substantiated for PLK2 by showing that PLK2 siRNAs reduced alpha-synuclein phosphorylation. This strengthened the data showing that PLK2 is a likely candidate as a cellular kinase that directly phosphorylates alpha-synuclein at Serine 129 (Tables 2 and 12).

Figure 7:
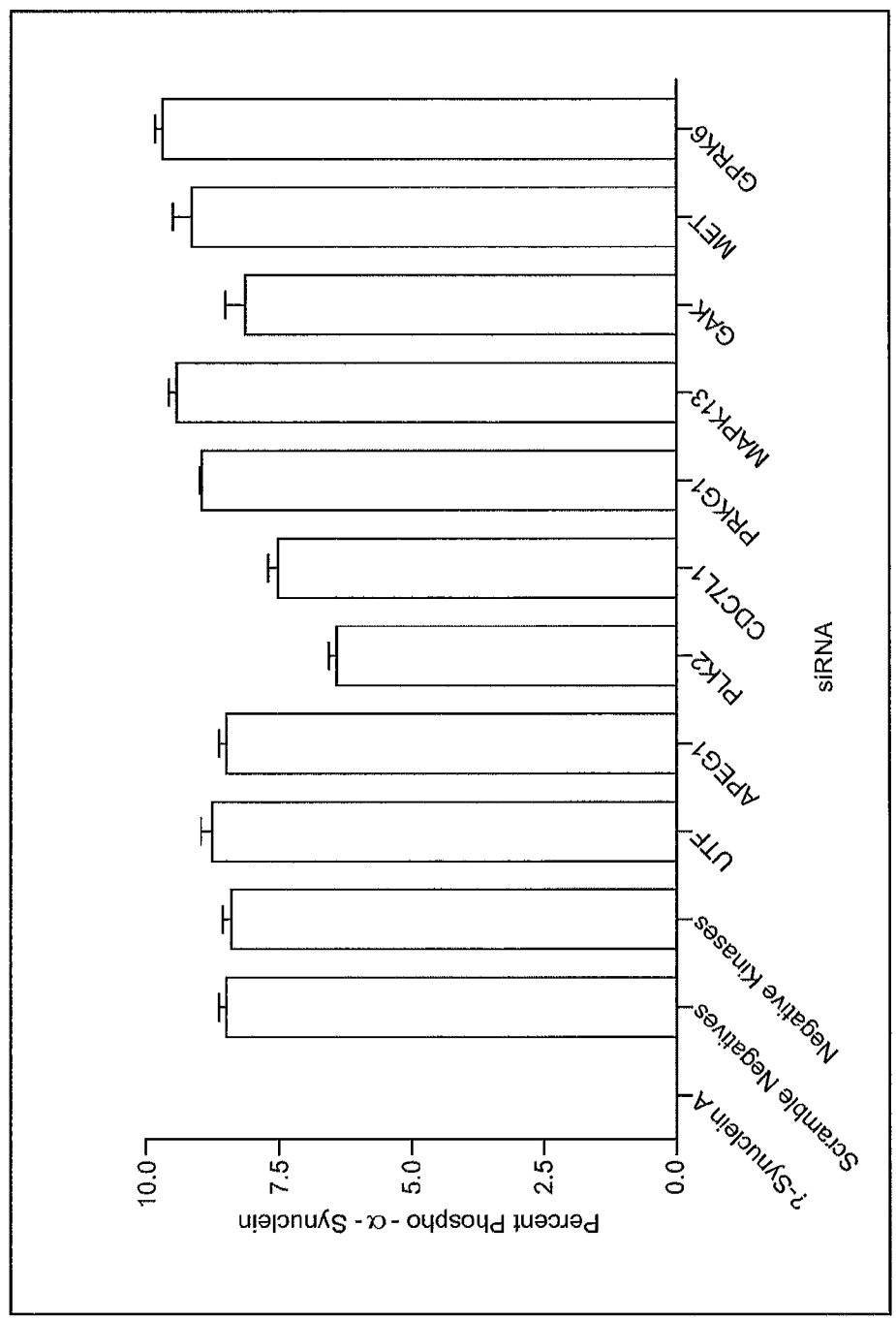
FIG. 7 shows that knockdown of the PLK2 using siRNA from a second source causes a reduction in the proportion of alpha-synuclein that is phosphorylated.

HEK 293 cells stably transfected with alpha-synuclein were transfected with 10 nM and 100 nM of SmartPool siRNAs (Dharmacon). SmartPool siRNAs include 4 individual siRNAs to a specific target. Thus, the actual concentration of each of the four siRNAs transfected into cells was 2.5 nM and 25 nM respectively. The results in FIG. 7 show that PLK2 significantly decreased phospho-synuclein levels, a change of approximately 25%. At 10 nM, but not at 100 nM of siRNA, GPRK6 significantly increased the percentage of phospho-synuclein by one standard deviation above the mean of the control negative kinases (FIG. 7). This is the opposite effect to what was previously observed in the primary siRNA screen and may be due to the quality of the siRNA used in the first or second assays. These results were confirmed by immunohistochemistry.

The significant knockdown of phospho-synuclein levels by different siRNAs from a different source, independently confirms and solidifies the data, and substantiates the role of PLK2 as a direct kinase that phosphorylates α-synuclein. These experiments were then performed on two other kinases identified in the screens to be of interest, casein kinase two (CKII) and IKBKB.

The individual CKII catalytic subunits were hits in the primary siRNA screen (see Example 1 and Table 1B) and confirmed at the 10 mM siRNA screen. It was of interest to determine if the individual CKII subunits $\alpha^1$ and $\alpha'$, when cotransfected with PLK2 or each other, had additive effects on alpha-synuclein phosphorylation. Transfections were performed using the individual CKII subunits A ($\alpha^1$) and B ($\alpha'$), cotransfected with PLK2 or each other. Overexpression of these catalytic subunits increased phospho-synuclein levels by 1.75 and 1 standard deviations respectively (the effect was not additive). When each of the individual subunits was co-transfected with PLK2, the levels of phospho-synuclein increased over that of PLK2 alone (18.6% phospho-synuclein) by 1.25 standard deviations each to 22.8% phospho-synuclein. However when both subunits were co-transfected with PLK2 phospho-synuclein levels were not significantly increased above that for PLK2 alone (21.4% phospho-synuclein).

IKBKB siRNA knockdown resulted in a significant decrease in alpha-synuclein phosphorylation so this gene was tested for capacity to phosphorylate alpha synuclein. Transfections and ELISA analysis were performed as per standard procedure. Previous in vitro experiments demonstrated that IKBKB was not a direct synuclein kinase as it did not phosphorylate synuclein in a direct kinase assay (see Example 3), but may be an upstream regulator of synuclein phosphorylation. Thus, IKBKB was over-expressed in HEK-syn cells to identify the effect on phosphorylation of synuclein. Following introduction of IKBKB cDNA into cells, synuclein phosphorylation increased from 8.3% in the negative (empty vector) control to 21.5%, a 2.6-fold increase. This represented an increase in synuclein phosphorylation that was significant to almost 53 standard deviations. The PLK2 positive control increased synuclein phosphorylation to 65.8%, an almost 8-fold increase in phosphorylation (significant to 230 standard deviations). Although the effect on synuclein phosphorylation was much more modest for IKBKA, a related kinase, (1.2 fold) than for IKBKB, it was still significant to 1.4 standard deviations.

EXAMPLE 6

Synphilin as an Alternative Therapeutic Target

Synphilin is a synuclein-associated protein that has been shown to bind alpha-synuclein. To determine if the presence of synphilin can enhance the phosphorylation of alpha-synuclein, it was over-expressed in HEK cells with and without alpha-synuclein and PLK2. Transfections were performed according to standard protocol, followed by alpha-synuclein ELISA and analysis. Cells were also harvested for Western blot analysis. Transfected cell lysates were analyzed for total synuclein using 1H7 antibody and phospho-serine 129 synuclein using 11A5 antibody (See WO 05047860). The total amount of DNA transfected into cells remained constant at 0.16 µg/well of a 96-well plate. The type of DNA introduced into cells varied, with empty vector being used to make up the full quota of DNA. Varying concentrations of alpha-synuclein, PLK2, and synphilin cDNA were introduced into naïve HEK cells. Cells transfected with all three showed a slight increase in total synuclein. For phospho-synuclein, the levels in untransfected cells were below the limit of quantitation. Introducing alpha-synuclein alone yielded 5.2% phospho-synuclein, which was marginally less than co-transfection of synuclein with synphilin (5.4% phospho-synuclein). Co-transfection of PLK2 and synuclein yielded levels similar those observed for transfecting PLK2 into HEK-syn stable cells, 60% phospho-synuclein. Strikingly, concurrent over-expression of all three cDNA's (PLK2, synuclein and synphilin) resulted in 83.3% phospho-synuclein in the HEK cells. Thus, synphilin increased synuclein phosphorylation in PLK2, alpha-synuclein over-expressed HEK cells.

Increased phosphorylation of alpha synuclein in the presence of synphilin can be explained by synphilin binding to the PLK2 polo-box thereby facilitating phosphorylation of synuclein by PLK2. Synuclein itself is unlikely to bind the polo-box domain.

EXAMPLE 7

PLK2 Activity: Phosphorylation of Alpha Synuclein and Familial Mutants of Alpha Synuclein To analyze PLK2 phosphorylation of a number of known familial mutants of alpha synuclein, in vitro studies were performed and the phosphorylation of the alpha synuclein and mutants analyzed. The familial mutants (FPD) were A30P, A53T, and E46K.

All in vitro reactions were performed using the following conditions, 10 mM MgCl2, 100 µM ATP, 27 mM HEPES, 250 ng/ml PLK2, 1/50 dilution of Protease Inhibitor solution (1 tablet in 1 ml of reaction buffer), 40 mM Nitrophenylphosphate, 1 mg/ml of 95% Type II-S Phosphatidylcholine from soybean, and 10, 100, or 1000 nM alpha synuclein (AS). The reaction was incubated at 37° C. The activity was analyzed by autoradiography.

PLK2 was found to be more active against wild-type alpha synuclein than beta synuclein. Further, the mutant alpha-synucleins were phosphorylated more at a given concentration (especially at lower concentrations) than WT. A trend of PLK2 activity was identified with PLK2 activity being highest with FPD mutants, followed by wild-type alpha synuclein, and minimally against beta synuclein. This order is consistent with a mechanism by which phosphorylation of alpha synuclein drives Lewy body formation and subsequent pathology.

EXAMPLE 8

Figure 9A:
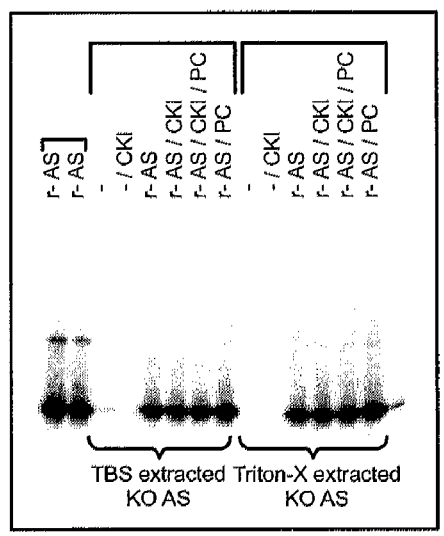
FIGS. 9A and 9B show the in vitro phosphorylation of alpha-synuclein by putative kinase targets in alpha-synuclein KO mouse brain.
Figure 9B:
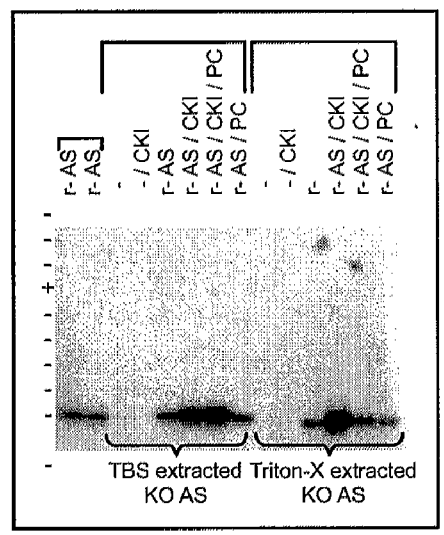

Confirmation of the Presence of Kinases in HEK-Synuclein and SY5Y-Synuclein Cells qRT-PCR was performed to determine if the kinases of interest were expressed in HEK-synuclein and SY5Y-synuclein cells. In Table 15 all samples were normalized to GAPDH expression. In addition, two of the negative kinases were analyzed in each experiment as a reference. Of the 24 potential direct kinase candidates tested, 20 were detected in the HEK293-synuclein cells, including PLK2. Thus, the remaining completely confirmed kinases were detected in the cells (FIG. 9). Four of the potential direct kinases tested, GPRK1, GPRK7, ERK8 and RIPK3, were not detected. GPRK6 was barely detectable.

The qRT-PCR was performed as follows: the mRNA levels were normalized to GAPDH mRNA expression levels. Total RNA was purified from a cell pellet using the QIAGEN RNeasy Kit and protocol. Primer-probe sets for 24 of the potential direct kinases and the four indirect completely confirmed kinases were ordered from Applied Biosystems (Taq-Man Gene Expression Assays), along with reverse transcriptase, RNase inhibitors and standard PCR reagents. A one-step RT-PCR/qRT-PCR reaction as performed an ABI7500 Real-Time PCR machine for each primer-probe set using 20 ng or 200 ng total RNA using the following cycling conditions: 48° C./30 mins (RT-PCR step), 95° C./10 mins (denature), then 40 cycles of 95° C./15 secs, 60° C./1 min. For each primer-probe set, an RT-negative reaction and PCR-negative reaction was performed. The RT-negative controls for background amplification of DNA (not RNA) that is contaminating the purified RNA. The PCR-negative control was to ensure all of the PCR reagents were free of contaminating RNA and DNA, and should have had no signal.

All three of the completely confirmed potential direct kinases, along with the four indirect completely confirmed kinases were easily detected in SY5Y-synuclein cells, indicating this cell line may be a viable option for a neuronally-derived cell line for further experimental analysis of kinases.

TABLE 15 qRT-PCR demonstration of the presence of kinases in HEK-synuclein and SY5Y-synuclein cells

| Sample Name | Relative Expression (to GAPDH) |
|---|---|
| SYN APEG1 | 2.23 |
| SYN SNK/PLK2 | 3.57 |
| SYN CDC7L1 | 1758.34 |
| SYN PRKG1 | 7.36 |
| SYN MAPK13 | 8.97 |
| SYN GAK | 2.17 |
| SYN MET | 891.44 |
| SY5Y-SYN APEG1 | 1698.45 |
| SY5Y-SYN SNK/PLK2 | 208.66 |
| SY5Y-SYN CDC7L1 | 24.42 |
| SY5Y-SYN PRKG1 | 42.22 |

TABLE 15-continued qRT-PCR demonstration of the presence of kinases
in HEK-synuclein and SY5Y-synuclein cells

| Sample Name | Relative Expression (to GAPDH) |
|---|---|
| SY5Y-SYN MAPK13 | 45.73 |
| SY5Y-SYN GAK | 17.63 |
| SY5Y-SYN MET | 86.22 |

EXAMPLE 9

Identification of Increased Phosphorylation of
Alpha-Synuclein in 293 Cells and
Neuronally-Derived Cell Lines PLK2 and GRK were overexpressed in 293 cells stably transfected with alpha synuclein. ELISA and Western blot were performed to identify increase in phospho-synuclein with PLK and GRK kinases and an increase in phosphorylation was demonstrated. A second method was used to confirm the increase using the same biotinylated antibodies used in the ELISA for immunostaining (11A5) in 293 cells. This method also demonstrated an increase in phospho-synuclein in cells transfected with PLK2 and to a lesser extent GRK. The increase was detected in a small population of cells that brightly stain for 11A5, not a general increase in all cells. The amount of total synuclein (measured using the 5C12 antibody) did not appear to change. This was a significant increase in phosphorylation in the 293 cells. Thus, it was of interest to see if the results could be repeated in neuroblastoma cells.

To identify that the dramatic upregulation of phospho-synuclein observed with PLK2 and GPRK6 occurs in neuronally-derived cells, the same experiment was performed in human neuroblastoma cells (SY5Y cells). Immunostaining results showed that PLK2 caused an increase in the phospho-synuclein in a small population of cells, in a very similar pattern to the 293 cell experiments. Quantitation was performed by immunohistochemistry using the ArrayScan™ in two ways. First all cells were counted and did not show any difference. Then just the bright cells were counted and this analysis showed about a 5-10 fold increase in the number of 11A5 positive cells that were PLK transfected, with a slight increase with GRK6 as well.

The cDNA transfection experiment is repeated in HCC cells and immunohistochemistry is performed with a variety of alpha-synuclein antibodies on the cells that have been transfected with PLK2 and GPRK6. Cells may be treated with additional reagents to mimic the pathology of Parkinson's disease; such reagents could include, for example, rotenone, paraquat, hydrogen peroxide, or ferric chloride. In this way, inclusion formation and/or alpha-synuclein aggregation is observed in these cells. Antibodies used to look for inclusions/aggregation include LB509, SYN-1, 11A5 and ELADW-110.

Next, cDNA for PLK2 and GPRK6 siRNA is transfected in primary neuronal cultures in preparation for introducing targets into a mouse model. The method is performed as in Example 4. qRT-PCR is performed (as in Example 2) using SY5Y-synuclein RNA. SY5Y-synuclein cells are derived from neuroblastoma cells and have been stably transfected with a WT-synuclein vector.

EXAMPLE 10

Distribution of Lentivirus-Expressed
Alpha-Synuclein in Human Cortical Culture
(HCC)—a Cellular Model for Lewy Body Disease Of interest was the identification of a cellular model for Lewy body disease and/or for PD pathology. Thus, lentivirus-mediated expression of alpha-synuclein in human cortical cultures was used to establish a model of alpha-synuclein deposition in vivo. Experiments were performed on donors, and HCC cells overexpressing wild-type and variant alpha-synuclein to fractionate the cells and localize wild-type alpha-synuclein and variant alpha-synuclein within the cells. In one experiment aggregation of alpha synuclein in a manner matching LB disease was observed in the HCC cells. Further, in one experiment when PLK2 was expressed, the phosphorylation of alpha-synuclein as well as the aggregation increased. In other experiments this was not observed.

Further experiments were performed to determine whether extending culture might increase the accumulation of overexpressed synuclein, and would stress the cells, which also might favor synuclein deposition or toxicity. Accordingly, HCC were transduced with viral vectors expressing WT, A53T, S129A or both A53T/S129A alpha-synuclein mutants. Following transfection cells were grown in vitro for 9, 16 or 23 days before collecting and fractionating. ELISA results were normalized to protein concentration and showed an accumulation of synuclein in the soluble fraction with increasing time. Somewhat greater accumulation was observed with the S129A mutant.

When further experiments were performed with WT, 119-truncated, and E46K AS, the results were as follows. The higher the expression of wild-type the larger the portion of alpha synuclein recovered in the soluble fraction. E46K synuclein showed a 50-100% increase in the amount of phosphorylated alpha-synuclein. However, the E46K mutation did not markedly affect relative amounts of synuclein recovered in the membrane-bound or insoluble fractions. Expression of 119-truncated alpha synuclein led to a slight increase in the relative amount accumulating in the insoluble fraction (about 3 fold higher relative to WT). The increase is expected in view of the published results suggesting that truncated synuclein forms fibrils much more readily in vitro than does full-length (Murray et al. 2003 *Biochemistry* 42:8530). The 119 truncation resulted in an increased association with membranes consistent with the N-terminal domain being responsible for association with lipid bilayers. The increased association with membranes may mitigate the increased tendency of the soluble protein to aggregate. The response of the insoluble fraction to increases in levels of soluble synuclein on overexpression and to truncation, a change favoring aggregation, suggest that it provides a way to identify factors affecting aggregation in the intraneuronal milieu.

The increased alpha-synuclein in the soluble compartment might be shifting the alpha-synuclein to a potentially more vulnerable compartment, leading to changes which could result in increased deposition. Since the kinases proposed to phosphorylate alpha-synuclein at Ser129 are soluble, it seems likely that the soluble alpha-synuclein is more accessible to phosphorylation as well.

Additional experiments are performed to identify inhibitors of the phosphorylation and/or aggregation in this cellular model by expressing the inhibitors in the cells and identifying a reduction in the phosphorylation and/or aggregation.

EXAMPLE 11

Analysis of Endogenous Kinase Activity in Alpha-Synuclein Knock-Out Mice

Figure 8A:
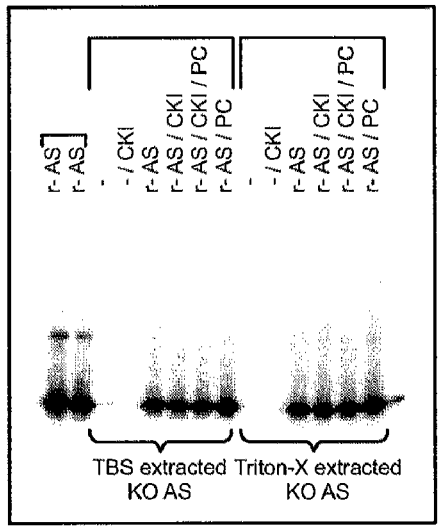
FIGS. 8A and 8B show the in vitro phosphorylation of alpha-synuclein by putative kinase targets in alpha-synuclein KO mouse brain.
Figure 8B:
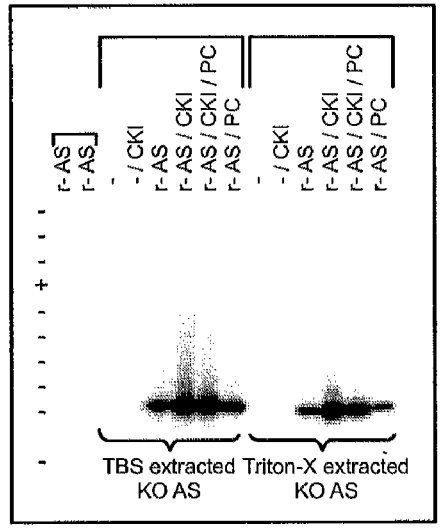

The utilization of an alpha-synuclein knockout (alpha-synuclein KO) mouse brain for the identification of a putative alpha-synuclein kinase has the advantage over the siRNA screen in the following ways: 1) the use of brain material provides relevant and possibly higher levels of brain-specific kinase activity which the HEK cell line may not provide; 2) cofactors may be present in brain (lipid, protein, etc.) which may not be present in cells and 3) absence of any endogenous alpha-synuclein which could be detected as a phosphorylated AS. The inclusion of 25-50 μg of extracts (soluble and detergent soluble) with recombinant alpha-synuclein (rAS) was assessed with 250 μM ATP to determine if appreciable kinase activity was present in crude material. FIG. 8A shows total alpha-synuclein in each reaction indicating equivalent loadings of rAS. In FIG. 8B, the levels of phospho-ser-129 alpha-synuclein were investigated. The rAS in both TBS (sucrose soluble) and TX (Triton-S 100 soluble) extracts was phosphorylated, with roughly twice the level of signal from the TBS material than the TX (although reactions were not normalized for protein). Phosphorylation levels were increased by addition of CKI but were not significantly affected by the addition of phospholipids from soybean. An identical blot was probed for ser-87 phosphorylation in FIG. 9B. This pAb presents cross-reactivity with rAS at 100 ng, thus levels above background indicate true phosphorylation at the ser-87 site. In both TBS and TX reactions there is no significant phosphorylation at this site whereas the CKI spike achieved phosphorylation at appreciable levels. These experiments suggest that measurable and real kinase activit(ies) are present in the soluble and membrane fractions of KO mouse brain and are specific to the ser-129 site compared to ser-87. The potential exists for phosphorylation at other serine or threonine sites in alpha-synuclein but antibodies are not yet available to detect such modifications. Thus, measurable levels of ser-129 specific kinase activity/activities are present in alpha-synuclein KO mouse brain extracts and could serve as starting material for purification of a kinase from the brain.

In FIGS. 8A, 8B, 9A and 9B, cortices of alpha-synuclein KO mouse brain were Dounce homogenized to obtain 200 mM sucrose soluble and 0.1% Triton X-100 soluble extracts with protease and phosphatase inhibitors present. 20 μl of sample (100 μl total volume of reaction) was incubated with 2.4 μg of wt-rAS in the presence or absence of 1000 units of casein kinase I(CKI) as a positive control, and/or 200 μg of phosphatidycholine (PC; soybean lecithin) to increase kinase activiti(es). Reactions were loaded on SDS-PAGE (130 ng total AS) and immunoblotted with Syn-1 (total Syn; 0.1 ug/ml), 11A5 (phospho ser-129; 1 μg/ml) or ELADW110 (phospho ser-87; 2 μg/mL).

The above data shows that PLK2 other direct and/or indirect kinases (such as GRK6), and modulators such as synphilin are novel targets for therapeutic intervention in DLB and PD. PLK2 is a preferred target because it can directly phosphorylate alpha-synuclein specifically at ser-129.

EXAMPLE 12

Effect of Overexpression of PLK Family Members on Synuclein Phosphorylation

Overexpression of PLK family members PLK1, 2 and 3, but not PLK4, increased synuclein phosphorylation above the level of the endogenous kinase in HEK-293 cells.

Methods

HEK-293 naïve cells were transfected with an expression vector encoding PLK1, PLK2, PLK3, or PLK4 under the control of a CMV promoter, or empty vector, together with an expression vector encoding WT-synuclein. All vectors had the sequence coding for the protein of interest. Transfection was accomplished using Lipofectamine 2000 (Invitrogen, Carlsbad, Calif.) with 0.08 μg vector. Cells were washed and harvested 48 hours post-transfection. A Micro BCA (Pierce) total protein assay and total synuclein and phospho-synuclein ELISAs were performed on each plate of treated cells.

Results

Results are summarized in Table 16.

TABLE 16

| Endogenous Kinase | Proportion of total synuclein that is phoshorylated at ser-129 2.0% | Fold Change in Percent Synuclein Phosphorylation |
|---|---|---|
| Endogenous Kinase + synphilin | 1.6% | 0.8 |
| Over-Expressed PLK1 | 4.1% | 2.1 |
| Over-Expressed PLK2 | 42.3% | 21.2 |
| Over-Expressed PLK3 | 79.2% | 39.6 |
| Over-Expressed PLK4 | 1.9% | 1.0 |

PLK2

Over-expression of PLK2 in the 293 cells yielded similar results to those observed in previous experiments, resulting in a 21-fold increase in synuclein phosphorylation, from 2% to 42.3%.

PLK3

The over-expression of PLK3 generated an even more striking 39-fold increase in synuclein phosphorylation, from 2% to 79.2% phospho-synuclein. However, knockdown of PLK3 does not decrease the percentage of phosphorylated synuclein in the 293 cells (see Example 13, infra). PLK3 is structurally most similar to PLK2 of all the PLK family members, so even if PLK3 is not the synuclein kinase, it may be able to perform the same physiological tasks as PLK2. It has been proposed that in the absence of PLK2 expression, PLK3 can functionally compensate for the absent PLK2 (Smith et al., 2006, "Epigenetic inactivation implies a tumor suppressor function in hematologic malignancies for Polo-like kinase 2 but not Polo-like kinase 3.Cell Cycle." *Cell Cycle* 5:1262-4). In addition, over-expression experiments can yield off-target and non-physiological effects and results should be substantiated through additional experimentation such as siRNA knockdown or in vitro transcription/translation experiments.

PLK1

Over-expression of PLK1 resulted in a two-fold increase in the percent of synuclein phosphorylation (from 2% to 4.1%). While not as robust an increase in synuclein phosphorylation as the 21-fold increase with PLK2 or 39-fold increase with PLK3 over-expression, it is still significant. However, as noted above, overexpression of proteins can yield results that do not accurately represent the physiological state within cells and tissues. Over-expression of genes can produce off-target effects and can result in erroneous localizations within cells that do not characterize the true physiological state, and results of over-expression experiments should be substantiated with additional experimentation such as siRNA knockdown or in vitro transcription/translation experiments.

PLK4

Over-expression of PLK4 did not change the percentage of synuclein phosphorylation in 293 cells. The structure of PLK4 is much different from those of the other PLKs, and has only a single polo box domain rather than the two that the other three family members have. The results do not exclude the possibility that in other tissue types, PLK4 may be able to phosphorylate synuclein.

In Vitro Biochemical Assays

In vitro biochemical assays using each of the four PLK family members as the kinase to phosphorylate synuclein were conducted. The results (not shown) mirror the cell-based ovewrexpression assays described above, with PLK1 being able to phosphorylate synuclein moderately, PLK2 and PLK3 having extremely robust phosphorylation of synuclein, and PLK4 exhibiting no ability to phosphorylate synuclein.

EXAMPLE 13 siRNA Knockdown of PLK Family Members

HEK-293 naïve cells were transfected with 40 nM, 100 nM and 200 nM of Dharmacon On Target Plus Smart Pool siRNAs (Darmacon, Lafayette, Colo.) designed to knock down the expression of each of the four PLK family members. The transfection was performed using Lipofectamine 2000 (Invitrogen Carlsbad, Calif.). Cells were washed and harvested 48 hours post-transfection. A Micro BCA (Pierce) total protein assay and total synuclein and phospho-synuclein ELISAs were performed on each plate of treated cells.
PLK2

Figure 10:
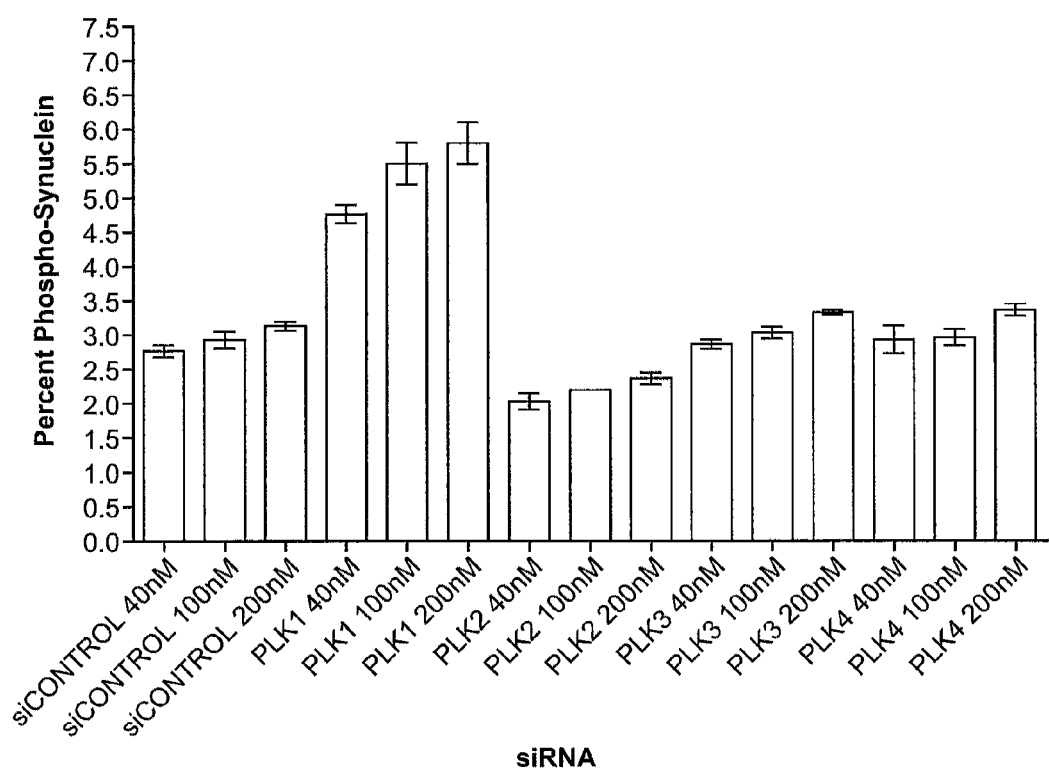
FIG. 10 shows that siRNA knockdown of PLK2, but not PLK3 or PLK4, reduced alpha-synuclein phosphorylation.

The results of the siRNA knockdown experiment are summarized in FIG. 10. In agreement with what we have observed previously for PLK2 siRNA inhibition (see Example 5) knockdown resulted in a 25% decrease in the percentage of phosphorylated synuclein in the 293 cells.
PLK3

The knockdown of PLK3 also had no effect on synuclein phosphorylation, which is not in agreement with the PLK3 overexpression data. This may be due to the fact that overexpression can be somewhat promiscuous, and not indicative of the true physiological state within cells. It may also be that PLK3 is not the synuclein kinase in 293 cells, but it could still be the synuclein kinase in neurons or other cells due to the potential for isoform switching between cell types. Thus, although PLK3 knockdown does not reduce synuclein phosphorylation as we would expect from inhibition of the synuclein kinase, it does not completely eliminate PLK3 as being the correct PLK family member as the synuclein kinase in neurons.
PLK1

Cells treated with PLK1 siRNA showed a 40% decrease in the total protein levels compared to the negative siRNA control, indicating that treatment of cells with PLK1 siRNA inhibits proliferation of cells. This has been noted in the literature, and confirms the role of PLK1 in mitosis. Taking into account this change in total protein levels, knockdown of PLK1 transcript results in a 60-90% increase in the percentage of phospho-synuclein. This indicates that PLK1 is negative regulator of synuclein phosphorylation. It appears that when PLK1 is present in cell, it regulates PLK2 or it's upstream pathway and accordingly the level of PLK2-mediated phosphorylation of synuclein. This increase in phospho-synuclein with PLK1 knockdown has been observed in two independent experiments, and is intriguing as a potential regulator of PLK2-driven synuclein phosphorylation.
PLK4

Knockdown of PLK4 with siRNA had no effect on synuclein phosphorylation, in accord with the PLK4 overexpression data above (Example 11).

EXAMPLE 14

Treatment of Primary Neuronal Cultures with Kinase Inhibitors

The effect on levels of serine-129 synuclein was tested for kinase inhibitors with various specificities in rat and mouse primary cortical cell culture was tested.

Table 17 shows the inhibitors used in the experiment:

TABLE 17

| | Inhibitor | Primary Specificity |
|---|---|---|
| 1 | ELN-481080 | PLK1 |
| 2 | ELN-481574-2 (BI 2536) | PLK 1, 2, 3 |
| 3 | ELN-481530 | JNK3 |
| 4 | DMAT (2-Dimethylamino-4,5,6,7-tetrabromo-1H-benzimidazole) | Casein kinase 2 |
| 5 | Scytonemin | PLK1, PKCβ1, PKCβ2, Cdk1/B, Myt1, and Chk1 |
| 6 | K252A | Generic kinase inhibitor |
| 7 | Wortmannin | Generic kinase inhibitor |
| 8 | N-benzoyl staurosporine | Generic kinase inhibitor |
| 9 | TBB (4,5,6,7-Tetrabromo-2-azabenzimidazole) | ATP/GTP-competitive inhibitor of casein kinase 2 |

Preparation of Mouse Neuronal Cell Cultures

Mouse cortical cultures from fetal (i) Swiss-Webster, (ii) C56BL/6 WT and (iii) C56BL/6 E46K-Synuclein Trangenic mice were prepared and maintained in B27/DMEM/1% Penicillin-Streptomycin at 37° C./10% $CO_2$ for three to fourteen days and then treated with kinase inhibitors.

Cultures were exposed to inhibitors for two hours in B27/DMEM/1% Penicillin-Streptomycin. Cells were immediately washed in 100 μL of PBS plus $Mg^{2+}$ and $Ca^{2+}$, and harvested in ice-cold CEB minus EGTA plus protease inhibitors, frozen on dry ice and stored at −80° C. until processed. A Micro BCA (Pierce) total protein assay, and total synuclein and phospho-synuclein ELISAs were performed on each plate of treated cells using standard methods.

Preparation of Rat Neuronal Cell Cultures

Rat Ventral Mesencephalon (RVM) cultures were prepared from E15 Wistar rats. The RVM cultures were cultured for 2 days and transduced with 0.75 MOI E46K-Synuclein lentivirus alone, or 0.75 MOI E46K-Synuclein lentivirus plus 0.75 MOI ca-PLK2 lentivirus. The mid-brain region, ventral mesencephalon, from embryonic day 15 Wistar rats were dissected and pooled for processing for culture as described previously in Steven et al., 2001, Genetics 10:1317-24 with the medium supplement replaced with B27 (Invitrogen) and 1% FBS (HyClone). Transduced cultures were maintained in neuronal media with B27/1% FBS and 37° C./5% $CO_2$ until treated with inhibitors. On DIV 17 (which corresponds to 15 days after viral transduction of the cultures) cells were treated with inhibitors for two hours. Cells were then harvested as detailed above in neuronal media with B27/1% FBS. A Micro BCA (Pierce) total protein assay, and total synuclein and phospho-synuclein ELISAs were performed on each plate of treated cells using standard methods.

Results

The effects of inhibitors on phosphorylation of alpha-synuclein are summarized in Tables 18 and 19. Table 18 shows that the extent of inhibition of synuclein phosphorylation by selected inhibitors is similar for the endogenous kinase in mouse and rat primary cultures, as well as a constitutively active PLK2 variant (caPLK2). In caPLK2 the polo-box has been deleted, activating the Thr to Asp mutation in the kinase activation loop. Table 19 shows the rank order of potency for selected inhibitors is similar between cell types and across species (mouse, rat and human)

The results of treatment of several primary neuronal cultures with PLK and other inhibitors were very similar to those observed in 293 cells in both the $EC_{50}$ values (Table 18) and the rank order of potency (Table 19). The $EC_{50}$ values for the potent PLK inhibitor BI 2536 (ELN-481574-2) in all cellular paradigms were in the nanomolar range, with most $EC_{50}$ values being 100 nM or less, and has an $IC_{50}$ of 27 nM in the in vitro biochemical assay. This PLK inhibitor is a very potent inhibitor of synuclein phosphorylation in primary neuronal cultures in mouse and rat, substantiating the role of a PLK family member as the synuclein kinase.

The second most potent inhibitor in most of the cellular paradigms tested was the generic kinase inhibitor K252A ($EC_{50}$ values of 3-7 µM). In the in vitro biochemical reaction, K252A does not inhibit PLK2-driven synuclein phosphorylation ($IC_{50}$>10 µM), indicating that its inhibition of synuclein phosphorylation is through an upstream or downstream regulator of PLK2.

The third most potent inhibitor of synuclein phosphorylation in primary neuronal cells is ELN-481080, a PLK1 inhibitor that also has inhibitory activity on PLK2, and to a lesser degree, PLK3 and PLK4 (see Table 21). The $IC_{50}$ of ELN-481080 was 7.7 µM, and the $EC_{50}$ values in most cellular paradigms was 12-38 µM.

The fourth most potent inhibitor of synuclein phosphorylation in primary neuronal cells is the casein kinase 2 inhibitor DMAT (2-Dimethylamino-4,5,6,7-tetrabromo-1H-benzimidazole). The $EC_{50}$ values for inhibition of synuclein phosphorylation in each of the cell types were 16-33 µM. In the biochemical assay DMAT was the second most potent inhibitor of synuclein phosphorylation with an $IC_{50}$ of 2.07 µM. That DMAT can directly act on PLK2 to inhibit synuclein phosphorylation suggests that reports by others using to DMAT to show that the CKII is the synuclein kinase may be due to the inhibitory effect the DMAT has on PLK2 and not on casein kinase 2. To confirm that the inhibitory effect DMAT is due to inhibition of PLK2, MCC were treated with TBB, a very specific CKII inhibitor. TBB had no effect on synuclein phosphorylation, even at concentrations of 100 µM (data not shown). Thus, we are confident that the inhibitory effect of DMAT on synuclein phosphorylation is due to its direct activity on PLK2 and not CKII.

The other four inhibitors tested, Scytonemin, Wortmannin and N-benzoyl staurosporine did not inhibit 50% of synuclein phosphorylation in any of the cells or in the in vitro assay. ELN-481530, the JNK3 inhibitor, also did not inhibit PLK2-driven phosphorylation in vitro, or in most cell types tested. However, in RVM stably transduced with E46K-synuclein (but not in conjunction with caPLK2), concentrations of 1 µM or greater of ELN-481530 and above inhibited 50% of synuclein phosphorylation, with the inhibition reaching a plateau of 50%. In addition, 293 cells over-expressing human WT-synuclein and WT-PLK2 reached the same plateau of 50% inhibition at 10 µM ELN-481530. While further work needs to be done to elucidate the role that JNK may play in synuclein phosphorylation, it seems reasonable to suggest the JNK may be a regulator of PLK2 and synuclein phosphorylation in certain cell types.

TABLE 18

The $EC_{50}/IC_{50}$ values for selected inhibitors are similar between cell types and across species (mouse, rat and human)

| Inhibitor | Straight Biochemical | WT-MCC | E46K-Syn TG MCC | Swiss-Webster MCC | RVM E46K-Synuclein | RVM E46K-Synuclein caPLK2 | Endogenous Kinase (293) | Over-Expressed PLK2 (293)* |
|---|---|---|---|---|---|---|---|---|
| ELN-481080 | 7.7 µM | 17.3 µM | 12.3 µM | 14.8 µM | ~100 µM | 25.2 µM | ~100 µM | 38 µM |
| ELN-481574-2 | 0.027 µM | <0.1 µM | <0.1 µM | 0.092 µM | 0.598 µM | 0.078 µM | 0.054 µM | 0.07 µM |
| DMAT | 2.07 µM | 18.7 µM | 16.6 µM | 21.6 µM | 20 µM | 28.5 µM | 33 µM | 18.6 µM |
| K252A | >10 µM | 3 µM | 3.1 µM | 2.9 µM | 3.2 µM | 3.5 µM | 3.6 µM | 7.1 µM |
| ELN-481530 | >100 µM | >100 µM | >100 µM | NT | ~1 µM | >100 µM | >100 µM | ~10 µM |
| Scytonemin | >100 µM | >100 µM | >100 µM | NT | >100 µM | >100 µM | >100 µM | >100 µM |
| Wortmannin | >100 µM | >100 µM | >100 µM | NT | >100 µM | >100 µM | >100 µM | >100 µM |
| N-Benzoyl Staurosporine | >100 µM | >100 µM | >100 µM | NT | >100 µM | >100 µM | >100 µM | >100 µM |

*See Example 14
NT - Inhibitor not tested in these cells

TABLE 19

The rank order of potency for selected inhibitors is similar for different cell types and species (mouse, rat and human)

| Inhibitor | Straight Biochemical | WT-MCC | E46K-Syn TG MCC | Swiss-Webster MCC | RVM E46K-Synuclein | RVM E46K-Synuclein caPLK2 | Endogenous Kinase (293) | Over-Expressed PLK2 (293)* |
|---|---|---|---|---|---|---|---|---|
| ELN-481080 | 3 | 3 | 3 | 3 | 5 | 3 | 4 | 5 |
| ELN-481574-2 | 1 | 1 | 1 | 1 | 1 | 1 | 1 | 1 |
| DMAT | 2 | 4 | 4 | 4 | 4 | 4 | 3 | 4 |
| K252A | 4 | 2 | 2 | 2 | 3 | 2 | 2 | 2 |
| ELN-481530 | NA | NA | NA | NA | 2 | NA | NA | 3 |
| Scytonemin | NA | NA | NA | NA | NA | NA | NA | NA |

TABLE 19-continued

The rank order of potency for selected inhibitors is similar for different cell types and species (mouse, rat and human)

| Inhibitor | Straight Biochemical | WT-MCC | E46K-Syn TG MCC | Swiss-Webster MCC | RVM E46K-Synuclein | RVM E46K-Synuclein caPLK2 | Endogenous Kinase (293) | Over-Expressed PLK2 (293)* |
|---|---|---|---|---|---|---|---|---|
| Wortmannin | NA | NA | NA | NA | NA | NA | NA | NA |
| N-Benzoyl Staurosporine | NA | NA | NA | NA | NA | NA | NA | NA |

*See Example 14
NA—Not Applicable due to an $EC_{50}$ not being reached

EXAMPLE 15

Specificity of ELN-481574

PLK inhibitor ELN-481574-2 (BI 2536) exhibited high potency for reducing alpha-synuclein phosphorylation in a variety of cells, including primary neuronal cells (see Example 14). The inhibitor was screened against a panel of 260 kinases (almost half the kinome) and found that at 10 uM, ELN-481574 was very potent in inhibiting PLK2 and PLK3, although the compound also inhibited several CaMKs and casein kinases. The ten kinases that were inhibited the most by ELN-481574 were subjected to a nine-point dose-response (0.003 uM to 3 uM) of the compound to determine the IC50. The ELN-481574 compound has 16-fold selectivity for PLK2 ($IC_{50}$ 11 nM) and 13-fold selectivity for PLK3 ($IC_{50}$ 14 nM) over the next closest kinase $IC_{50}$ (CaMKIIδ 182 nM). See Table 20 for a summary. This confirms that this inhibitor is indeed potent and highly selective for at least two members of the PLK family.

TABLE 20

Summary of $IC_{50}$ Values for ELN-481574-2

| Kinase | IC50 (nM) |
|---|---|
| PLK2 | 11 |
| PLK3 | 14 |
| CaMKIIδ | 182 |
| FAK | 239 |
| EGFR(L858R) | 264 |
| Fes | 341 |
| MLCK | 643 |
| PKCµ | 1,126 |
| CK1γ3 | 1,231 |
| CaMKIIβ | 1,496 |

EXAMPLE 16

Effect of Kinase Inhibitors in HEK-293 Cells Overexpressing PLK Family Members HEK-293 cells as described in Example 12, which overexpress synuclein in conjunction with empty vector or one of the PLK family members, were exposed to inhibitors. $EC_{50}$ values (Table 21) and a rank order of potency (Table 22) was similar to that seen in primary neuronal cells (see Example 13). The PLK inhibitor ELN-481574-2 was the most potent inhibitor of synuclein phosphorylation by the endogenous kinase and by each of the over-expressed PLKs. The $EC_{50}$ for the endogenous kinase was 99 nM, and was 36 nM, 80 nM, 438 nM and 192 nM for each of the PLK1, 2, 3 and 4. The $EC_{50}$ for PLK3 is somewhat higher than it is for the endogenous kinase or the other PLKs.

The second most potent inhibitor of synuclein phosphorylation was DMAT, with $EC_{50}$ values of ~14-74 µM for the over-expressed PLKs and 56 µM for the endogenous kinase. The PLK1 inhibitor ELN-481080 shows selectivity for PLK1 (16.7 µM) over PLK2 (47.8 µM), and while an $EC_{50}$ was not reached for inhibition of synuclein phosphorylation by overexpressed PLK3 or PLK4, ELN-481080 did inhibit 30-40% of synuclein phosphorylation at concentrations of 30-100 µM. It should be noted that while the $EC_{50}$ for ELN-481080 activity on the endogenous kinase was >100 µM in this experiment, in previous experiments, the $EC_{50}$ has been ~100 µM (Table 18), which is still within the three-fold range of variation of the $EC_{50}$ of PLK2.

In this experiment, treatment of overexpressed PLK family members with the JNK3 inhibitor ELN-481530 did not inhibit synuclein phosphorylation by 50%. However, it did inhibit 30-45% of synuclein phosphorylation by cells over-expressing PLK2 or PLK3 at concentrations of 1 µM and above. In the presence of endogenous kinase or over-expressed PLK1 or PLK4, inhibition was lower, reaching a maximum of 15-20%.

TABLE 21

The $EC_{50}$ values for ELN-481574-2 is similar for the four PLK family members $EC_{50}$ of Selected Inhibitors Based on the Percent Inhibition of Synuclein Phosphorylation

| Inhibitor | Synuclein + Vector | Synuclein + PLK1 | Synuclein + PLK2 | Synuclein + PLK3 | Synuclein + PLK4 |
|---|---|---|---|---|---|
| ELN-481080 | >100 µM | 16.7 µM | 47.8 µM | >100 µM | >100 µM |
| ELN-481574-2 | 0.099 µM | 0.036 µM | 0.08 µM | 0.438 µM | 0.192 µM |
| DMAT | 55.7 µM | 27.2 µM | 13.9 µM | 37.3 µM | 74.3 µM |
| ELN-481530 | >100 µM | >100 µM | >100 µM | >100 µM | >100 µM |

TABLE 22

The rank order of potency of inhibitors tested is very similar between PLK family members Rank Order of Potency of Inhibitors Based on Percent Inhibition of Synuclein Phosphorylation

| Inhibitor | Synuclein + Vector | Synuclein + PLK1 | Synuclein + PLK2 | Synuclein + PLK3 | Synuclein + PLK4 |
|---|---|---|---|---|---|
| ELN-481080 | NA | 2 | 3 | 3 | NA |
| ELN-481574-2 | 1 | 1 | 1 | 1 | 1 |
| DMAT | 2 | 3 | 2 | 2 | 2 |
| ELN-481530 | NA | NA | NA | NA | NA |

NA—Not Applicable due to an $EC_{50}$ not being reached

EXAMPLE 17

Effect of Staurosporin in HEK-293 Cells Overexpressing PLK2

HEK-293 cells as described in Example 12, which overexpress synuclein or synuclein and PLK2. The $EC_{50}$ value for the endogenous kinase (synuclein only) was 4.35 µM, and 11.16 µM for PLK2 over-expressing cells.

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but instead should be determined with reference to the issued claims along with their full scope of equivalents. All publications, references (including accession numbers), and patent documents cited in this application are incorporated by reference in their entirety for all purposes to the same extent as if each individual publication or patent document were so individually denoted.

What is claimed is:

1. A method of identifying an agent that reduces alpha-synuclein phosphorylation in a mammalian cell comprising:
   a) providing a mammalian cell expressing alpha-synuclein and expressing PLK2;
   b) contacting the mammalian cell with a test agent; and
   c) measuring the level of phosphorylated alpha-synuclein in the mammalian cell, wherein a reduction in the level of phosphorylated alpha-synuclein in the mammalian cell relative to the level in a control cell not contacted with the test agent is indicative that the test agent reduces alpha-synuclein phosphorylation.

2. The method of claim 1, wherein the mammalian cell overexpresses alpha-synuclein.

3. The method of claim 1, wherein the mammalian cell further expresses synphilin.

4. The method of claim 1, wherein the mammalian cell further expresses PLK1 and/or PLK3 and/or PLK4.

5. The method of claim 1, wherein the mammalian cell further expresses PLK1.

6. The method of claim 5, wherein the mammalian cell further expresses PLK3.

7. The method of claim 6, wherein the mammalian cell further expresses PLK4.

8. The method of claim 3, wherein the mammalian cell further expresses PLK1 or PLK3.

9. The method of claim 8, wherein the mammalian cell expresses both PLK1 and PLK3.

10. A method of identifying an agent that reduces alpha-synuclein phosphorylation in a mammalian cell comprising:
    a) providing a mammalian cell expressing alpha-synuclein and expressing PLK2 and expressing synphilin;
    b) contacting the mammalian cell with a test agent; and
    c) measuring the level of phosphorylated alpha-synuclein in the mammalian cell, wherein a reduction in the level of phosphorylated alpha-synuclein in the mammalian cell relative to the level in a control cell not contacted with the test agent is indicative that the test agent reduces alpha-synuclein phosphorylation.

11. The method of claim 10, wherein the mammalian cell further expresses PLK1 or PLK3.

12. The method of claim 11, wherein the mammalian cell expresses both PLK1 and PLK3.

* * * * *

```
                        SEQUENCE LISTING

<160> NUMBER OF SEQ ID NOS: 22

<210> SEQ ID NO 1
<211> LENGTH: 2795
<212> TYPE: DNA
<213> ORGANISM: Homo sapiens

<400> SEQUENCE: 1
gcacaagtgg accggggtgt tgggtgctag tcggcaccag aggcaagggt gcgaggacca       60
cggccggctc ggacgtgtga ccgcgcctag ggggtggcag cgggcagtgc ggggcggcaa      120
ggcgaccatg gagcttttgc ggactatcac ctaccagcca gccgccagca ccaaaatgtg      180
cgagcaggcg ctgggcaagg gttgcggagc ggactcgaag aagaagcggc cgccgcagcc      240
ccccgaggaa tcgcagccac ctcagtccca ggcgcaagtg ccccccggcgg cccctcacca     300 ccatcaccac cattcgcact cggggccgga gatctcgcgg attatcgtcg accccacgac      360
tgggaagcgc tactgccggg gcaaagtgct gggaaagggt ggctttgcaa aatgttacga      420
gatgacagat ttgacaaata acaaagtcta cgccgcaaaa attattcctc acagcagagt      480
agctaaacct catcaaaggg aaaagattga caaagaaata gagcttcaca gaattcttca      540
tcataagcat gtagtgcagt tttaccacta cttcgaggac aaagaaaaca tttacattct      600
cttggaatac tgcagtagaa ggtcaatggc tcatattttg aaagcaagaa aggtgttgac      660
agagccagaa gttcgatact acctcaggca gattgtgtct ggactgaaat accttcatga      720
acaagaaatc ttgcacagag atctcaaact agggaacttt tttattaatg aagccatgga     780
actaaaagtt ggggacttcg gtctggcagc caggctagaa cccttggaac acagaaggag      840
aacgatatgt ggtaccccaa attatctctc tcctgaagtc ctcaacaaac aaggacatgg      900
ctgtgaatca gacatttggg ccctgggctg tgtaatgtat acaatgttac tagggaggcc      960
cccatttgaa actacaaatc tcaaagaaac ttataggtgc ataagggaag caaggtatac     1020
aatgccgtcc tcattgctgg ctcctgccaa gcacttaatt gctagtatgt tgtccaaaaa     1080
cccagaggat cgtcccagtt tggatgacat cattcgacat gacttttttt tgcagggctt     1140
```

-continued

```
cactccggac agactgtctt ctagctgttg tcatacagtt ccagatttcc acttatcaag    1200
cccagctaag aatttcttta agaaagcagc tgctgctctt tttggtggca aaaagacaa     1260 agcaagatat attgacacac ataatagagt gtctaaagaa gatgaagaca tctacaagct    1320
taggcatgat ttgaaaaaga cttcaataac tcagcaaccc agcaaacaca ggacagatga    1380
ggagctccag ccacctacca ccacagttgc caggtctgga acaccgcag tagaaaacaa     1440 gcagcagatt gggatgcta ttcggatgat agtcagaggg actcttggca gctgtagcag     1500
cagcagtgaa tgccttgaag acagtaccat gggaagtgtt gcagacacag tggcaagggt    1560
tcttcgggga tgtctggaaa acatgccgga agctgattgc attcccaaag agcagctgag    1620
cacatcattt cagtgggtca ccaaatgggt tgattactct aacaaatatg gctttgggta    1680
ccagctctca gaccacaccg tcggtgtcct tttcaacaat ggtgctcaca tgagcctcct    1740
tccagacaaa aaacagttc actattacgc agagcttggc caatgctcag ttttcccagc    1800
aacagatgct cctgagcaat ttattagtca agtgacggtg ctgaaatact tttctcatta   1860
catggaggag aacctcatgg atggtggaga tctgcctagt gttactgata ttcgaagacc    1920
tcggctctac ctccttcagt ggctaaaatc tgataaggcc ctaatgatgc tctttaatga    1980
tggcaccttt caggtgaatt tctaccatga tcatacaaaa atcatcatct gtagccaaaa    2040
tgaagaatac cttctcacct acatcaatga ggataggata tctacaactt tcaggctgac    2100
aactctgctg atgtctggct gttcatcaga attaaaaaat cgaatggaat atgccctgaa    2160
catgctctta caaagatgta actgaaagac ttttcgaatg gaccctatgg gactcctctt    2220
ttccactgtg agatctacag ggaagccaaa agaatgatct agagtatgtt gaagaagatg    2280
gacatgtggt ggtacgaaaa caattcccct gtggcctgct ggactggttg gaaccagaac    2340
aggctaaggc atacagttct tgactttgga caatccaaga gtgaaccaga atgcagtttt    2400
ccttgagata cctgtttaa aaggttttc agacaatttt gcagaaaggt gcattgattc      2460
ttaaattctc tctgttgaga gcatttcagc cagaggactt tggaactgtg aatatacttc    2520
ctgaagggga gggagaaggg aggaagctcc catgttgttt aaaggctgta attggagcag    2580
cttttggctg cgtaactgtg aactatggcc atatataatt ttttttcatt aattttgaa    2640 gatacttgtg ctggaaaag tgcattcctt gttaataaac ttttatta ttacagccca      2700 aagagcagta tttattatca aaatgtcttt ttttttatgt tgaccatttt aaaccgttgg    2760
caataaagag tatgaaaacg cagaaaaaaa aaaaa                               2795
```

<210> SEQ ID NO 2
<211> LENGTH: 685
<212> TYPE: PRT
<213> ORGANISM: Homo sapiens

<400> SEQUENCE: 2

```
Met Glu Leu Leu Arg Thr Ile Thr Tyr Gln Pro Ala Ala Ser Thr Lys
1               5                   10                  15

Met Cys Glu Gln Ala Leu Gly Lys Gly Cys Gly Ala Asp Ser Lys Lys
            20                  25                  30

Lys Arg Pro Pro Gln Pro Glu Glu Ser Gln Pro Gln Ser Gln
        35                  40                  45

Ala Gln Val Pro Pro Ala Ala Pro His His His His His Ser His
    50                  55                  60

Ser Gly Pro Glu Ile Ser Arg Ile Ile Val Asp Pro Thr Thr Gly Lys
65                  70                  75                  80

Arg Tyr Cys Arg Gly Lys Val Leu Gly Lys Gly Gly Phe Ala Lys Cys
                85                  90                  95
```

```
Tyr Glu Met Thr Asp Leu Thr Asn Asn Lys Val Tyr Ala Ala Lys Ile
            100                 105                 110

Ile Pro His Ser Arg Val Ala Lys Pro His Gln Arg Glu Lys Ile Asp
            115                 120                 125

Lys Glu Ile Glu Leu His Arg Ile Leu His His Lys His Val Val Gln
        130                 135                 140

Phe Tyr His Tyr Phe Glu Asp Lys Glu Asn Ile Tyr Ile Leu Leu Glu
145                 150                 155                 160

Tyr Cys Ser Arg Arg Ser Met Ala His Ile Leu Lys Ala Arg Lys Val
                165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
        195                 200                 205

Gly Asn Phe Phe Ile Asn Glu Ala Met Glu Leu Lys Val Gly Asp Phe
        210                 215                 220

Gly Leu Ala Ala Arg Leu Glu Pro Leu Glu His Arg Arg Arg Thr Ile
225                 230                 235                 240

Cys Gly Thr Pro Asn Tyr Leu Ser Pro Glu Val Leu Asn Lys Gln Gly
                245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
        275                 280                 285

Tyr Arg Cys Ile Arg Glu Ala Arg Tyr Thr Met Pro Ser Ser Leu Leu
            290                 295                 300

Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Phe Leu Gln
                325                 330                 335

Gly Phe Thr Pro Asp Arg Leu Ser Ser Ser Cys Cys His Thr Val Pro
            340                 345                 350

Asp Phe His Leu Ser Ser Pro Ala Lys Asn Phe Phe Lys Lys Ala Ala
        355                 360                 365

Ala Ala Leu Phe Gly Gly Lys Lys Asp Lys Ala Arg Tyr Ile Asp Thr
        370                 375                 380

His Asn Arg Val Ser Lys Glu Asp Glu Asp Ile Tyr Lys Leu Arg His
385                 390                 395                 400

Asp Leu Lys Lys Thr Ser Ile Thr Gln Gln Pro Ser Lys His Arg Thr
                405                 410                 415

Asp Glu Glu Leu Gln Pro Pro Thr Thr Thr Val Ala Arg Ser Gly Thr
            420                 425                 430

Pro Ala Val Glu Asn Lys Gln Gln Ile Gly Asp Ala Ile Arg Met Ile
        435                 440                 445

Val Arg Gly Thr Leu Gly Ser Cys Ser Ser Ser Glu Cys Leu Glu
            450                 455                 460

Asp Ser Thr Met Gly Ser Val Ala Asp Thr Val Ala Arg Val Leu Arg
465                 470                 475                 480

Gly Cys Leu Glu Asn Met Pro Glu Ala Asp Cys Ile Pro Lys Glu Gln
                485                 490                 495

Leu Ser Thr Ser Phe Gln Trp Val Thr Lys Trp Val Asp Tyr Ser Asn
            500                 505                 510

Lys Tyr Gly Phe Gly Tyr Gln Leu Ser Asp His Thr Val Gly Val Leu
        515                 520                 525
```

Phe Asn Asn Gly Ala His Met Ser Leu Leu Pro Asp Lys Lys Thr Val
    530                 535                 540

His Tyr Tyr Ala Glu Leu Gly Gln Cys Ser Val Phe Pro Ala Thr Asp
545                 550                 555                 560

Ala Pro Glu Gln Phe Ile Ser Gln Val Thr Val Leu Lys Tyr Phe Ser
                565                 570                 575

His Tyr Met Glu Glu Asn Leu Met Asp Gly Gly Asp Leu Pro Ser Val
            580                 585                 590

Thr Asp Ile Arg Arg Pro Arg Leu Tyr Leu Leu Gln Trp Leu Lys Ser
        595                 600                 605

Asp Lys Ala Leu Met Met Leu Phe Asn Asp Gly Thr Phe Gln Val Asn
    610                 615                 620

Phe Tyr His Asp His Thr Lys Ile Ile Ile Cys Ser Gln Asn Glu Glu
625                 630                 635                 640

Tyr Leu Leu Thr Tyr Ile Asn Glu Asp Arg Ile Ser Thr Thr Phe Arg
                645                 650                 655

Leu Thr Thr Leu Leu Met Ser Gly Cys Ser Ser Glu Leu Lys Asn Arg
            660                 665                 670

Met Glu Tyr Ala Leu Asn Met Leu Leu Gln Arg Cys Asn
        675                 680                 685

<210> SEQ ID NO 3
<211> LENGTH: 19
<212> TYPE: DNA
<213> ORGANISM: Artificial
<220> FEATURE:
<223> OTHER INFORMATION: Synthetic siRNA sequence

<400> SEQUENCE: 3
ccggagatct cgcggatta                                                   19

<210> SEQ ID NO 4
<211> LENGTH: 19
<212> TYPE: DNA
<213> ORGANISM: Artificial
<220> FEATURE:
<223> OTHER INFORMATION: Synthetic siRNA sequence

<400> SEQUENCE: 4
ggggcaaagt gctgggaaa                                                   19

<210> SEQ ID NO 5
<211> LENGTH: 19
<212> TYPE: DNA
<213> ORGANISM: Artificial
<220> FEATURE:
<223> OTHER INFORMATION: Synthetic siRNA sequence

<400> SEQUENCE: 5
tcacagcaga gtagctaaa                                                   19

<210> SEQ ID NO 6
<211> LENGTH: 19
<212> TYPE: DNA
<213> ORGANISM: Artificial
<220> FEATURE:
<223> OTHER INFORMATION: Synthetic siRNA sequence

<400> SEQUENCE: 6
gggaaaagat tgacaaaga                                                   19

```
<210> SEQ ID NO 7
<211> LENGTH: 19
<212> TYPE: DNA
<213> ORGANISM: Artificial
<220> FEATURE:
<223> OTHER INFORMATION: Synthetic siRNA sequence

<400> SEQUENCE: 7
gattgtgtct ggactgaaa                                                    19

<210> SEQ ID NO 8
<211> LENGTH: 19
<212> TYPE: DNA
<213> ORGANISM: Artificial
<220> FEATURE:
<223> OTHER INFORMATION: Synthetic siRNA sequence

<400> SEQUENCE: 8
gcacagagat ctcaaacta                                                    19

<210> SEQ ID NO 9
<211> LENGTH: 19
<212> TYPE: DNA
<213> ORGANISM: Artificial
<220> FEATURE:
<223> OTHER INFORMATION: Synthetic siRNA sequence

<400> SEQUENCE: 9
acacagaagg agaacgata                                                    19

<210> SEQ ID NO 10
<211> LENGTH: 19
<212> TYPE: DNA
<213> ORGANISM: Artificial
<220> FEATURE:
<223> OTHER INFORMATION: Synthetic siRNA sequence

<400> SEQUENCE: 10
aggagaacga tatgtggta                                                    19

<210> SEQ ID NO 11
<211> LENGTH: 19
<212> TYPE: DNA
<213> ORGANISM: Artificial
<220> FEATURE:
<223> OTHER INFORMATION: Synthetic siRNA sequence

<400> SEQUENCE: 11
cataagggaa gcaaggtat                                                    19

<210> SEQ ID NO 12
<211> LENGTH: 19
<212> TYPE: DNA
<213> ORGANISM: Artificial
<220> FEATURE:
<223> OTHER INFORMATION: Synthetic siRNA sequence

<400> SEQUENCE: 12
gctagtatgt tgtccaaaa                                                    19

<210> SEQ ID NO 13
<211> LENGTH: 19
<212> TYPE: DNA
<213> ORGANISM: Artificial
<220> FEATURE:
<223> OTHER INFORMATION: Synthetic siRNA sequence

<400> SEQUENCE: 13
```

| | | |
|---|---|---|
| gaagacatct acaagctta | | 19 |

<210> SEQ ID NO 14
<211> LENGTH: 19
<212> TYPE: DNA
<213> ORGANISM: Artificial
<220> FEATURE:
<223> OTHER INFORMATION: Synthetic siRNA sequence

<400> SEQUENCE: 14
catcaatgag gataggata                                            19

<210> SEQ ID NO 15
<211> LENGTH: 19
<212> TYPE: DNA
<213> ORGANISM: Artificial
<220> FEATURE:
<223> OTHER INFORMATION: Synthetic siRNA sequence

<400> SEQUENCE: 15
gacatgtggt ggtacgaaa                                            19

<210> SEQ ID NO 16
<211> LENGTH: 19
<212> TYPE: DNA
<213> ORGANISM: Artificial
<220> FEATURE:
<223> OTHER INFORMATION: Synthetic siRNA sequence

<400> SEQUENCE: 16
cagaacaggc taaggcata                                            19

<210> SEQ ID NO 17
<211> LENGTH: 19
<212> TYPE: DNA
<213> ORGANISM: Artificial
<220> FEATURE:
<223> OTHER INFORMATION: Synthetic siRNA sequence

<400> SEQUENCE: 17
gtgcattcct tgttaataa                                            19

<210> SEQ ID NO 18
<211> LENGTH: 21
<212> TYPE: DNA
<213> ORGANISM: Artificial
<220> FEATURE:
<223> OTHER INFORMATION: Synthetic siRNA sequence

<400> SEQUENCE: 18
gguauacaau gccguccuct t                                         21

<210> SEQ ID NO 19
<211> LENGTH: 21
<212> TYPE: DNA
<213> ORGANISM: Artificial
<220> FEATURE:
<223> OTHER INFORMATION: Synthetic siRNA sequence

<400> SEQUENCE: 19
ggacuuugga acugugaaut t                                         21

<210> SEQ ID NO 20
<211> LENGTH: 21
<212> TYPE: DNA
<213> ORGANISM: Artificial

```
<220> FEATURE:
<223> OTHER INFORMATION: Synthetic siRNA sequence

<400> SEQUENCE: 20
gggaaaagau ugacaaagat t                                                    21

<210> SEQ ID NO 21
<211> LENGTH: 25
<212> TYPE: PRT
<213> ORGANISM: Artificial
<220> FEATURE:
<223> OTHER INFORMATION: Synthetic motif characterizing one class of
      zinc finger proteins
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid or absent
<220> FEATURE:
<221> NAME/KEY: MISC_FEATURE
<222> LOCATION: (7)..(18)
<223> OTHER INFORMATION: Xaa = any amino acid
<220> FEATURE:
<221> NAME/KEY: MISC_FEATURE
<222> LOCATION: (20)..(22)
<223> OTHER INFORMATION: Xaa = any amino acid
<220> FEATURE:
<221> NAME/KEY: MISC_FEATURE
<222> LOCATION: (23)..(24)
<223> OTHER INFORMATION: Xaa = any amino acid or absent

<400> SEQUENCE: 21

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 22
<211> LENGTH: 140
<212> TYPE: PRT
<213> ORGANISM: Homo sapiens

<400> SEQUENCE: 22

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```